US006800659B2

(12) United States Patent
Roifman et al.

(10) Patent No.: US 6,800,659 B2
(45) Date of Patent: Oct. 5, 2004

(54) COMPOUNDS FOR MODULATING CELL PROLIFERATION

(75) Inventors: Chaim M. Roifman, Toronto (CA); Thomas Grunberger, Toronto (CA); Olga Rounova, Toronto (CA); Demin Peter, Toronto (CA); Nigel Sharfe, Toronto (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 09/834,728

(22) Filed: Apr. 12, 2001

(65) Prior Publication Data

US 2003/0109502 A1 Jun. 12, 2003

Related U.S. Application Data

(60) Provisional application No. 60/196,936, filed on Apr. 13, 2000.

(51) Int. Cl.[7] ............... A61K 31/275; A61P 35/02; A61P 35/04; C07C 47/11
(52) U.S. Cl. ............... 514/521; 558/390; 558/392; 558/402; 558/403; 558/445; 568/442; 514/523; 514/528; 514/701; 514/238.5; 514/424; 514/521; 556/405; 544/157; 544/158; 544/159; 548/579
(58) Field of Search ............... 558/390, 391, 558/403, 409, 445; 544/157, 158, 159; 548/579; 556/417; 514/238.5, 424, 521, 701, 528; 568/442

(56) References Cited

U.S. PATENT DOCUMENTS

| | | | |
|---|---|---|---|
| 2,798,881 A | 7/1957 | Baer et al. |
| 3,125,597 A | 3/1964 | Wahl et al. |
| 3,852,683 A | 12/1974 | Webster et al. |
| 4,263,394 A | 4/1981 | Gates et al. |
| 4,554,238 A | 11/1985 | Bushman |
| 4,617,373 A | 10/1986 | Pruett et al. |
| 4,632,895 A | 12/1986 | Patel et al. |
| 4,950,467 A | 8/1990 | Phalangas et al. |
| 5,196,147 A | 3/1993 | Taketani et al. |
| 5,196,446 A | 3/1993 | Levitzki et al. |
| 5,217,999 A | 6/1993 | Levitzki et al. |
| 5,318,939 A | 6/1994 | Laver et al. |
| 5,578,416 A | 11/1996 | Tutt |
| 5,656,655 A | 8/1997 | Spada et al. |
| 5,677,329 A | 10/1997 | Spada et al. |
| 5,700,822 A | 12/1997 | Hirth et al. |
| 5,700,823 A | 12/1997 | Hirth et al. |
| 5,712,395 A | 1/1998 | App et al. |
| 5,763,441 A | 6/1998 | App et al. |
| 5,773,476 A | 6/1998 | Chen et al. |
| 5,789,427 A | 8/1998 | Chen et al. |
| 5,792,771 A | 8/1998 | App et al. |
| 5,849,742 A | 12/1998 | App et al. |
| 5,851,999 A | 12/1998 | Ullrich et al. |
| 5,891,917 A | 4/1999 | Tang et al. |
| 5,932,580 A | 8/1999 | Levitzki et al. |
| 5,935,993 A | 8/1999 | Tang et al. |
| 5,990,193 A | 11/1999 | Russell et al. |

FOREIGN PATENT DOCUMENTS

| | | |
|---|---|---|
| EP | 0 125 866 | 11/1984 |
| EP | 0 235 198 | 9/1987 |
| EP | 0 335 641 | 10/1989 |
| EP | 0 570 594 | 11/1993 |
| EP | 0 614 661 | 9/1994 |
| EP | 0 731 697 | 9/1996 |
| JP | 60-244595 | 12/1985 |
| JP | 2-193954 | 7/1990 |
| JP | 2-254425 | 10/1990 |
| JP | 3-230127 | 10/1991 |
| JP | 3-259126 | 11/1991 |
| JP | 4-36731 | 2/1992 |
| JP | 4-96026 | 3/1992 |
| JP | 4-198924 | 7/1992 |
| JP | 4-214387 | 8/1992 |
| JP | 5-173206 | 7/1993 |
| JP | 6-95186 | 4/1994 |
| JP | 6-186599 | 7/1994 |
| JP | 9-230585 | 9/1997 |
| WO | WO 95/14464 | 6/1995 |
| WO | WO 95/24190 | 9/1995 |
| WO | WO 95/26341 | 10/1995 |
| WO | WO 96/40629 | 12/1996 |
| WO | WO 94/10157 | 5/1999 |
| WO | WO 01/79158 | 10/2001 |

OTHER PUBLICATIONS

Beilstein Institut Zur Foederund Der Chemischen Wissenschaften, Frankfurt Am Main, De; Database–Accession No. 2329569 (BRN), XP002179053 & J. Chem. Soc., vol. 123, 1923, p. 3138.

Abdel–Rahman (1991). "Inverse electron demand Diels–Alder reactions of electron–withdrawing–group–substituted 1,3–butadiene derivatives with enamines. Synthesis of cyclohexene derivatives," *M.A. Sohag Pure Appl. Sci. Bull.* 7:30–40, ACS abstract AN 118:212527 CA only.

Adachi, T. et al. (1999). "A Novel Lyn–Binding Peptide Inhibitor Blocks Eosinophil Differentiation, Survival, and Airway Eosinophilic Inflammation," *Journal of Immunology* 163:939–946.

(List continued on next page.)

*Primary Examiner*—Robert W. Ramsuer
*Assistant Examiner*—Ebenezer Sackey
(74) *Attorney, Agent, or Firm*—Ropes & Gray LLP

(57) ABSTRACT

Novel styrylacrylonitrile compounds which are useful in treating a variety of cell proliferative disorders such as cancer are disclosed. The compounds are of the Formula I:

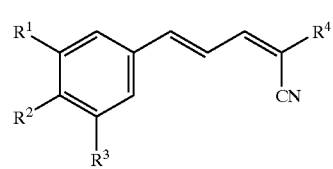

22 Claims, 25 Drawing Sheets

OTHER PUBLICATIONS

Astle, M.J. and Gergel, W.C. "Catalysis with ion exchange resins. Knoevenagel condensations of cyanoacetic acid," *Chemical Abstracts* 51:2641g. (1999).

Balalaie, S. and Nemati, N. (2000). "Ammonium acetate–basic alumina catalyzed Knoevenagel condensation under microwave irradiation under solvent–free condition", *Synthetic Communications* 30(5):869–875.

Bandgar, B.P. et al. (1997). "Condensation of alpha–cyanothioacetamide with aldehydes catalyzed by Envirocat EPZG," *Synthetic Communications* 27(7):1153–1156.

Banerjee PK and Amidon GL. (1985). "Design of prodrugs based on enzymes–substrate specificity," *In Design of Prodrugs*, Bundgaard H, ed. Elsevier: New York, pp. 93–133.

Cabello, J.A. et al. (1984). "Knoevenagel Condensation in the Heterogeneous Phase Using $AiPO_4$–$Al_2O_3$ as a New Catalyst," *Journal of Organic Chemistry* 49(26):5193–5197.

Chen, J.J. and Wang I.J. (1995). "Synthesis and Fluorescence Behaviour of Some 3–Cyano–4–Substituted–6–Pyrenyl–2–Pyridone Derivatives," *Dyes and Pigments*. 27(3):249–259.

Choudary, B.M. et al. (1999). "Knoevenagel and aldol condensations catalysed by a new diamino–functionalized mesoporous material," *Journal of Molecular Catalysis A: Chemical* 142(3):361–365.

Coqueret, Xavier (1999). "Photoreactivity of polymers with dimerizable side–groups: Kinetic analysis for probing morphology and molecular organization," *Macromolecular Chemistry and Physics* 200:1567–1579.

Costisella, B., Gross, H. (1984). "alpha–Substituted phosphonates. 46. 1–Cyanodiene–1–amines and 1–cyanotriene–1–amines via the Horner reaction," *Z. Chem.* 24(10):383–384 (in German) and ACS Abstract AN 103:6414 CA.

Dai, C. et al. (1982). "Structural effect in forked conjugative systems, Bifurcation–type of forked polyenic nitriles, carboxylic acids and esters," *Scientia Sinica. Series B*, Chemical, biological, agricultural, medical & earth sciences / Chung–kuo kʻo hsüeh yüan, chu pan. (Engl. ed.) 25(10):1023–1034.

Database Crossfire Beilstein Online! Beilstein Institut Zur Foederung Der Chemischen Wissenschaften, Frankfurt Am Main, DE; Database–Accession No. 2331300 (BRN), XP002179051.

Database Crossfire Beilstein Online! Beilstein Institut Zur Foederung Der Chemischen Wissenschaften, Frankfurt Am Main, DE; Database–Accession No. 1983526 (BRN), XP002179052.

Database Crossfire Beilstein Online! Beilstein Institut Zur Foederung Der Chemischen Wissenschaften, Frankfurt Am Main, DE; Database–Accession No. 2329569 (BRN), XP002179053.

Database Crossfire Beilstein Online! Beilstein Institut Zur Foederung Der Chemischen Wissenschaften, Frankfurt Am Main, DE; Database–Accession No. 6696684 (BRN), XP002179054.

Database Crossfire Beilstein Online! Beilstein Institut Zur Foederung Der Chemischen Wissenschaften, Frankfurt Am Main, DE; Database–Accession No. 5905971 (BRN), XP002179055.

Database Crossfire Beilstein Online! Beilstein Institut Zur Foederung Der Chemischen Wissenschaften, Frankfurt Am Main, DE; Database–Accession No. 1954179 (BRN), XP002179056.

Database Crossfire Beilstein Online! Beilstein Institut Zur Foederung Der Chemischen Wissenschaften, Frankfurt Am Main, DE; Database–Accession No. 1959697 (BRN), XP002179057.

DeLombaert, S. and Ghosez, L. (1984). "Synthesis and phase–transfer mediated alkylations of 2–Diethylamino–4–Phenylsulfonyl–2–butenenitrile an efficient homoenolate equivalent," *Tetrahedron Letters* 25: 3475–3478.

DeSa, A.J., S.L. and Pitta, I. DaR (1979). "Synthesis and spectroscopic study of ethyl 2–cyano–5–phenyl–2,4–pentadienoate and two of its derivatives," *An. Assoc. Bras Quim.* 30:113–116 (in Portuguese with English abstract) and ACS Abstract AN 96:34120.

Enk, A.H. and Knop, J. (2000). "T–Cell Receptor Mimic Peptides And Their Potential Application In T–Cell Mediated Disease" *Int. Arch Allergy Immunol* 123:275–281.

Eugster, C.H. et al. "New type condensation reactions with isoxazoles–an extension of the Ritter reaction," *Chemical Abstracts* 59:585b.

Fauser A. A. and Messner H. A. (1978). "Granuloerythropoietic Colonies In Human Bone Marrow, Peripheral Blood, And Cord Blood," *Blood*, 52(6), 1243–1248.

Foucaud, A. and Bakouetila, M. (1987). "Facile Epoxidation of Alumina–Supported Electrophilic Alkenes and Montmorillonite–Supported Electrophilic Alkenes with Sodium Hypochlorite," *Synthesis* 9: 854–856.

Freedman, M.H. et al. (1992). "Central Role Of Tumour Necrosis Factor, GM–CSF, and Interleukin 1 in The Pathogenesis Of Juvenile Chronic Myelogenous Leukaemia," *Br J Haematol.* 80(1):40–48.

Freeman, F. (1980). "Properties and Reactions of Ylidenemalononitriles," *Chem. Rev.* 80:329–350.

Frohardt, R. P. et al. "Chemistry of streptimidone. A new antibiotic," *Chemical Abstracts* 54:3192h.

Gazit, A. et al. (1991). "Tyrphostins. 2. Heterocyclic And Alpha–Substituted Benzylidenemalononitrile Tyrphostins As Potent Inhibitors Of EGF Receptor and ErbB2/neu Tyrosine Kinases," *J. Med. Chem.* 34:1896–1907.

Grinsteins, V. and Serina, L. (1963). "Cyanothioacetamide and its derivatives," *Chemical Abstracts* 60:5391h.

Halestrap, A.P. (1975). "The Mitochondrial Pyruvate Carrier. Kinetics and specificity for substrates and inhibitors," *Biochemical Journal* 148(1): 85–96.

Halestrap, A.P. (1976). "The Mechanism of the Inhibition of the Mitochondrial Pyruvate Transporter by alpha–Cyanocinnamate Derivatives," *Biochemical Journal* 156(1):181–183.

Hassan, H.H. et al (1986). "Some reactions of 2–Cinnamylidene and 2–Benzylidene–1,3–Indandione," *Pak. J. Sci. Ind. Res.* 29:105–107.

Ho, Y.W. and Wang, I.J.J. (1995). "Studies on the Synthesis of Some Styryl–3–cyano–2(1H)–pyridine–thiones and Polyfunctionally Substituted 3–Aminothieno[2,3–b]–pyridine Derivatives," *Journal of Heterocyclic Chemistry* 32(3):819–825.

Hu, Weixiao et al (1985). "Differential pulse polaragraphy on bifurcate conjugate systems, I. Homologous progressive change of the peak potential," *Fenzi Kexue Yu Huaxue Yanjiu* 5(1)87–92, ACS Abstract AN 104:5348 CA only.

Ichimura, K. et al. (1987). "Photosensitive Resins Containing p–Dimethylaminobenzylidene Derivatives and Diphenyliodonium Salt as Photoinitiators," *Journal of Applied Polymer Science* 34(8):2747–2756.

Iizawa, T. et al. (1983). "Studies of photopolymer. XX. Synthesis of photosensitive polymers with pendant photosensitive groups and photosensitizer groups," *Kobunshi Ronbunshu* 40:425–432 QD 281 P6 K752 (in Japanese with English abstract) and ACS Abstract AN 99:123029 CA.

Jukhnovskii, I. and Binev, I. (1977). "Infrared Spectra and Structure of Carbaniens–XIV. Isomeric Carbanionic adducts of some substituted cyano–polyenes," *Bulletin des Societes Chines Belges* 86(10):793–798.

Kantam, M.L. et al. (1998). "Aldol and Knoevenagel condensations catalysed by modified Mg–Al hydrotalcite: a solid base as catalyst useful in synthetic organic chemistry," *Chemical Communications* (Cambridge England) 9:1033–1034.

Kasyapa, C. S. et al. (1999). "Regulation of IL–15–Simulated TNF–alpha Production by Rolipram," *Journal of Immunology* 163:2836–2843.

Konwar, D. et al. (1998). "Organic Synthesis with Anion-exchange Resins: Reaction of Imines with Active Methylene Compounds," *Journal of Chemical Research Synopsis* 6:342–343.

Krishan, K. and Singh, N. (1974). "Reactions of Open-Chain Conjugated Nitrones with Active Methylene Compounds," *J. Indian Chem. Soc.* 51(9): 802–804.

Kryshtal, G.V. et al. (1979). "Phase–Transfer Catalysis of the Michael Addition to alpha,beta–Unsaturated Aldehydes," *Synthesis* 2:107–109.

Kryshtal, G.V. et al. (1980). "New possibilities for the synthesis of polyfunctional cyclopropanes under interphase catalysis conditions in a liquid–solid phase system," *Izvestiia Akademii nauk SSSR Seriia khimicheskaia* 10:2420–2423 (in Russian) and ACS Abstract AN 94:46812 CA.

Kurkovskaja, L.N. et al. (1995). "$^1$H and $^{13}$C NMR Spectrum–Structure correlations for a series of polyene compounds," *Zhurnal Strukturnoi Khimii*. English *Journal of Structural Chemistry* 36(4): 638–642.

Lechat, J.R. et al. (1981). "Ethyl 2–Cyano–5–phenyl–(2E, 4E)–pentadienoate," *Acta Crystallographica Section B: Structural Science* B37(7):1470–1471.

Li, J–T et al. (1999). "Synthesis of ethyl alpha–cyanocinnamates under ultrasound irradiation," *Ultrasonics Sonochemistry* 6(4):199–201.

Liang, D. et al. (1981). "Structural effect in cross conjugative systems. IV. Properties of alpha–carboxylphenylpolyenic cyanides and the quantum chemical," *Fenzi Kexue Xuebao* 1:17–30 (in Chinese with English abstract) and ACS Abstract AN 96:180289 CA.

Lin, T. et al. (1993). "Transition metal polyhydrides–catalyzed addition of activated nitriles to aldehydes and ketones via Knoevenagel condensation," *Journal of Organometallic Chemistry* 448(1–2): 215–218.

Martelli, J. and Carrie, R. (1977). "Reaction of cinnamylidenemalonic esters or cinnamylidene cyanoacetic esters and the corresponding malononitriles with diazomethane; thermolysis of the corresponding pyrazolines," *Bulletin de la Societe Chimique de France* 11–12, Pt. 2: 1182–1186 (in French) and ACS Abstract AN 89:43222 CA.

Martelli, J. et al. (1973). "Stereospecific methylation of cinnamylidenecyanoacetic acid esters and cinnamylidenemalononitrile using diazomethane," *Comptes Rendus de l'Academie des Sciences Serie IIc:Chemie (C.R Acad. Sci. Ser. C.)* 276:523–525 (in French) and ACS Abstract AN 78:135492 CA.

Martelli, J. et al. (1978). "Orientation and primary site in the addition of diazomethane on some substituted butadienes. Theoretical interpretation," *Nouv. J. Chim.* 2:609–613 and ACS Abstract AN 90:120818 CA.

Matsuoka, M. et al. (1990). "Cyanovinylheteroaromatics for Organic Nonlinear Optics," *Molecular Crystals and Liquid Crystals Science and Technology Section A* 182A:71–79.

Messner H. A. and Fauser, A. A. (1980). "Culture Studies Of Human Pluripotent Hemopoietic Progenitors," *Blut*, 41(5): 327–333.

Minami, T. et al. (1985). "Cycloaddition of Diazomethane to Butadienylphosphonates. A New Approach to Functionalized Pentadienylphosphonates and Pyrazoles," *Chem. Lett.* 1985 8:1099–1102.

Minami, T. et al. (1983). "Synthesis of Butadienylphosphonates containing electronegative substituents and their synthetic applications to functionalized cyclopentenylphosphonates," *Tetrahedron Lett.* 24(8):767–770.

Mohan, S. and Sandhu, J.S. (1971). "Addition of Diazomethane on Strongly Electrophillic Olefins," *Journal of the Indian Society* 48(3):305–306.

Nesterov, V.N. et al. (2000). "trans,trans–2–Cyano–5–(4–methoxy–phenyl)penta–2,4–dienethioamide," *Acta Crystallographica Section C: Crystal Structure Communications* C56(1):88–89.

Nguyen, K.S. et al. (1974). "Sulfur heterocyclic compounds. LXIX. Synthesis and structure of variously substituted 2–amino–5–thioaroylthiophenes," *Bulletin de la Societe Chimique de France* 3–4 Pt.2:471–474 (in French) and ACS Abstract AN 81:63423 CA.

Ooms, P. et al. (1976). "Chemistry of Tetra–alhoxyethenes. Part VII. Thermal [2+2] Cycloadditions with 1–Cyanobutadienes" *Journal of the Chemical Society*, Perkin Transactions 1 14:1538–1543.

Piskov, V. B. (1967). "Tetracycline analogs. I. General preparation of beta–aryl–beta1–carboxymethylpimelic acids" *Zhurnal Organicheskoi Khimii* 3(2):416–419 (in Russian) and ACS Abstract AN 66:115418 CA.

Popp, F. and Catala, A. (1961). "Synthesis of 3–hydrozypyridines. II. The preparation of unsaturated cyano esters and their reaction with diazo–methane" *J. Org. Chem.* 26(8):2738–2740.

Prajapati D. and Sandhu, J.S. (1992). "Bismuth(III)chloride as a New Catalyst for Knoevenagel Condensation in the Absence of Solvent" *Chemistry Letters.* 10: 1945–1946.

Prajapati, D. and Sandhu, J.S. (1993). "Lithium bromide as a new catalyst for carbon–carbon bond formation in the solid state" *J. Chem. Soc., Perkin Transactions* 1:959–960.

Prajapati, D. et al. (1993). "Cadmium Iodide as a New Catalyst for Knoevenagel Condensations," *J. Chem. Soc., Perkin Transactions* 1: 739–740.

Puccetti, G., Bott, S.G., (1998). "Efficient two–photon–induced fluorescence in a new organic crystal" *J. Opt. Soc. Am. B* 15(2):789–901.

Pudovik, AN, Yastrebova, G.E., Nikitina, V.I., (1968). "Condensations of (cyanomethyl)Phosphonic Esters" *Zh. Obshch. Khim.* 38(2):301–305.

Rao, P.S. and Venkataratnam, R.V (1991). "Zinc Chloride as a new catalyst for Knoevenagel condensation" *Tetrahedron Letters* 32:5821–5822.

Rao, Y.V. and Choudary, B.M. (1991), "Knoevenagel condensation catalysed by new montmorillonitesilylpropylethylenediamine" *Synthetic Communications* 21(10–11): 1163–1166.

Roucoux, C. et al. (1981). "Photochemistry of Polymeric Systems. III. Photocrosslinking of Polymers and Copolymers Including Cyanocinnamylydene–Pyridinium Groups" *Journal of Applied Polymer Science* 26(4):1221–1232.

Row, T.N. et al. (1983). "Reversible Photodimerization of Phenylbutadienes in the Solid State" *Tetrahedron Letters* 24:3263–3266.

Ruckert, R. et al. (2000). "Inhibition of Keratinocyte Apoptosis by IL–15: A New Parameter in the Pathegenosis of Psoriasis?" *Journal of Immunology* 165:2240–2250.

Sabitha, G. et al. (1998). "LiCl Catalyzed Knoevenagel Condensation: Comparative Study of Conventional Method vs. Microwave Irradiation" *Chemistry Letters* 8:773–774.

Sebti, S. et al. (1994). "Natural phosphate and trisodium phosphate: novel solid catalysis for the Knoevenagel condensation in heterogeneous media" *Tetrahedron Letters* 35:9399–9400 (in French) and ACS Abstract AN 122:80462 CA.

Shen, Y. and Yang, B. (1989). "Synthesis of alpha,beta–unsaturated cyanoesters promoted by tri–n–butylarsine" *Synthetic Communications* 19(17):3069–3075.

Singh, N. and Sandhu, J.S. (1969). "Studies in Conjugated Imines: Addition of Active Methylene Compounds" *Journal of the Indian Chemical Society* 46(8):751–753.

Swamy H. R. et al. (1982). "Reversible Photodimerization of Some Butadiene Derivatives in Solid State" *Indian Journal of Chemistry* Section B: Organic Chemistry including Medicinal Chemistry 21B(2):79–82.

Taketani, Y. et al. (1992). "Preparation of novel non–linear organic materials" *Nonlinear Opt. Proc. Toyota Conf. Nonlinear Opt. Mater* $5^{th}$ 249–254 and ACS Abstract AN 117:222489 CA.

Tanaka, H. and Sato, Y. (1972). "Photosensitivity of poly vinyl esters of substituted cinnamylideneacetic acids" *J. Polym. Sci.* part A–1 10(11) 3279–87 and ACS Abstract AN 78:58922 CA.

Texier–Boullet and Foucand, A. (1982). "Knoevenagel Condensation Catalysed by Aluminum Oxide" *Tetrahedron Letters* 23:4927–4928.

Todorova, G., Chen, J., (2000). "New NLO chromophores on 2–amino–1,1–3–tricyano–1–propene acceptor" *Polym. Mater. Sci. Eng.* 83:256–257.

Williams, J.B. et al. (1996), "Use of Liquid Matrices for Matrix–Assisted Laser Desorption Ionization of Polyglycols and Poly(dimethylsiloxanes)" *Macromolecules* 29(25): 8144–8150.

Wittig, G. and Kethur, R "Ein neuer Weg zum Aufbau von Polyyenketten" *Berichte der Deutschen Chemischen Gesellschaft* 69(1936):2078–2081 (in German).

Wizinger, R. and Sontag, H. (1955) "Vinylene "shift" in asymmetric phenylpolyenes" *Chem. Abstracts* 51:5739I, 5740a–I, 5741a and ACS abstract AN 51:29795 CA.

Yasuda, Heinosuke; Sakao, Toshihisa; Yamadi Yoichi (1995). "The Knoevenagel condensation between aromatic aldehydes and ethyl cyanoacetate catalyzed by KF–betaine catalyst" Utsunomiya Daigaku Kyoikugakubu Kiyo, Dai–2–bu 45:33–41 (in Japanese with English Abstract) and ACS Abstract AN 124:29360 CA.

Zhong, Q. et al. (1991). "Catalytic synthesis of alpha, beta–unsaturated nitriles, cyanoesters and cyanoamides by organotellurium oxide" Yingyong Huaxue *Chinese Journal of Applied Chemistry* 8(5):17–20 (in Chinese) and ACS Abstract AN 1992:83329 CAPLUS.

COMPOUNDS FOR MODULATING CELL PROLIFERATION

CROSS REFERENCE TO RELATED APPLICATIONS

This application claims the priority benefit of provisional application U.S. Ser. No. 60/196,936, filed Apr. 13, 2000, the contents of which are incorporated herein by reference in their entirety.

FIELD OF THE INVENTION

This invention relates to novel compounds which are useful for treating a variety of cell proliferative disorders such as cancer.

BACKGROUND OF THE INVENTION

A wide range of growth factors coordinate cell proliferation and differentiation. Malignant cells arise as a result of a stepwise progression of events that include the unregulated expression of growth factors or components of their signaling pathways. Tyrosine phosphorylation events initiated by receptor, cytoplasmic and nuclear kinases and regulated by phosphatases are central to these processes. Mutation, hyper-activation, translocation and overexpression of protein tyrosine kinases are all associated with tumorigenesis. In addition to increasing proliferative rates and immortalizing cells, overexpression of tyrosine kinases can lead to morphological transformation and cause anchorage independence, contributing to the promotion of migratory ability and possibly the induction of metastases.

Certain compounds with structures based upon mimicry of ATP or phosphotyrosine have been shown to be effective kinase inhibitors. Those based upon phosphotyrosine have been demonstrated to be the more specific tyrosine kinase inhibitors. Because of their ability to inhibit tyrosine phosphorylation, these compounds may alter cell responses to growth factors or other process driven by tyrosine kinase activity, including unregulated growth as the result of tyrosine kinase overexpression, mutation, or translocation. Inhibition of tyrosine kinases occupying a central role in proliferative signaling pathways, or in pathways regulating cell cytoskeletal structure, even temporary or incomplete inhibition, may be sufficient to switch a cancerous cell from a proliferative cycle into programmed cell death, or apoptosis. Death by apoptosis is most often observed upon effective treatment with tyrosine kinase inhibitors.

Selective inhibition of specific tyrosine kinases offers a method of targeting cancerous cell growth with a high degree of specificity and minimal toxicity to normally growing cells and tissues. Thus, specific inhibitors of tyrosine kinases have great potential as clinical anti-cancer treatments. A number of small molecules which act as tyrosine kinase inhibitors have been identified. For example, certain phenyl acrylonitrile compounds have been described as tyrosine kinase inhibitors, effective to inhibit cell proliferation (see for example, U.S. Pat. Nos. 5,891,917, 5,217,999, 5,773,476, 5,935,993, 5,656,655, 5,677,329 and 5,789,427).

Inhibition of tyrosine kinases offers one mechanism by which cell proliferation can be inhibited. One of skill in the art will appreciate that other mechanisms of inhibition may also be involved.

There is a need in the art to identify compounds that inhibit cell proliferation.

SUMMARY OF THE INVENTION

A number of novel compounds have now been identified that inhibit abnormal cell proliferation, for example cancer cell growth. The compounds do not inhibit the growth of normal cells.

Accordingly, the present invention includes compounds of Formula I and salts, solvates and hydrates thereof:

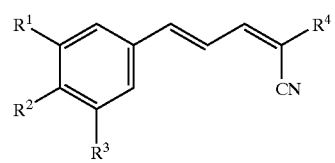

I wherein
$R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl), $NO_2$, halo and $CH_2$—S—$(CH_2)_n$Ar;

$R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}$alkyl$)_2$, and $C(NH_2)$=$C(CN)_2$;

X is selected from O, S, NH and N—$C_{1-6}$alkyl;

$R^5$ is selected from the group consisting of $NH_2$, OH, $NH(CH_2)_p$Ar, $NH(CH_2)_p$OH, $(CH_2)_pOC_{1-6}$alkyl, $C_{1-6}$alkyl, $C_{1-6}$alkoxy, $NHNH_2$, NHC(O)$NH_2$, NHC(O)$C_{1-6}$alkoxy, N-morpholino and N-pyrrolidino;

Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;

n is 0 to 4; and p is 1–4.

The present invention further includes compounds of Formula II and salts, solvates and hydrates thereof:

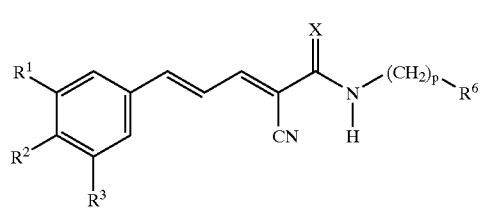

II wherein
$R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl), $NO_2$, halo and $CH_2$—S—$(CH_2)_n$Ar;

Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;

R⁶ is selected from the group consisting of Ar, OH and OC$_{1-6}$alkyl;

X is selected from O and S;

n is 0–4; and p is 1–4.

The present invention also provides compounds of Formula III and salts, solvates and hydrates thereof:

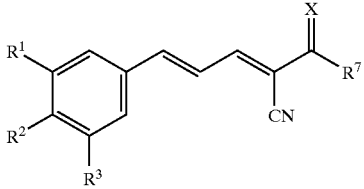

III wherein
R¹ and R² are each independently selected from the group consisting of H, OH, C$_{1-6}$alkyl, C$_{1-6}$alkoxy, NH$_2$, NH—C$_{1-6}$alkyl, N(C$_{1-6}$alkyl)(C$_{1-6}$alkyl), SH, S—C$_{1-6}$alkyl, O—Si(C$_{1-6}$alkyl)(C$_{1-6}$alkyl)(C$_{1-6}$alkyl), NO$_2$, CF$_3$, OCF$_3$ and halo;

R³ is selected from the group consisting of H, OH, C$_{1-6}$alkyl, C$_{1-6}$alkoxy, NH$_2$, NH—C$_{1-6}$alkyl, N(C$_{1-6}$alkyl)(C$_{1-6}$alkyl), SH, S—C$_{1-6}$alkyl, O—Si(C$_{1-6}$alkyl)(C$_{1-6}$alkyl)(C$_{1-6}$alkyl), NO$_2$, halo and CH$_2$—S—(CH$_2$)$_n$Ar;

Ar is an aromatic or heteroaromatic group, unsubstituted or substituted with 1–4 substituents, independently selected from the group consisting of OH, C$_{1-6}$alkyl, C$_{1-6}$alkoxy, NH$_2$, NH—C$_{1-6}$alkyl, N(C$_{1-6}$alkyl)(C$_{1-6}$alkyl), SH, S—C$_{1-6}$alkyl, NO$_2$, CF$_3$, OCF$_3$ and halo;

R⁷ is selected from the group consisting of OH, NH$_2$ and OC$_{1-6}$alkyl;

X is selected from O and S; and n is 0–4.

According to another aspect of the present invention, there is provided a pharmaceutical composition comprising a compound of the invention and a pharmaceutically acceptable carrier or diluent.

In accordance with a further aspect of the present invention, there is provided a method for modulating cell proliferation, preferably inhibiting cell proliferation comprising administering an effective amount of a compound of the invention to a cell or animal in need thereof. The invention also includes a use of a compound of the invention to modulate cell proliferation, preferably inhibit cell proliferation. The invention further includes a use of a compound of the invention to prepare a medicament to modulate cell proliferation, preferably inhibit cell proliferation.

In a preferred embodiment the present invention provides a method of inhibiting the proliferation of a cancer cell comprising administering an effective amount of a compound of the invention to a cell or animal in need thereof. The cancer cell treated may be any type of cancer including a leukemia, a lymphoma, myeloma, metastatic carcinoma, sarcoma or any other malignant transformation or any other malignancy. The invention also includes a use of a compound of the invention to modulate cancer cell proliferation, preferably inhibit cancer cell proliferation. The invention further includes a use of a compound of the invention to prepare a medicament to modulate cancer cell proliferation, preferably inhibit cancer cell proliferation.

In another aspect, the invention provides a method of modulating tyrosine kinase activity in a cell by administering an effective amount of a compound of the invention. In a further aspect, the invention provides a method of inhibiting tyrosine kinase activity in a cell by administering an effective amount of a compound of the invention. The present invention also provides a use of a compound of the invention to modulate, preferably inhibit, tyrosine kinase activity. The present invention further provides a use of a compound of the invention to prepare a medicament to modulate tyrosine kinase activity, preferably inhibit tyrosine kinase activity. It is appreciated that the inhibition of cell growth by the compounds of the invention may be effected by other mechanisms.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE PREFERRED EMBODIMENTS

Figure 1:
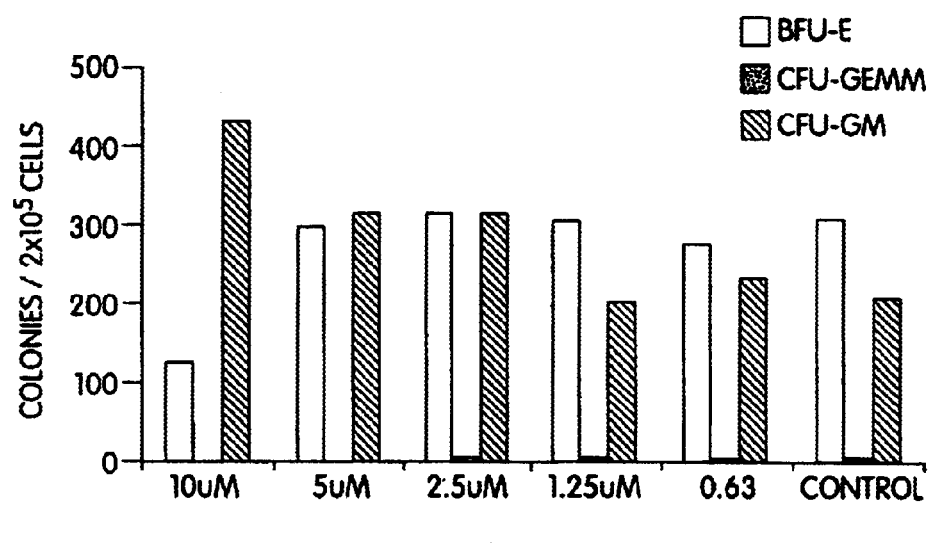
FIG. 1 is a bar graph showing the effect of CR4 upon normal bone marrow differentiation in culture.

Throughout this application, various publications, patents, and published patent applications are referred to by an identifying citation. The disclosures of the publications, patents, and published patent applications referenced in this application are hereby incorporated by reference into the present disclosure in their entirety.

I. Definitions

The term "$C_{1-6}$alkyl" as used herein means, unless otherwise stated, straight and/or branched chain alkyl radicals containing from one to six carbon atoms and includes methyl, ethyl, propyl, isopropyl, t-butyl and the like.

The term "$C_{1-6}$alkoxy" as used herein means, unless otherwise stated, straight and/or branched chain alkoxy radicals containing from one to six carbon atoms and includes methoxy, ethoxy, propyoxyl, isopropyloxy, t-butoxy and the like.

The term "$C_{1-4}$alkyl" as used herein means, unless otherwise stated, straight and/or branched chain alkyl radicals containing from one to four carbon atoms and includes methyl, ethyl, propyl, isopropyl, t-butyl and the like.

The term "$C_{1-4}$alkoxy" as used herein means, unless otherwise stated, straight and/or branched chain alkoxy radicals containing from one to four carbon atoms and includes methoxy, ethoxy, propyoxyl, isopropyloxy, t-butoxy and the like.

The term "Ar" as used herein, means an unsubstituted or substituted aryl and/or heteroaryl group which, in the case of heteroaryl, may contain up to two heteroatoms, wherein the constituents are independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like.

The term "halo" as used herein means halogen and includes chloro, flouro, bromo, iodo and the like.

The term "pharmaceutically acceptable salt" means an acid addition salt or a basic addition salt which is suitable for or compatible with the treatment of patients.

The term "compound of the invention" as used herein includes any compound of the Formula I, II or III as defined herein (including all salts, solvates or hydrates thereof) as well as a specific compound designated herein as CR1, CR2, CR3, CR4, CR5, CR8, CR9, CR11, CR12, CR13, CR14, CR15, CR16, CR17, CR18, CR19, CR20, CR21, CR24, CR27, CR28, and CR29 (including all salts, solvates or hydrates thereof).

The term "pharmaceutically acceptable acid addition salt" as used herein means any non-toxic organic or inorganic salt of any base compounds represented by Formulae I, II and/or III or any of their intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formulae I, II and/or III are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds of Formulae I, II and/or III for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formulae I, II and/or III or any of their intermediates. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art.

The term "solvate" as used herein means a compound of Formulae I, II and/or III, or a pharmaceutically acceptable salt of a compound of Formulae I, II and/or III, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that inhibits cancer cell proliferation, an effective amount of an agent is, for example, an amount sufficient to achieve such a reduction in cancer cell proliferation as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as cell proliferation) as well as the enhancement of a function or activity.

To "inhibit" or "suppress" or "reduce" a function or activity, such as cancer cell proliferation, is to reduce the function or activity when compared to otherwise same conditions except for a condition or parameter of interest, or alternatively, as compared to another conditions.

The term "animal" as used herein includes all members of the animal kingdom including human. The animal is preferably a human The term "a cell" as used herein includes a plurality of cells. Administering a compound to a cell includes in vivo, ex vivo and in vitro treatment.

The term "cancer cells" as used herein includes all forms of cancer or neoplastic disease.

II. Compounds of the Invention

Novel compounds which are useful in modulating cell proliferation were prepared. As such the compounds are useful in treating cell proliferative diseases such as cancer.

Accordingly, the present invention provides compounds of Formula I, and salts, solvates or hydrates thereof.

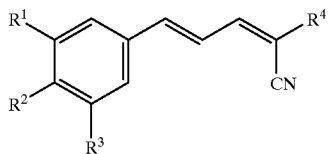

I wherein $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;

$R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}alkyl)_2$, and $C(NH_2)=C(CN)_2$;

X is selected from O, S, NH and N—$C_{1-6}$alkyl;

$R^5$ is selected from the group consisting of $NH_2$, OH, $NH(CH_2)_p$Ar, $NH(CH_2)_p$OH, $(CH_2)_pOC_{1-6}$alkyl, $C_{1-6}$alkyl, $C_{1-6}$alkoxy, $NHNH_2$, NHC(O)$NH_2$, NHC(O)$C_{1-6}$alkoxy, N-morpholino and N-pyrrolidino; and Ar is an aromatic or heteroaromatic group, unsubstituted or substituted with 1–4 substituents independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;

n is 0 to 4;

m is 1 to 4; and p is 1–4.

In embodiments of the invention, compounds of Formula I are those in which $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo. In preferred embodiments, $R^1$ and $R^2$ are each independently selected from the group consisting of H, OH, $C_{1-4}$alkyl, $C_{1-4}$alkoxy, $NH_2$, NH—$C_{1-4}$alkyl, SH, S—$C_{1-4}$alkyl, O—Si($C_{1-4}$alkyl)($C_{1-4}$alkyl)($C_{1-4}$alkyl), $NO_2$, $CF_3$, $OCF_3$ and halo. In more perferred embodiments, $R^1$ and $R^2$ are each independently selected from the group consisting of H, OH, $OCH_3$, O—Si($CH_3)_2$($^t$Bu), S—Me, SH and $NO_2$. In the most preferred embodiment of the present invention $R^1$ and $R^2$ are both OH or $OCH_3$ or $R^1$ is $OCH_3$ and $R^2$ is OH.

In further embodiments of the present invention, the compounds of Formula I include those in which $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar (where n is 0–4). In preferred embodiments, $R^3$ is selected from the group consisting of H, OH, $C_{1-4}$alkyl, $C_{1-4}$alkoxy, $NH_2$, NH—$C_{1-4}$alkyl, N($C_{1-4}$alkyl)($C_{1-4}$alkyl), SH, S—$C_{1-4}$alkyl, $NO_2$ and halo. In a more preferred embodiment, $R^3$ is selected from the group consisting of H, OH, $OCH_3$, SH, SMe, $NO_2$ and halo. In the most preferred embodment, $R^3$ is selected from the group consisting of H, OH and $OCH_3$.

Embodiments of the invention include compounds of Formula I wherein $R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}alkyl)_2$, and $C(NH_2)=C(CN)_2$ (where m is 1–4). In preferred embodiments, $R^4$ is selected from the group consisting of $C(X)R^5$ and $C(NH_2)=C(CN)_2$. More preferably, $R^4$ is $C(X)R^5$. When $R^4$ is $C(X)R^5$, embodiments of the invention include compounds where X is selected from O, S, NH and N—$C_{1-6}$alkyl and $R^5$ is selected from the group consisting of $NH_2$, OH, $NH(CH_2)_p$Ar, $NH(CH_2)_p$OH, $(CH_2)_pOC_{1-6}$alkyl, $C_{1-6}$alkyl, $C_{1-6}$alkoxy, $NHNH_2$, NHC(O)$NH_2$, NHC(O)$C_{1-6}$alkoxy, N-morpholino and N-pyrrolidino (where p is 1–4). In preferred embodiments, X is O or S and $R^5$ is selected from the group consisting of $NH_2$, OH, $NH(CH_2)_p$Ar, $(CH_2)_p$OH and $C_{1-4}$alkoxy, (where p is 1–3). Most preferred, are compounds of Formula I wherein X is O and $R^5$ is selected from the group consisting of $NH_2$, OH, $NH(CH_2)_p$Ar, $NH(CH_2)_p$OH and $OCH_3$, (where p is 1–2).

The present invention includes compounds of Formula I wherein the term "Ar" means an unsubstituted or substituted aryl and/or heteroaryl group which, in be case of heteroaryl, may contain up to two heteroatoms, wherein the optional substituents are independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like. In embodiments of the present invention, Ar is an unsubstituted phenyl group or a phenyl group substituted with 1–4 substituents optionally selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo. In preferred embodiments, Ar is an unsubstituted phenyl group or phenyl group substituted with 1–2 substituents optionally selected from the group consisting of OH, $C_{1-4}$alkyl, $C_{1-4}$alkoxy, $NH_2$, NH—$C_{1-4}$alkyl, N($C_{1-4}$alkyl)($C_{1-4}$alkyl), SH, S—$C_{1-4}$alkyl, $NO_2$, $OF_3$, $OCF_3$ and halo. In more preferred embodiments, Ar is an unsubstituted phenyl group or phenyl group substituted with 1–2 substituents optionally selected from the group consisting of OH, $OCH_3$, $NH_2$, $NHCH_3$, $N(CH_3)_2$, SH, $SCH_3$, $CF_3$, $OCF_3$ and halo. In the most preferred embodiment, Ar is selected from the group consisting of phenyl and 3,4-dihydroxyphenyl.

The present invention further includes compounds of Formula II and salts, solvates and hydrates thereof:

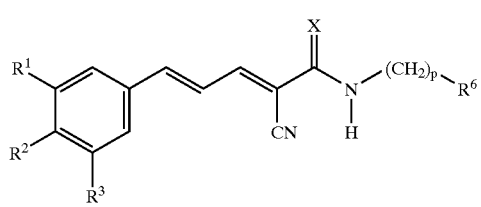

II wherein
$R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;

Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, $R^6$ is selected from the group consisting of Ar, OH and $OC_{1-6}$alkyl;

X is selected from O and S;

n is 0–4; and p is 1–4.

In embodiments of the invention, compounds of Formula II are those in which $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo. In preferred embodiments, $R^1$ and $R^2$ are each independently selected from the group consisting of H, OH, $C_{1-4}$alkyl, $C_{1-4}$alkoxy, $NH_2$, NH—$C_{1-4}$alkyl, SH, S—$C_{1-4}$alkyl, O—Si($C_{1-4}$alkyl)($C_{1-4}$alkyl)($C_{1-4}$alkyl), $NO_2$, $CF_3$, $OCF_3$ and halo. In more perferred embodiments, $R^1$ and $R^2$ are each independently selected from the group consisting of H, OH, $OCH_3$, O—Si($CH_3$)$_2$($^tBu$), S—Me, SH and $NO_2$. In the most preferred embodiment of the present invention $R^1$ and $R^2$ are both OH or $OCH_3$ or $R^1$ is $OCH_3$ and $R^2$ is OH.

In further embodiments of the present invention, the compounds of Formula II include those in which $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($O_{1-6}$alkyl)($C_{1-6}$alkyl)($C_{1-6}$alkyl), $NO_2$, halo and $CH_2$—S—$(CH_2)_n$Ar (where n is 0–4). In preferred embodiments, $R^3$ is selected from the group consisting of H, OH, $C_{1-4}$alkyl, $C_{1-4}$alkoxy, $NH_2$, NH—$C_{1-4}$ alkyl, N($C_{1-4}$alkyl)($C_{1-4}$alkyl), SH, S—$C_{1-4}$alkyl, $NO_2$ and halo. In a more preferred embodiment, $R^3$ is selected from the group consisting of H, OH, $OCH_3$, SH, SMe, $NO_2$ and halo. In the most preferred embodment, $R^3$ is selected from the group consisting of H, OH and $OCH_3$.

The present invention further includes compounds of Formula II wherein the term "Ar" means an unsubstituted or substituted aryl and heteroaryl group which, in the case of heteroaryl, may contain up to two heteroatoms, wherein the optional substituents are independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like. In embodiments of the present invention, Ar is an unsubstituted phenyl group or a phenyt group substituted with 1–4 substituents optionally selected from the group consisting of OH, $C_{1-6}$alkyl, $C_{1-6}$alkoxy, $NH_2$, NH—$C_{1-6}$ alkyl, N($C_{1-6}$alkyl)($C_{1-6}$alkyl), SH, S—$C_{1-6}$alkyl, $NO_2$, $CF_3$, $OCF_3$ and halo. In preferred embodiments, Ar is an unsubstituted phenyl group or phenyl group substituted with 1–2 substituents optionally selected from the group consisting of OH, $C_{1-4}$alkyl, $C_{1-4}$alkoxy, $NH_2$, NH—$C_{1-4}$alkyl, N($CO_{1-4}$alkyl)($C_{1-4}$alkyl), SH, S—$C_{1-4}$alkyl, $NO_2$, $CF_3$, $OCF_3$ and halo. In more preferred embodiments, Ar is an unsubstituted phenyl group or phenyl group substituted with 1–2 substituents optionally selected from the group consisting of OH, $OCH_3$, $NH_2$, $NHCH_3$, $N(CH_3)_2$, SH, $SCH_3$, $CF_3$, $OCF_3$ and halo. In the most preferred embodiment, Ar is selected from the group consisting of phenyl and 3,4-dihydroxyphenyl.

The compounds of Formula II, include those in which $R^6$ is selected from the group consisting of Ar, OH and $OC_{1-6}$ alkyl and p is 1–4. In preferred embodiments, $R^6$ is selected from the group consisting of Ar and OH and p is 1–2. Most preferably, when $R^6$ is Ar, p is 1 and when $R^6$ is OH, p is 2. Where $R^6$ is Ar, Ar means an unsubstituted or substituted aryl and/or heteroaryl group which, in the case of heteroaryl, may contain up to two heteroatoms, wherein the optional substituents are independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like. In embodiments of the present invention, Ar is an unsubstituted phenyl group or a phenyl group substituted with 1–4 substituents optionally selected from the group consisting of OH, $C_{1-6}$alkyl, $C_{1-6}$alkoxy, $NH_2$, NH—$C_{1-6}$ alkyl, N($C_{1-6}$alkyl)($C_{1-6}$alkyl), SH, S—$C_{1-6}$alkyl, $NO_2$, $CF_3$, $OCF_3$ and halo. In preferred embodiments, Ar is an unsubstituted phenyl group or phenyl group substituted with 1–2 substituents optionally selected from the group consisting of OH, $C_{1-4}$alkyl, $C_{1-4}$alkoxy, $NH_2$, NH—$C_{1-4}$alkyl, N($C_{1-4}$alkyl)($C_{1-4}$alkyl), SH, S—$C_{1-4}$alkyl, $NO_2$, $CF_3$, $OCF_3$ and halo. In more preferred embodiments, Ar is an unsubstituted phenyl group or phenyl group substituted with 1–2 substituents optionally selected from the group consisting of OH, $OCH_3$, $NH_2$, $NHCH_3$, $N(CH_3)_2$, SH, $SCH_3$, $CF_3$, $OCF_3$ and halo. In the most preferred embodiment, Ar is selected from the group consisting of phenyl and 3,4-dihydroxyphenyl.

Compounds of Formula II, further include those in which X is selected from O and S. In preferred embodiments, X is O.

The present invention also provides a compound of Formula III and salts, solvates and hydrates thereof:

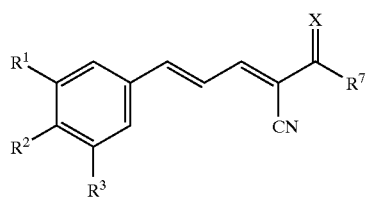

wherein $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;

Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;

$R^7$ is selected from the group consisting of OH, $NH_2$ and $OC_{1-6}$alkyl;

X is selected from O and S, and n is 0–4.

In embodiments of the invention, compounds of Formula III are those in which $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo. In preferred embodiments, $R^1$ and $R^2$ are each independently selected from the group consisting of H, OH, $C_{1-4}$alkyl, $C_{1-4}$alkoxy, $NH_2$, NH—$C_{1-4}$alkyl, SH, S—$C_{1-4}$alkyl, O—Si($C_{1-4}$alkyl)($C_{1-4}$alkyl)($C_{1-4}$alkyl), $NO_2$, $CF_3$, $OCF_3$ and halo. In more perferred embodiments, $R^1$ and $R^2$ are each independently selected from the group consisting of H, OH, $OCH_3$, O—Si($CH_3$)$_2$($^t$Bu), S—Me, SH and $NO_2$. In the most preferred embodiment of the present invention $R^1$ and $R^2$ are both OH or $OCH_3$ or $R^1$ is $OCH_3$ and $R^2$ is OH.

In further embodiments of the present invention, the compounds of Formula III include those in which $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar (where n is 0–4). In preferred embodiments, $R^3$ is selected from the group consisting of H, OH, $C_{1-4}$alkyl, $C_{1-4}$alkoxy, $NH_2$, NH—$C_{1-4}$alkyl, N($C_{1-4}$alkyl)($C_{1-4}$alkyl), SH, S—$C_{1-4}$alkyl, $NO_2$ and halo. In a more preferred embodiment, $R^3$ is selected from the group consisting of H, OH, $OCH_3$, SH, SMe, $NO_2$ and halo. In the most preferred embodiment, $R^3$ is selected from the group consisting of H, OH and $OCH_3$.

The present invention further includes compounds of Formula III wherein the term "Ar" means an unsubstituted or substituted aryl and/or heteroaryl group which, in the case of heteroaryl, may contain up to two heteroatoms, wherein the optional substituents are independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo, and includes unsubstituted or substituted phenyl, furyl, thienyl, indolyl, naphthyl, quinolyl and the like. In embodiments of the present invention, Ar is an unsubstituted phenyl group or a phenyl group substituted with 1–4 substituents optionally selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo. In preferred embodiments, Ar is an unsubstituted phenyl group or phenyl group substituted with 1–2 substituents optionally selected from the group consisting of OH, $C_{1-4}$alkyl, $C_{1-4}$alkoxy, $NH_2$, NH—$C_{1-4}$alkyl, N($C_{1-4}$alkyl)($C_{1-4}$alkyl), SH, S—$C_{1-4}$alkyl, $NO_2$, $CF_3$, $OCF_3$ and halo. In more preferred embodiments, Ar is an unsubstituted phenyl group or phenyl group substituted with 1–2 substituents optionally selected from the group consisting of OH, $OCH_3$, $NH_2$, $NHCH_3$, $N(CH_3)_2$, SH, $SCH_3$, $CF_3$, $OCF_3$ and halo. In the most preferred embodiment, Ar is selected from the group consisting of phenyl and 3,4-dihydroxyphenyl.

Compounds of Formula III further include those in which $R^7$ is selected from the group consisting of OH, $NH_2$ and $OC_{1-6}$alkyl. In preferred embodiments, $R^7$ is selected from the group consisting of OH and $NH_2$.

Compounds of Formula III, further include those in which X is selected from O and S. In preferred embodiments, X is O.

In specific embodiments of the present invention, the compounds of the invention include:

(E,E)-2-(benzylaminocarbonyl)-3-styrylacrylonitrile (CR1);

(E,E)-2-(benzylaminocarbonyl)-3-(3,4-dimethoxystyryl) acrylonitrile (CR2);

(E,E)-2-(benzylaminocarbonyl)-3-(3,5-dimethoxy-4-hydroxystyryl)acrylonitrile (CR3);

(E,E)-2-(benzylaminocarbonyl)-3-(3,4-dihydroxystyryl) acrylonitrile (CR4);

(E,E)-2-(phenylethylaminocarbonyl)-3-(3,4-dimethoxystyryl)acrylonitrile (CR5);

(E,E)-2-(phenylethylaminocarbonyl)-3-(3,5-dimethoxy-4-hydroxystyryl)acrylonitrile (CR8);

(E,E)-2-(phenylpropylaminocarbonyl)-3-(3,5-dimethoxy-4-hydroxystyryl)acrylonitrile (CR9);

(E,E)-2-(3,4-dihydroxybenzylaminocarbonyl)-3-(3,5-dimethoxy-4-hydroxystyryl)acrylonitrile (CR11);

(E,E)-2-aminothiocarbonyl-3-(3,5-dimethoxy-4-hydroxystyryl)acrylonitrile (CR12);

(E,E)-2-aminocarbonyl-3-(3,5-dimethoxy-4-hydroxystyryl)acrylonitrile (CR13);

(E,E)-2-carboxy-3-(3,5-dimethoxy-4-hydroxystyryl) acrylonitrile (CR14);

(E,E)-2-carbomethoxy-3-(3,5-dimethoxy-4-hydroxystyryl)acrylonitrile (CR15);

(E,E)-2-aminocarbonyl-3-[3,4-bis(t-butyldimethylsilyloxy)styryl)]acrylonitrile (CR16);

(E,E)-2-aminocarbonyl-3-(3,4-dihydroxystyryl) acrylonitrile (CR17);

(E,E)-2-(benzylaminocarbonyl)-3-([3,4-bis(t-butyldimethylsilyloxyl)styryl)]-)acrylonitrile (CR18);

(E,E)-2-(3,4-dihydroxybenzylaminocarbonyl)-3-styrylacrylonitrile (CR19):

(E,E)-2-(3,4-dihydroxybenzytaminocarbonyl)-3-[3,4-bis (t-butyldimethylsilyloxy)styryl)]acrylonitrile (CR20);

(E,E)-2-(3,4-dihydroxybenzylaminocarbonyl)-3-(3,4-dihydroxystyryl)acrylonitrile (CR21);

(E,E)-2-(β-ethanolaminocarbonyl)-3-(3,5-dimethoxy-4-hydroxystyryl)acrylonitrile (CR24);

(E,E)-2-(benzylaminocarbonyl)-3-(4-nitrostyryl)acrylonitrile (CR27);

(E,E)-2-(3,4dihydroxybenzylaminocarbonyl)-3-(4-nitrostyryl)acrylonitrile (CR28); and (E,E)-2-(1-amino-2,2-dicyanoethenyl)-3-(4-nitrostyryl)acrylonitrile (CR29).

In preferred embodiments of the present invention, the compounds of the invention include:

(E,E)-2-(benzylaminocarbonyl)-3-styrylacrylonitrile (CR1);

(E,E)-2-(benzylaminocarbonyl)-3-(3,4-dimethoxystyryl)acrylonitrile (CR2);

(E,E)-2-(benzylaminocarbonyl)-3-(3,5-dimethoxy-4-hydroxystyryl)acrylonitrile (CR3);

(E,E)-2-(benzylaminocarbonyl)-3-(3,4-dihydroxystyryl)acrylonitrile (CR4);

(E,E)-2-(phenylethylaminocarbonyl)-3-(3,4-dimethoxystyryl)acrylonitrile (CR5);

(E,E)-2-(phenylpropylaminocarbonyl)3(3,5-dimethoxy-4-hydroxystyryl)acrylonitrile (CR9);

(E,E)-2-(3,4-dihydroxybenzylaminocarbonyl)-3-(3,4-dimethoxy-4-hydroxystyryl)acrylonitrile (CR11);

(E,E)-2-aminothiocarbonyl-3-(3,5-dimethoxy-4-hydroxystyryl)acrylonitrile (CR12);

(E,E)-2-aminocarbonyl-3-(3,5-dimethoxy-4-hydroxystyryl)acrylonitrile (CR13);

(E,E)-2-carboxy-3-(3,5-dimethoxy-4-hydroxystyryl)acrylonitrile (CR14);

(E,E)-2-carbomethoxy-3-(3,5-dimethoxy-4-hydroxystyryl)acrylonitrile (CR15);

(E,E)-2-aminocarbonyl-3-(3,4-dihydroxystyryl)acrylonitrile (CR17);

(E,E)-2-(3,4-dihydroxybenzylaminocarbonyl)-3-styrylacylonitrile (CR19);

(E,E)-2-(3,5-dihydroxybenzylaminocarbonyl)-3-(3,4-dihydroxystyryl)acrylonitrile (CR21); and (E,E)-2-(β-ethanolaminocarbonyl)-3-(3,5-dimethoxy-4-hydroxystyryl)acrytonitrile (CR24).

In more preferred embodiments of the present invention, the compounds of the invention include:

(E,E)-2-(benzylaminocarbonyl)-3-(3,4-dihydroxystyryl)acrylonitrile (CR4);

(E,E)-2-(3,4-dihydroxybenzylaminocarbonyl)-3-(3,5-dimethoxy-4-hydroxystyryl)acrylonitrile (CR11);

(E,E)-2-aminocarbonyl-3-(3,4-dihydroxystyryl)acrylonitrile (CR17);

(E,E)-2-(3,4-dihydroxybenzylaminocarbonyl)-3-styrylacrylonitrile (CR19);

(E,E)-2-(3,4-dihydroxybenzylaminocarbonyl)-3-(3,4-dihydroxystyryl)acrylonitrile (CR21); and (E,E)-2-(β-ethanolaminocarbonyl)-3-(3,5-dimethoxy-4-hydroxystyryl)acrylonitrile The present invention includes within its scope, prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, for example, in "Design of Prodrugs" ed. H. Bundgaard, Elsevier, 1985.

Some of the compounds of the invention may have at least one asymmetric center. Where the compounds according to the invention have one asymmetric center, the may exist as enantiomers. Where the compounds of the invention possess two or more asymmetric centers, they may additionally exist as diastereomers. It is to be understood that all such isomers and mixtures thereof in any proportion are encompassed within the scope of the present invention.

The present invention includes radiolabeled forms of compounds of the invention, for example, compounds of the invention labeled by incorporation within the structure $^3H$ or $^{14}C$ or a radioactive halogen such as $^{125}I$.

The compounds of the invention may, for example, be derived from an activated cinnamyl compound and an activated cyano-substituted methylene compound. A person skilled in the art, therefore, may wish to provide a generic name for the compounds of the invention based on the cinnamyl moiety. However, generic nomenclature based on the formed acylonitrile moiety, for example, styryl acrylonitrile, would be more proper.

III. Methods of Preparing Compounds of the Invention

In accordance with another aspect of the present invention, the compounds of the invention can be prepared by processes analogous to those established in the art. Therefore, compounds of this invention may be prepared by the reaction sequence shown in Scheme 1:

Scheme 1

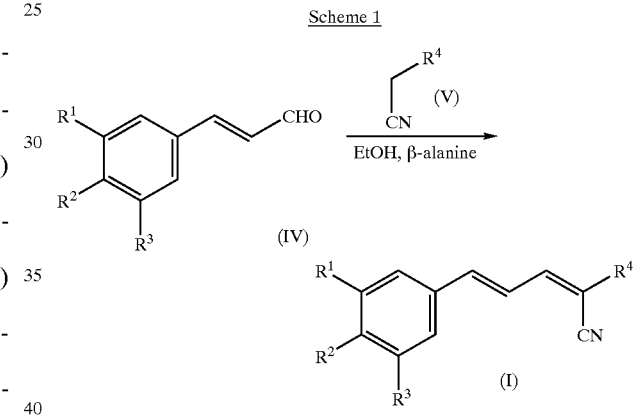

Compounds of the general Formulae I, II and/or III useful in the practice of this invention can be prepared by Knoevenagel condensation of α,β-unsaturated aldehydes, such as cinnamaldehyde or its various aryl-substituted homologues (IV), with a compound having active α-methylene group (V) Similar Knoevenagel condensations using ylidenemalononitriles as active α-methylene group components were described in a review (F. Freeman. Chem. Rev. 1980, V. 80, P. 329–350). For example, these condensations may be carned out in a polar solvent, such as ethanol, in the presence of catalytic amounts of a weak base, such as β-alanine. Reaction temperatures may be in the range of 20 to 100° C., depending on the stability of the materials used in the condensation.

Compounds of Formulae IV and/or V may be commercially available, such as cinnamaldehyde, and its 3,5-dimethoxy-4-hydroxy derivative. Other compounds of Formulae IV and/or V may be prepared using straightforward procedures. For example, various $R^1$, $R^2$, $R^3$-hydroxy substituted cinnamaldehydes can be prepared from the corresponding commercially available aryl substituted cinnamic acids Scheme 2 gives an example of the preparation of protected 3,4-dihydroxycinnamaldehyde (IVa) starting from 3,4-dihydroxycinnamic acid (VI). At the end of the reaction sequence, the protection groups can be removed using standard methods well known to those having skill in the art.

Scheme 2

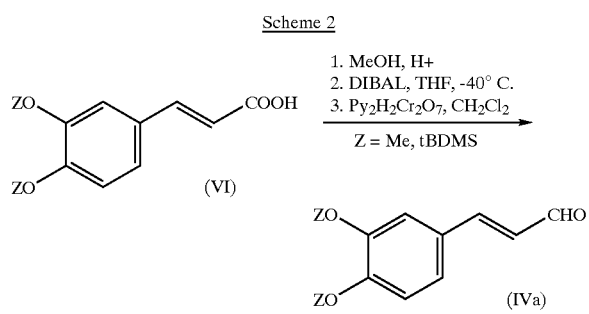

$R^1$, $R^2$, $R^3$ substituents may be also converted from one functional group to another, for example by known reduction of nitro groups into amino groups and the further transformation into dialkylamino groups, or by known conversion of hydroxy groups to halo groups.

α-Cyano amides with a reactive methylene group (Va) may be obtained, for example, as described in A. Gazit et.al. J. Med. Chem., 1991, V. 34, P. 1896–1907. For example, by heating methyl cyanoacetate (VII) and an appropriate commercially available amine (VIII) up to 100° C. without presence of a solvent for 12–15 h followed by vacuum distillation directly from the mixture (for example using a Kugelrohr apparatus), the desired products may be obtained (Scheme 3).

Scheme 3

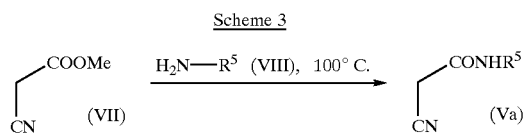

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, amino or carboxyl group. For example, when $R^1$, $R^2$ or $R^3$ is OH in a compound of Formulae I, II and/or III, it may be acylated using an activated acid in the presence of a base, and optionally, in inert solvent (e.g. an acid chloride in pyridine). Some common esters which have been utilized as prodrugs are phenyl esters, aliphatic ($C_8$–$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethyiditin in the presence of tetrakis(triphenylphosphine) palladium (0) in an inert solvent, such as dioxane, and at elevated temperatures, suitably 50–100° C.

IV. Uses

As hereinbefore mentioned, the inventors have prepared novel compounds of the Formulae I, II and III. Accordingly, the present invention includes all uses of the compounds of the invention including their use in therapeutic methods and compositions for modulating cell proliferation, their use in diagnostic assays and their use as research tools.

In one aspect, the present invention provides a method for modulating cell proliferation comprising administering an effective amount of a compound of the invention to a cell or animal in need thereof. Preferably, the invention provides a method of inhibiting cell proliferation comprising administering an effective amount of a compound of the invention to a cell or animal in need thereof. In particular, the method of the invention is useful in inhibiting the proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells as well as cell that over-proliferate in inflammatory conditions.

It has been determined that some of the compounds of the invention are very effective at killing cancer cells while at the same time they do not kill normal cells. These properties make the compounds of the invention extremely useful as anti-cancer agents. Accordingly, in one embodiment, the present invention provides a method of inhibiting the proliferation of a cancer cell comprising administering an effective amount of a compound of the invention to a cell or animal in need thereof.

The cancer cell that can be treated with a compound of the invention may be any type of cancer including, but not limited to, hematopoietic malignancies, including leukemias, lymphomas, and myelomas as well as other types of cancer including sarcomas, carcinomas, melanomas, adenomas, nervous system cancers and genitourinary cancers. Examples of leukemias include acute lymphoblastic leukemia (ALL), acute myelocytic leukemia (AML), chronic myeloid leukemia (CML), chronic lymphocytic leukemia (CLL) and juvenile myelo-monocytic leukemia (JMML). The types of ALL that may be treated with the compounds of the invention include cells that express a bcr-abl fusion protein, such as Philadelphia positive ALL cells, as well as Philadelphia negative ALL cells. Examples of lymphomas include B-cell Burkitt's lymphoma, Hodgkin's lymphomas, non-Hodgkin's lymphomas, including the Ki-1 positive anaplastic large cell lymphomas, T cell lymphomas and rare lymphomas such as the histiocytic lymphomas. Examples of myelomas include multiple myelomas.

In a specific embodiment, the present invention provides a method of inhibiting the proliferation of a cancer cell comprising administering an effective amount of a compound selected from the group of compounds:

(E,E)-2-(benzylaminocarbonyl)-3-styrytacrylonitrile (CR1);

(E,E)-2-(benzylaminocarbonyl)-3-(3,4-dimethoxystyryl) acrylonitrile (CR2);

(E,E)-2-(benzylaminocarbonyl)-3-(3,5-dimethoxy-4-hydroxystyrl)acrylonitrile (CR3);

(E,E)-2-(benzylaminocarbonyl)-3-(3,4-dihydroxystyryl) acrylonitrile (CR4);

(E,E)-2-(phenylethylaminocarbonyl)-3-(3,4-dimethoxystyryl)acrylonitrile (CR5);

(E,E)-2-(phenylethylaminocarbonyl)-3-(3,5-dimethoxy-4-hydroxystyryl)acrylonitrile (CR8);

(E,E)-2-(phenylpropylaminocarbonyl)-3-(3,5-dimethoxy-4-hydroxystyryl)acrylonitrile (CR9);

(E,E)-2-(3,4-dihydroxybenzylaminocarbonyl)-3-(3,5-dimethoxy-4-hydroxystyryl)acrylonitrile (CR11);

(E,E)-2-aminothiocarbonyl-3-(3,5-dimethoxy-4-hydroxystyryl)acrylonitrile (CR12):

(E,E)-2-aminocarbonyl-3-(3,5-dimethoxy-4-hydroxystyryl)acrylonitrile (CR13);

(E,E)-2-carboxy-3-(3,5-dimethoxy-4-hydroxystyryl) acrylonitrile (CR14);

(E,E)-2-carbomethoxy-3-(3,5-dimethoxy-4-hydroxystyryl)acrylonitrile (CR15):

(E,E)-2-aminocarbonyl-3-[3,4-bis(t-butyldimethylsilyloxy)styryl)]acrylonitrile (CR16);

(E,E)-2-aminocarbonyl-3-(3,4-dihydroxystylyl) acrylonitrile (CR17);

(E,E)-2-(benzylaminocarbonyl)-3-([3,4-bis(t-butyldimethylsilyloxy)styryl)]acrylonitrile (CR18);

(E,E)-2-(3,4dihydroxybenzylaminocarbonyl)-3-styrylacrylonitrile (CR19);

(E,E)-2-(3,4dihydroxybenzylaminocarbonyl)-3-[3,4-bis (t-butyldimethylsilyloxy)styryl)]acrylonitrile (CR20);

(E,E)-2-(3,4-dihydroxybenzylaminocarbonyl)-3-(3,4-dihydroxystyryl)acrylonitrile (CR21);

(E,E)-2-(β-ethanolaminocarbonyl)-3-(3,5-dimethoxy-4-hydroxystyryl)acrylonitrile (CR24);

(E,E)-2-(benzylaminocarbonyl)-3-(4-nitrostyryl) acrylonitrile (CR27);

(E,E)-2-(3,4-dihydroxybenzylaminocarbonyl)-3-(4-nitrostyryl)acrylonitrile (CR28); and (E,E)-2-(1-amino-2,2-dicyanoethenyl)-3-(4-nitrostyryl) acrylonitrile (CR29).

In a preferred embodiment, the present invention provides a method of inhibiting the proliferation of a cancer cell comprising administering an effective amount of a compound selected from the group of compounds:

(E,E)-2-(benzylaminocarbonyl)-3-(3,4-dihydroxystyryl) acrylonitrile (CR4);

(E,E)-2-(3,4-dihydroxybenzylaminocarbonyl)-3-(3,5-dimethoxy-4-hydroxystyryl)acrylonitrile (CR11);

(E,E)-2-aminocarbonyl-3-(3,4-dihydroxystyryl) acrylonitrile (CR17);

(E,E)-2-(3,4-dihydroxybenzylaminocarbonyl)-3-styrylacrylonitrile (CR19);

(E,E)-2-(3,4-dihydroxybenzylaminocarbonyl)-3-(3,4-dihydroxystyryl)acrylonitrile (CR21); and (E,E)-2-(β3-ethanolaminocarbonyl)-3-(3,5-dimethoxy-4-hydroxystyryl)acrylonitrile (CR24).

One skilled in the art can determine which compounds of the invention would have therapeutic utility, for example, in inhibiting cell proliferation in any type of cancer or cell proliferative disorder. Compounds may be examined for their efficacy in inhibiting cell growth in cell proliferation assays such as those described herein in Examples 35–56 Accordingly, the methods, uses and compositions of the invention are meant to include only those compounds having the desired effect.

The ability of the compounds of the invention to inhibit the growth of cancer cells, in particular hematopoetic cell malignancies, in vitro and in vivo was examined. Several of the compounds tested were found to eliminate cancerous cell growth in culture at sub-micromolar doses. In particular, CR4, CR11 and CR19 were found to be highly effective against a variety of cell types, such as Acute Lymphoblastic Leukemia, Philadelphia positive Leukemia and Acute Myeloid Leukemia. Low nanomolar doses of both CR4 and CR19 were highly toxic to cancer cells, while normal cell growth and differentiation were unaffected. These effects were obtained by long term exposure to low levels of the compounds. Accordingly, in one aspect, this invention provides a method of inhibiting the proliferation of a hematopoietic cancer cell by administering an effective amount of a compound of the invention, preferably, CR4 or CR11 or CR19, to a cell or animal in need thereof.

It has been determined that the compound CR4 is capable of effectively killing human Philadelphia positive acute lymphoblastic leukemia cells in vivo, using a murine model. CR4 efficiently reduced tumor load and infiltration of the organs by the ALL cells. The doses required to eliminate cancer cell growth do not result in detectable non-specific damage to the animal.

It has also been determined that the compounds of the invention, such as CR4 and CR11, are effective as ex vivo purging agents. For ex vivo administration, bone marrow cells may be removed from a patient with cancer and purged ex vivo with a compound of the invention. Such a purging will kill the tumor cells while leaving the normal bone marrow cells intact. After purging, the cells can be washed and reintroduced into the patient.

During ex vivo purging assays the cells were exposed to relatively high doses of the compounds (50 $\mu$M–100 $\mu$M) for short (1–24 hours) periods of time, resulting in the elimination of cancer cell growth, while normal bone marrow cells exposed to the same doses over the same period of time were relatively unaffected. Cancer cell death was effected by the induction of apoptosis. Accordingly, in another aspect of the invention, there is provided a method for killing cancer cells by ex vivo treatment of bone marrow from a patient with cancer with a compound of the invention, preferably CR4 and CR11 and then re-introducing the treated (or purged) bone marrow into the patient.

In addition to cancer, the compounds of the invention are useful in treating other conditions involving aberrant or abnormal cell proliferation. Other cell proliferative disorders that may be treated by the present invention include inflammatory diseases, allergies, autoimmune disease, graft rejection psoriasis, restenosis, artherosclerosis, and any other disorder wherein it is desirable to inhibit, prevent or suppress cell growth. Compounds of the invention may be tested for their efficacy in a particular cell proliferation disorder using assays and techniques known to those of skill in the art. For example, the following references provide assays for various conditions. Rheumatoid Arthritis: "Regulation of IL-15-Simulated TNF-alpha Production by Rolipram", Journal of Immunology (1999) volume 163 page 8236 by C. S. Kasyapa et al. Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al. Psoriasis: Journal of Immunology (2000) volume 165 page 224 "Inhibition of Keratinocyte apoptosis by IL-15: a new paramete in the pathegenosis of psoriasis" by R. Uchert (there is an umiatt over the U). Psoriasis: International Archives of allergy and Immunology (2000) Volume 123 page 275. "T-cell receptor mimic peptides and their potential application in T-cell mediated disease" by A. H. Enk.

The compounds of the invention are tyrosine kinase modulators and are useful in modulating tyrosine kinase activity, including the inhibition of tyrosine kinase activity, for the treatment of various conditions such as all proliferative disorders as mentioned above, Accordingly, the invention provides a method of modulating tyrosine kinase activity by administering an effective amount of a compound of the invention to a cell or animal in need thereof. In a further aspect, the invention provides a method of inhibiting tyrosine kinase activity by administering an effective amount of a compound of the invention to a cell or animal in need thereof.

While the compounds of the invention may act by inhibiting tyrosine kinase activity, one of skill in the art will appreciate that other modes or mechanisms of action for the compounds of the invention are possible.

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of this invention may be used in the form of the free base, in the form of salts, solvates and as hydrates. All forms are within the scope of the invention. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the invention include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesuffonic acid, ethanesulfonic acid, benzenesulfonic acid, p-toluenesulfonic acid, cyclohexylsulfamic acid, quinic acid, and the like.

In accordance with the methods of the invention, the described compounds or salts or solvates thereof may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention or a salt or solvate thereof may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO and mixtures thereof with or without alcohol, and in oils. Other solvents include taxol formulation, CMC, Tween20. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response. As an example, the compounds of the invention can be administered in a range from about 1 nanomolar to about 100 micromolar, preferably 50 nanomolar to 50 micromolar. For ex vivo treatment of cells over a short period, for example for 30 minutes to 1 hour or longer, higher doses of compound may be used than for long term in vivo therapy; for example, concentrations of 50 µM or higher may be used.

The present invention also includes a use of a compound or composition of the invention in order to inhibit cell proliferation, preferably cancer cell proliferation. The present invention further includes a use of a compound or a composition of the invention to prepare a medicament to inhibit cell proliferation, preferably cancer cell proliferation.

The compounds of the invention can be used alone or in combination with other agents that modulate tyrosine kinase activity or in combination with other types of treatment (which may or may not modulate tyrosine kinase activity) for cell proliferative disorders. Agents known in the art that inhibit tyrosine kinase activity include, but are not limited to, antisense nucleic acid and ribozymes targeted to nucleic acid encoding a receptor tyrosine kinase, antibodies able to modulate tyrosine kinase activity and other small molecule tyrosine kinase inhibitors such as those described in U.S. Pat. Nos. 5,891,917, 5,217,999, 5,773,476, 5,935,993, 5,656,655, 5,677,329 and 5,789,427. There are various examples of other types of treatment for cell proliferative disorders currently used to treat different types of cancers. The general treatments are based on the cancer type and do not specifically target tyrosine kinase activity. In a particular aspect of the present invention, the compounds of the invention may be used in combination with other therapies and therapeutics to treat leukemia.

In addition to the abovementioned therapeutic uses, the compounds of the invention are also useful in diagnostic assays, screening assays and as research tools.

In diagnostic assays the compounds of the invention may be useful in identifying or detecting a cell proliferative disorder. In such an embodiment, the compounds of the invention may be radiolabelled (as hereinbefore described) and contacted with a population of cells. The presence of the radiolabelled on the cells may indicate a cell proliferative disorder. In a specific embodiment, the radiolabelled compounds of the invention may be used to detect the presence of cells expressing a bcr-abl fusion protein.

In screening assays, the compounds of the invention may be used to identify other compounds that modulate cell proliferation or tyrosine kinase activity. As research tools, the compounds of the invention may be used in receptor binding assays and assays to study the localization of tyrosine kinases. In such assays, the compounds may also be radiolabelled.

Novel compounds and methods for modulating cell proliferation also are described in PCT/CA 01/_____, filed Apr. 12, 2001, which claims the priority benefit of U.S. Provisional Application Serial No. 60/196,936, filed Apr. 13, 2000, the disclosures of which are incorporated herein by reference in their entirety.

The following non-limiting examples are illustrative of the present invention:

EXAMPLES

Materials and Methods For Examples 1–34

$^1$H NMR spectra were obtained on a Varian Unity Plus spectrometer (USA) at 500 MHz with tetramethylsilane (TMS, Me$_4$Si) as an internal standard (δ=0). Electrospray mass spectra were recorded on an API III Plus triple quadrupole mass spectrometer (USA), with a direct introduction of the samples into the ionization source. Thin layer chromatography was performed with UV-254 aluminum-backed TLC sheets of 0.25 mm thickness (Kieselgel 60 F$_{254}$, Merck, Germany) HPLC separation of the compound of Example 13 was performed on a Waters 600 chromatograph (USA), column Nova-Pak C18 3.9×300 mm (Waters, USA). Vacuum distillations were done using Kugelrohr apparatus (Aldrich, USA) at stated temperatures of an oven. 3,5-Dimethoxy-4-hydroxycinnamaldehyde, 4-nitrocinnamaldehyde, 3,4-dimethoxycinnamic acid, 3,4-dihydroxycinnamic acid, 3,4-dimethoxybenzylamine, benzylamine, phenylethylamine, phenylpropylamine, methyl cyanoacetate, 2-cyanothioacetamide, 2-cyanoacetamide, cyanoacetic acid, β-ethanolamine, 2-amino-1-propene-1,1,3-tricarbonitrile were purchased from Aldrich (USA) and were used as received. The reagents were from Aldrich (USA). Solvents were purchased from Caledon (Canada).

Example 1
N-(Cyanoacetyl)3,4-dimethoxybenzylamide (A$_1$)

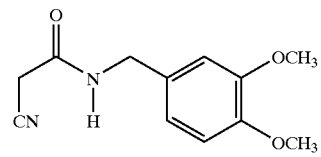

To 3,4-dimethoxybenzylamine (2.7 ml, 18 mmol) methyl cyanoacetate was added (1.6 ml, 18 mmol). The reaction was heated for 14 h at 100° C. Cooling gave a dark brown solid which was recrystallized from ethanol to give 2.90 g of the product (69% yield).

The product gave the following analytical data:
NMR (CD$_3$COCD$_3$, δ, ppm): 3.62 (s, 2H, CH$_2$CN), 3.78 (s, 6H, (OMe)$_2$), 4.34 (br.s., 2H, NHCH$_2$Ph), 6.84 (dd, 1H, J 1.95 and 8.1 Hz, H$^6$), 6.88 (d, 1H, J 8.1 Hz, H$^5$), 6.93 (d, 1H, J 1.95 Hz, H$^2$), 7.80 (br.s., 1H, NH).

MS, m/e (rel. intensity, %): 235 (19) [M+H]$^+$, 252 (100) [M+NH$_4$]$^+$, 257 (33) [M+Na]$^+$.

Example 2
N-(Cyanoacetyl)3,4-dihydroxybenzylamide (A$_2$)

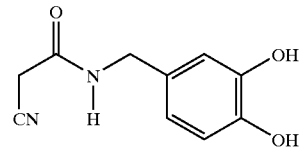

To N-(cyanoacetyl)3,4-dimethoxybenzylamide (Example 1, 0.2 g, 0.85 mmol) in 20 ml of CH$_2$Cl$_2$ boron tribromide was added under argon at −78° C. (0.24 ml, 2.56 mmol) in 2.5 ml of CH$_2$Cl$_2$. After 2 h the reaction was brought to room temperature and stirred overnight. The reaction was cooled to 0° C., 10 ml of 1N HCl was added, the solution was extracted with 3×50 ml of ethyl acetate, the organic phase was washed to neutral pH, dried with MgSO$_4$, and taken to dryness. The residue was purified by silica gel chromatography (CHCl$_3$-MeOH, 20:1) to give a yellow solid (0.07 g, 40% yield). The product gave the following analytical data;

NMR (CD$_3$COCD$_3$, δ, ppm): 2.83 (s, (OH)$_2$), 3.60 (s, 2H, CH$_2$CN), 4.25 (br.s., 2H, NHCH$_2$Ph), 6.63 (dd, 1H, J 1.95 and 8.1 Hz, $H^6$), 6.75 (d, 1H, J 8.1 Hz, $H^5$), 6.79 (d, 1H, J 1.95 Hz, $H^2$), 7.71 (br.s., 1H, NH).

MS, m/e (rel. intensity, %): 207 (38) $[M+H]^+$, 224 (100) $[M+NH_4]^+$, 229 (2.6) $[M+Na]^+$.

Example 3
(EE)-2-(3,4-Dihydroxybenzylaminocarbonyl)-3-(3,5-dimethoxy-4-hydroxystyryl)acrylonitrile (CR11)

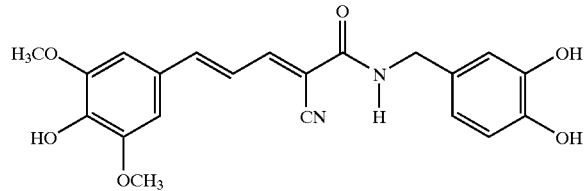

To 3,5-dimethoxy-4-hydroxycinnamaldehyde (0.042 g, 0.2 mmol) and N-(cyanoacetyl)3,4-dihydroxybenzylamide (Example 2, 0.042 g, 0.2 mmol) in 10 ml of ethanol 3 mg of β-alanine was added and the reaction was refluxed for 6 h. Water was added and the solid was recrystallized from 5 ml of ethanol twice to give 0.06 g (75%) of a red solid. The product gave the following analytical data:

NMR ($CD_3COCD_3$, δ, ppm): 2.81 (s, $(OH)_3$), 3.89 (s, 6H, $(OMe)_2$), 4.39 (br.s., 2H, $NHCH_2Ph$), 6.68 (dd, 1H, J 1.95 and 8.1 Hz, $H^{6'}$), 6.76 (d, 1H, J 8.1 Hz, $H^{5'}$), 6.86 (d, 1H, J 1.95 Hz, $H^{2'}$), 7.07 (br.s, 2H, $H^{2+6}$), 7.16 (dd, 1H, J 11.7 and 15.1 Hz, PhCCHCCN olefinic), 7.37 (d, 1H, J 15.1 Hz, PhCH olefinic), 7.70 (br.s, 1H, NH), 7.98 (dd, 1H, J 0.75 and 11.7 Hz, CHCN olefinic).

MS, m/e (rel. intensity, %): 397 (100) $[M+H]^+$, 414 (14) $[M+NH_4]^+$.

Example 4
N-(Cyanoacetyl)benzylamide ($A_3$)

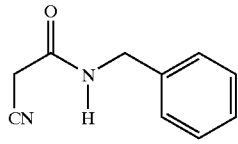

The compound was prepared as described in Example 1 by adding methyl cyanoacetate (1.3 ml, 14 mmol) to benzylamine (1.5 ml, 14 mmol). The compound was distilled in vacuo directly from the reaction mixture (Kugelrohr apparatus (Aldrich), 0.1 mm Hg, T. oven 180–190° C.) to give an off-white solid (2.34 g, 95%). The product gave the following analytical data, NMR ($CD_3COCD_3$, δ, ppm): 3.39 (s, 2H, $CNCH_2$), 4.46 (d, 2H, J 5.4 Hz, $NHCH_2Ph$), 6.40 (br.s., 1H, NH), 7.24–7.36 (m, 5H, Ph).

MS, m/e (rel. intensity, %): 175 (64) $[M+H]^+$, 192 $[M+NH_4]^+$.

Example 5
3,4-Dimethoxycinnamyl alcohol ($A_6$)

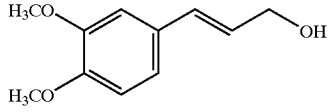

To a solution of 0.42 g (2.0 mmol) of 3,4-dimethoxycinnamic acid in 50 ml MeOH was added $SOCl_2$ (50 μl) and the mixture was stirred at 60° C. for 5 h. Methanol was taken to dryness and the obtained 3,4-dimethoxycinnamic acid methyl ester was reduced with 1M THF solution of diisobutylaluminum hydride (8.0 mmol) in absolute THF (50 ml) at 20° C. for 1 h. Water was added, the mixture was extracted with EtOAc, dried with $MgSO_4$ and distilled in vacuo (Kugelrohr apparatus (Aldrich), 0.1 mm Hg, T. oven 185–190° C.) giving an off-white solid, yield 0.36 g (92%), m.p. 70–71° C. The product gave the following analytical data:

NMR ($CD_3COCCD_3$, δ, ppm): 3.77, 3.82 (2×s, 2×3H, OMe+OMe), 4.19 (d, 2H, J 5.0 Hz, $CH_2OH$), 6.25 (dt, 1H, J 5.0 and 15.5 Hz, PhCCH olefinic), 6.51 (d, 1H, J 15.5 Hz, PhCH olefinic), 6.89 (m, 2H, $HS^{5+6}$), 7.05 (br.s., 1H, $H^2$).

MS, m/e (rel. intensity, %): 177 (100) $[M-OH]+$, 195 (4) $[M+H]^+$, 212 (59) $[M+NH_4]^+$, 217 (26) $[M+Na]^+$.

Example 6
3,4-Dimethoxycinnamaldehyde ($A_7$)

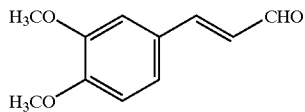

To a mixture of pyridinium dichromate (3.88 g, 10.3 mmol) and 4 g of finely grounded freshly activated molecular sieves 3 Å in 20 ml of $CH_2Cl_2$ 3,4-dimethoxycinnamyl alcohol in 10 ml of $CH_2Cl_2$ (Example 5, 1.00 g, 5.1 mmol) was added The reaction was stirred for 2 h, 0.5 ml of methanol was added, the residue was passed through silica gel and washed with 300 ml of ethyl acetate. After evaporation the compound was purified by silica gel chromatography (hexane-EtOAc, 5:1) leading to a crystallizing oil (0.62 g, 63%).

The product gave the following analytical data:
NMR ($CD_3COCD_3$, δ, ppm): 3.90 (2×s, 2×3H, $OCH_3$+$OCH_3$), 6.70 (dd, 1H, J 7.6 and 16.0 Hz, PhC=CH olefinic), 7.05 (d, 1H, J 8.3 Hz, $H^5$), 7.28 (dd, 1H, J 1.4 and 8.3 Hz, $H^6$), 7.37 (d, 1H, J 1.4 Hz, $H^2$), 7.60 (d, 1H, J 16.0 Hz, PhCH olefinic), 9.65 (d, 1H, J 7.6 Hz, CHO).

MS, m/e (rel. intensity, %): 193 (100) $[M+H]^+$, 210 (26) $[M+NH_4]^+$.

Example 7
(E,E)-2-(Benzylaminocarbonyl)-3-(3,4-dimethoxystyryl)acrylonitrile (CR2)

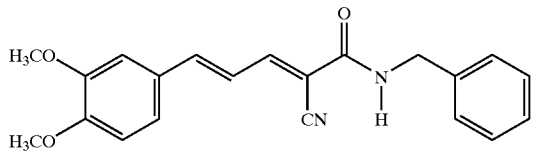

The compound was prepared as described in Example 3, by adding 3,4-dimethoxycinnamaldehyde (Example 6, 0.04 g, 0.2 mmol) to N-(cyanoacetyl)benzylamide (Example 4, 0.036 g, 0.2 mmol). After refluxing for 1 h and recrystallization from ethanol a yellow solid was obtained (0.045 g, 62%). The product gave the following analytical data:

NMR ($CD_3COCD_3$, δ, ppm): 3.90 (s, 2×3H, OMe+OMe), 4.57 (d, 2H, J<2 Hz, $NHCH_2Ph$), 7.08 (br.s., 1H, $H^2$), 7.17 (dd, 1H, J 11.5 and 15.2 Hz, PhCCHCCN olefinic), 7.23–7.42 (m, 8H, aromatic+$H^5$+$H^6$+PhCH olefinic), 7.90 (br.t, 1H, NH), 8.05 (dd, 1H, J 0.55 and 11.5 Hz, CHCN olefinic).

Example 8
(E,E)-2-(Benzylaminocarbonyl)-3-(3,4-dihydroxystyryl) acrylonitrile

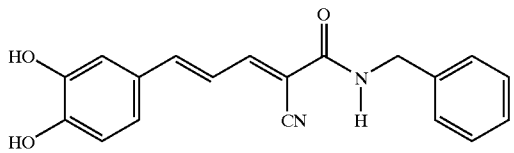

Boron tribromide (0.033 ml, 0.34 mmol) was added to (E,E)-2-(benzylamido)-3-(3,4-dimethoxystyryl)acrylonitrile (Example 7, 0.04 g, 0.11 mmol). The residue was purified by silica gel chromatography (CHCl$_3$-MeOH, 10:1) to give an orange solid (0.02 g, 55% yield). The product gave the following analytical data:

NMR (CD$_3$COCD$_3$, δ, ppm): 2.86 (br.s., 2H, (OH)$_2$), 4.55 (m, 2H, NHCH$_2$Ph), 6.90–7.42 (m, 10H, Ph+Ph'+olefinic), 7.87 (br.s., 1H, NH), 8.02 (dd, 1H, J<0.5 and 11.4 Hz, CHCN olefinic).

MS, m/e (rel. intensity, %): 295 (61) [M+H-CN]$^+$, 321 (100) [M+H]$^+$, 338 (30) [M+NH$_4$]$^+$.

Example 9
Methyl ester of 3,4-bis(t-butyldimethylsilyloxy)cinnamic acid (A$_8$)

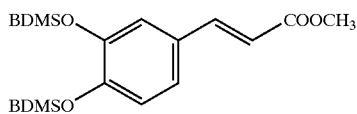

To a solution of 3.6 g (20 mmol) of 3,4-dihydroxycinnamic acid in 300 ml MeOH was added SOCl$_2$ (100 μl) and the mixture was stirred at 60° C. for 5 h. Methanol was taken to dryness and the obtained methyl ester was treated up with 10.2 g (68 mmol) of t-BuMe$_2$SiCl and 9.2 g (136 mmol) of imidazole in 100 ml DMF at 50° C. for 0.5 h. Mixture was diluted with water and extracted with hexane. Hexane was taken to dryness. The residue was distilled in vacuo (Kugelrohr apparatus (Aldrich), 0.1 mm Hg, T. oven 200–210° C.) and crystallized from hexane at −20° C. giving a white solid, yield 7.5 g (89%), m.p. 57–58° C. The product gave the following analytical data:

MS, m/e (rel. intensity, %): 423 (100) [M+H]$^+$, 440 (98) [M+NH$_4$]$^+$.

Example 10
3,4-Bis(t-butyldimethylsilyloxy)cinnamyl alcohol (A$_9$)

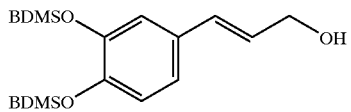

The compound was prepared as described in Example 5 by treating of 3,4-dihydroxycinnamic acid bis(BDMS) ether methyl ester (Example 9, 0.42 g, 1.0 mmol) with 1M THF solution of diisobutylaluminum hydride (4.0 mmol) in absolute THF (25 ml) at 20° C. for 1 h. After distilling in vacuo (Kugelrohr apparatus (Aldrich), 0.1 mm Hg, T. oven 185–200° C.) a white viscous oil was obtained, yield 0.33 g (85%). The product gave the following analytical data:

NMR (CD$_3$COCD$_3$, δ, ppm): 0.23, 0.24 (2×s, 2×6H, Me$_2$Si+Me$_2$Si), 1.00, 1.02 (2×s, 2×9H, t-BuSi+t-BuSi), 4.19 (d, 2H, J 4.9 Hz, CH$_2$OH), 6.22 (dt, 1H, J 4.9 and 16.0 Hz, PhCCH olefinic), 6.49 (d, 1H, J 16.0 Hz, PhCH olefinic), 6.85 (d, 1H, J 8.2 Hz, H$^5$), 6.92 (dd, 1H, J 2.1 and 8.2 Hz, H$^6$), 6.97 (d, 1H, J 2.1 Hz, H$^2$).

MS, m/e (rel. intensity, %): 377 (100) [M—OH]$^+$, 395 (2) [M+H]$^+$, 412 (15) [M+NH$_4$]$^+$.

Example 11
3,4-Bis(t-butyldimethylsilyfoxy)cinnamaldehyde (A$_{10}$)

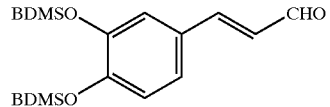

The compound was prepared as described in Example 6 by adding 3,4-bis(t-butyldimethylsilyloxy)cinnamyl alcohol (Example 10, 0.2 g, 0.5 mmol) in 5 ml of CH$_2$Cl$_2$ to a mixture of pyridinium dichromate (0.38 g, 1 mmol) and 1 g molecular sieves 3 Å in 20 ml of CH$_2$Cl$_2$. The residue was passed through silica gel and washed with 300 ml of EtOAc-hexane, 1:1. After evaporation the compound was purified by silica gel chromatography (hexane-EtOAc, 5:1) leading to an oil (0.15 g, 76%). The product gave the following analytical data:

NMR (CD$_3$COCD$_3$, δ, ppm): 0.26 and 0.28 (2×s, 2×6H, Me$_2$Si+Me$_2$Si), 1.01 and 1.02 (2×s, 2×9H, t-BuSi+t-BuSi), 6.60 (dd, 1H, J 7.7 and 15.9 Hz, PhCCH olefinic), 7.01 (dd, 1H, J<0.5 and 8.9 Hz, H$^6$), 7.27 (m, 2H, H$^{2+5}$), 7.60 (d, 1H, J 15.9 Hz, PhCH olefinic), 9.65 (d, 1H, d 7.7 Hz, CHO).

MS, m/e (rel. intensity, %): 367 (3) [M+H-CN]$^+$, 393 (100) [M+H]$^+$, 410 (10) [M+NH$_4$]$^+$.

Example 12
(E,E)-2-(Benzylaminocarbonyl)-3-([3,4-bis(t-Butyldimethylsilyloxy)styryl])acrylonitrile (CR18)

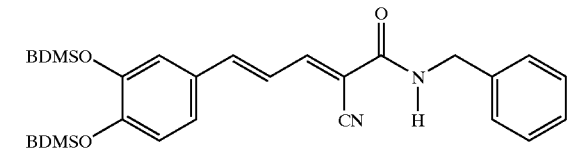

The compound was prepared as described in Example 3 by adding 3,4-bis(t-butyldimethylsilyloxy)cinnamaldehyde (Example 11, 0.100 g, 0.26 mmol) to N-(cyanoacetyl)benzylamide (Example 4, 0.044 g, 0.26 mmol. After refluxing for 2.5 h purification by silica gel chromatography (hexane-EtOAc, 15:1) provided a yellow solid (0.090 g, 64%). The product gave the following analytical data:

NMR (CD$_3$COCD$_3$, δ, ppm): 0.24 and 0.25 (2×s, 2×6H, Me$_2$Si+Me$_2$Si), 1.01 and 1.02 (2×s, 2×9H, t-BuSi+t-BuSi), 4.55 (br.s., 2H, NHCH$_2$Ph), 7.00 (d, 1H, J 8.5 Hz, H$^4$), 7.12 (dd, 1H, J 11.7 and 15.6 Hz, PhCCHCCN olefinic), 7.24–7.43 (m, 8H, aromatic and olefinic protons), 7.93 (br.s., 1H, NH), 8.02 (dd, 1H, J<0.5 and 11.7 Hz, CHCN olefinic).

MS, m/e (rel. intensity, %): 523 (30) [M+H-CN]$^+$, 540 (24) [M+NH$_4$-CN]$^+$, 549 (89) [M+H]$^+$, 566 (100) [M+NH$_4$]$^+$.

Example 13
(E,E)-2-(Benzylaminocarbonyl)-3-(3,4-dihydroxystyryl)acrylonitrile

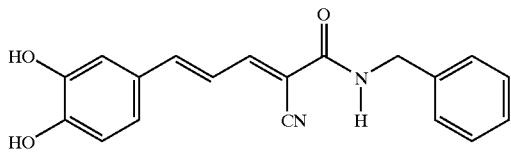

(E,E)-2-Benzylamido-3-[3,4-bis(t-butyldimethylsilyloxystyryl)]acrylonitrile (Example 12, 0.028 g, 0.052 mmol) was treated with 60 μl of a 1M THF solution of tetra-n-butylammonium fluoride in 2 ml of dry THF for 0.5 h at 20° C. After evaporation the compound was dissolved in 5 ml of chloroform-methanol, 20:1, passed through silica gel and washed with chloroform-methanol, 20:1. The residue was purified by HPLC chromatography (MeCN-H$_2$O, 60:40, UV detection at 340 nm) leading to an orange solid (0.010 g, 62%). The analytical data were identical to the compound prepared as described in Example 8.

Example 14
(E,E)-2-(3,4-Dihydroxybenzylaminocarbonyl)-3-styrylacrylonitrile (CR19)

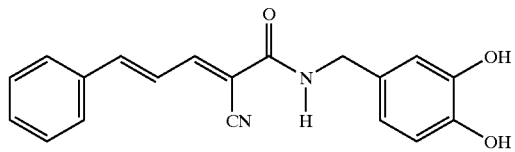

The compound was prepared as described in Example 3 by adding cinnamaldehyde (0.018 ml, 0.14 mmol) to N-(cyanoacetyl)3,4-dihydroxybenzylamide (Example 2, 0.03 g, 0.14 mmol). Afer refluxing for 2 h and recrystallization from ethanol, a yellow solid was obtained (0.027 g, 59%). The product gave the following analytical data:

NMR (CD$_3$COCD$_3$, δ, ppm): 2.82 (br.s., 2H, (OH)$_2$), 4.39 (br.s., 2H, NHCH$_2$Ph), 6.70 (dd, 1H, J 1.9 and 8.2 Hz, H$^{6'}$), 6.76 (d, 1H, J 8.2 Hz, H$^{5'}$), 6.87 (d, 1H, J 1.9 Hz, H$^{2'}$), 7.30 (dd, 1H, J 11.3 and 15.7 Hz, PhCCHCCN olefinic), 7.47 and 7.73 (2×m, 6H, aromatic protons and PhCH olefinic), 7.82 (br.s., 1H, NH), 8.04 (dd, 1H, J<0.5 and 11.3 Hz, CHCN olefinic).

MS, m/e (rel. intensity, %):321 (100) [M+H]$^+$, 338 (65) [M+NH$_4$]$^+$.

Example 15
(E,E)-2-(3,4-Dihydroxybenzylaminocarbonyl)-3-[3,4-bis(t-butyldimethylsilyloxy)styrytl)]acrylonitrile (CR20)

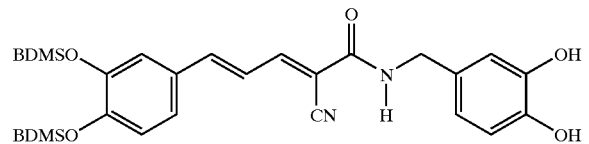

The compound was prepared as described in Example 3 by adding 3,4-bis(t-butyldimethylsilyloxy)cinnamaldehyde (Example 11, 0.015 g, 0.038 mmol) to N-(cyanoacetyl)3,4-dihydroxybenzylamide (Example 2, 0.0079 g, 0.038 mmol). After refluxing for 2 h and recrystallization from ethanol a yellow solid was obtained (0.014 g, 64%). The product gave the following analytical data:

NMR (CD$_3$COCD$_3$, δ, ppm): 0.22 and 0.24 (2×s, 2×6H, Me$_2$Si+Me$_2$Si), 1.01 and 1.03 (2×s, 2×9H, t-BuSi+t-BuSi), 2.72 (br.s., 2H, (OH)$_2$), 4.41 (br.s, 2H, NHCH$_2$Ph), 6.68–7.42 (m, 8H, aromatic and olefinic protons), 7.75 (br.s., 1H, NH), 8.00 (dd, 1H, J<0.5 and 12.0 Hz, CHCN olefinic).

MS, m/e (rel. intensity, %); 555 (5) [M+H-CN]$^+$, 572 (8) [M+NH$_4$–CN]$^+$, 581 (46) [M+H]$^+$, 598 (100) [M+NH$_4$]$^+$.

Example 16
(E,E)-2(3,4-Dihydroxybenzylaminocarbonyl)-3-(3,4-dihydroxystyryl)acrylonitrile (CR21)

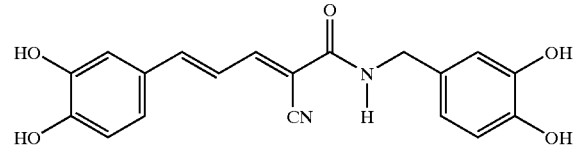

(E,E)-2-(3,4-Dihydroxybenzylamido)-3-[3,4-bis(t-butyldimethyl-silyloxystyryl)]acrylonitrile (Example 15, 0.026 g, 0.044 mmol) was treated with 60 μl of a 1M THF solution of tetra-n-butylammonium fluoride in 1.5 ml of dry THF for 0.5 h at 20° C. as described in Example 13. After purification, a yellow solid was obtained (0.006 g, 43%). The product gave the following analytical data:

NMR (CD$_3$COCD$_3$, δ, ppm): 4.38 (s, 1H, NHCH$_2$Ph), 6.67–7.22 (m, 6H, Ph+Ph'), 7.05 (dd, 1H, J 11.8 and 15.5 Hz, PhC=CH olefinic), 7.34 (d, 1H, J 15.5 Hz, PhCH olefinic), 7.70 (br.s, 1H, NH), 8.00 (d, 1H, J 11.8 Hz, CH=CCN olefinic).

MS, m/e (rel. intensity, %), 186 (86) [(HO)$_2$C$_6$H$_3$CH=CHCH=CCN]$^+$, 202 (28), 242 (100) [M+H-C$_6$H$_3$(OH)$_2$]$^+$, 353 (13) [M+H]$^+$, 370 (6) [M+NH$_4$]$^+$.

Example 17
(E,E)-2-(Benzylaminocarbonyl)-3-styrylacrylonitrile (CR1)

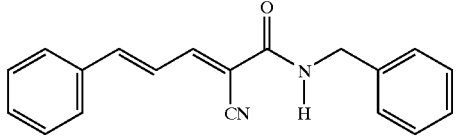

The compound was prepared as described in Example 3 by adding cinnamaldehyde (0.048 ml, 0.38 mmol) to N-(cyanoacetyl)benzylamide (Example 4, 0.066 g, 0.38 mmol). After refluxing for 1 h and recrystallization from ethanol a white solid was obtained (0.074 g, 68%). The product gave the following analytical data:

NMR (CD$_3$COCD$_3$, δ, ppm): 4.55 (s, 1H, NHCH$_2$Ph), 7.24–7.51 (m, 11H, Ph+Ph'+PhCCHCCN olefinic), 7.72 (br.d, 1H, J 6.5 Hz, CHCN olefinic), 7.98 (br.s., 1H, NH), 8.05 (d, 1H, J 11.7 Hz, PhCH olefinic).

MS, m/e (rel. intensity, %): 289 (100) [M+H]$^+$, 306 (92) [M+NH$_4$]$^+$.

Example 18
(E,E)-2-(Benzylaminocarbonyl)-3-(3,5-dimethoxy-4-hydroxystyryl)acrylonitrile (CR3)

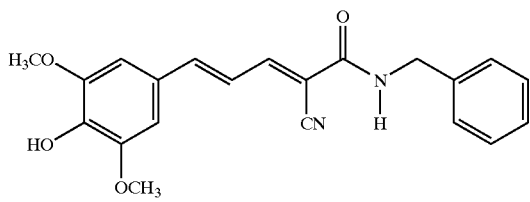

The compound was prepared as described in Example 3 by adding 3,5-dimethoxy-4-hydroxycinnamaldehyde (0.10 g, 0.48 mmol) to N-(cyanoacetyl)benzylamide (Example 4, 0.084 g, 0.48 mmol). After refluxing for 3 h and recrystallization from ethanol, a yellow solid was obtained (0.10 g, 57%) The product gave the following analytical data:

NMR (CD$_3$COCD$_3$, δ, ppm): 3.90 (s, 6H, (OMe)$_2$), 4.55 (m, 2H, NHCH$_2$Ph), 7.08 (br.s, 2H, H$^{2+6}$) 7.17 (dd, 1H, J 11.5 and 15.2 Hz, PhCCHCCN olefinic), 7.22–741 (m, 6H, Ph'+PhCH olefinic), 7.90 (br.s., 1H, NH), 8.01 (dd, 1H, J 0.55 and 11.7 Hz, CHCN olefinic)

MS, m/e (rel. intensity, %): 275 (14) [M+H-CN-MeOH-MeOH]$^+$, 307 (9) [M+H-CN-MeOH]$^+$, 339 (4) [M+H-CN]$^+$, 365 (100) [M+H]$^+$, 382 (16) [M+NH$_4$]$^+$.

Example 19
N-(Cyanoacetyl)phenylpropylamide (A$_5$)

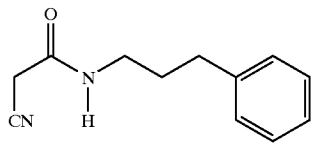

The compound was prepared as described in Example 1 by adding methyl cyanoacetate (0.98 ml, 11.1 mmol) to phenylpropylamine (1.58 ml, 11.1 mmol). The compound was distilled in vacuo directly from the reaction mixture (Kugelrohr apparatus (Aldrich), 0.1 mm Hg, T. oven 195–200° C.) to give an off-white solid (2.18 g, 97%). The product gave the following analytical data:

NMR (CD$_3$COCD$_3$, δ, ppm): 1.88 (q, 2H, J 7.3 Hz, PhCCH$_2$), 2.66 (t, 2H, J 7.3 Hz, PhCH$_2$), 3.28 (s, 2H, CNCH$_2$), 3.33 (dt, 2H, J 7.3 and 6.6 Hz, PhCCCH$_2$), 6.02 (br.s., 1H, NH), 7.15–7.30 (m, 5H, Ph).

MS, m/e (rel. intensity, %): 203 (88) [M+H]$^+$, 220 (100) [M+NH$_4$]$^+$.

Example 20
N-(Cyanoacetyl)phenylethylamide (A$_4$)

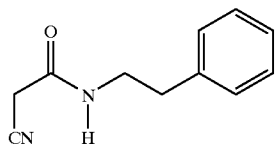

The compound was prepared as described in Example 1 by adding methyl cyanoacetate (1.1 ml, 12.4 mmol) to phenylethylamine (1.55 ml, 12.4 mmol). The compound was distilled in vacuo directly from the reaction mixture (Kugelrohr apparatus (Aldrich), 0.1 mm Hg, T. oven 190–195° C.) to give an off-white solid (2.14 g, 91%). The product gave the following analytical data:

NMR (CD$_3$COCD$_3$, δ, ppm): 2.80 (t, 2H, J 7.6 Hz, PhCH$_2$), 3.46 (br.t, 2H, J 7.6 Hz, PhCCH$_2$), 3.54 (s, 2H, CNCH$_2$), 7.20–7.31 (m, 5H, Ph), 7.51 (br.s., 1H, NH).

MS, m/e (rel. intensity, %): 189 (100) [M+H]$^+$, 206 (99) [M+NH$_4$]$^+$.

Example 21
(E,E)-2-(Phenylethylaminocarbonyl)-3-(3,4-dimethoxystyryl)acrylonitrile (CR5)

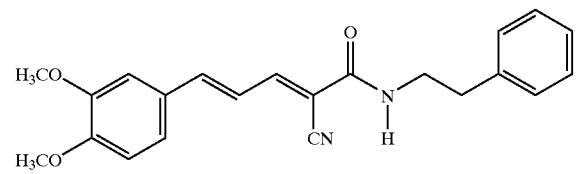

The compound was prepared as described in Example 3 by adding 3,4-dimethoxycinnamaldehyde (Example 6, 0.1 g, 0.52 mmol) to N-(cyanoacetyl)phenylethylamide (Example 20, 0.1 g, 0.52 mmol). After refluxing for 1 h and recrystallization from ethanol a yellow solid was obtained (0.12 g, 63%). The product gave the following analytical data:

NMR (CD$_3$COCD$_3$, δ, ppm): 2.91 (t, 2H, J 7.5 Hz, Ph'CH), 3.59 (br.t, 2H, J 7.5 Hz, Ph'CCH), 3.88, 3.89 (2×s, 2×3H, OCH$_3$+OCH$_3$), 7.04 (d, 1H, J 8.6 Hz, H5), 7.16 (dd, 1H, J 11.8 and 15.0 Hz, PhC=CH olefinic), 7.20–7.42 (m, 9H, aromatic+olefinic), 7.97 (d, 1H, J 11.8 Hz, CH=CCN olefinic).

MS, m/e (rel. intensity, %): 363 (100) [M+H]$^+$, 380 (34) [M+NH$_4$]$^+$.

Example 22
(E,E)-2-(Phenylethylaminocarbonyl)-3-(3,5-dimethoxy-4-hydroxystyryl)acrytonitrile (CR8)

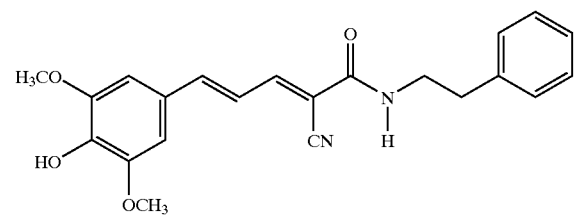

The compound was prepared as described in Example 3 by adding 3,5-dimethoxy-4-hydroxycinnamaldehyde (0.1 g, 0.48 mmol) to N-(cyanoacetyl)phenylethylamide (Example 20, 0.091 g, 0.48 mmol). The residue was purified by silica gel chromatography (CHCl$_3$-hexane, 1:1) to give a yellow solid (0.15 g, 83% yield). The product gave the following analytical data:

NMR (CD$_3$COCD$_3$, δ, ppm): 2.95 (t, 2H, J 7.6 Hz, CH$_2$Ph'), 3.62 (m, 2H, CH$_2$CPh'), 3.94 (s, 6H, (OMe)$_2$), 7.11 (s, 2H, H$^{2+6}$), 7.19 (dd 1H, J 11.7 and 15.3 Hz, PhCCHCCN olefinic), 7.23–7.36 (m, 5H, Ph'), 7.41 (d, 1H, J 15.3 Hz, PhCH olefinic), 7.45 (br.s., 1H, NH), 7.99 (d, 1H, J 11.7 Hz, CHCN olefinic).

MS, m/e (rel. intensity, %): 379 (100) [M+H]$^+$, 396 (7) [M+NH$_4$]$^+$.

Example 23

(E,E)-2-(Phenylpropylaminocarbonyl)-3-(3,5-dimethoxy-4-hydroxystyryl)acrylonitrile (CR9)

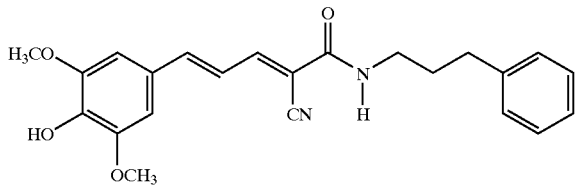

The compound was prepared as described in Example 3 by adding 3,5-dimethoxy-4 hydroxycinnamaldehyde (0.10 g, 0.48 mmol) to N-(cyanoacetyl)phenylpropylamide (Example 19, 0.097 g, 0.48 mmol). After refluxing for 3 h the residue was purified by silica gel chromatography ($CHCl_3$-hexane, 1:1) to give a brown solid (0.17 g, 90% yield). The product gave the following analytical data:

NMR ($CD_3COCD_3$, δ, ppm): 2.09 (q, 2H, J 7.5 Hz, $NHCCH_2CPh'$), 2.85 (t, 2H, J 7.5 Hz, $CH_2Ph'$), 3.57 (m, 2H, $CH_2CPh'$), 4.06 (s, 6H, $(OMe)_2$), 7.24 (s, 2H, $H^{2+6}$), 7.32 (dd, 1H, J 11.7 and 15.3 Hz, PhCCHCCN olefinic), 7.33–7.46 (m, 5H, Ph'), 7.53 (d, 1H, J 15.3 Hz, PhCH olefinic), 7.58 (br.s., 1H, NH), 8.11 (d, 1H, J 11.7 Hz, CHCN olefinic).

MS, m/e (rel. intensity, %): 331 (40), 348 (30), 359 (34), 376 (32), 393 (100) $[M+H]^+$, 410 (24) $[M+NH_4]^+$.

Example 24

(E,E)-2-Aminothiocarbonyl-3-(3,5-dimethoxy-4-hydroxystyryl)acrylonitrile (CR12)

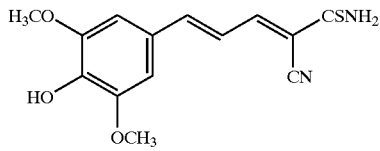

The compound was prepared as described in Example 3 by adding 3,5-dimethoxy-4-hydroxycinnamaldehyde (0.15 g, 0.72 mmol) to 2-cyanothioacetamide (0.073 g, 0.72 mmol). After refluxing for 1 h the residue was purified on a TLC-plate in hexane-ethyl acetate, 1:1 to give a red solid (0.10 g, 52%). The product gave the following analytical data:

NMR ($CD_3COCD_3$, δ, ppm): 2.85 (b.rs, $OH+NH_2$), 3.91 (s, 6H, $(OMe)_2$), 7.11 (s, 2H, $H^{2+6}$), 7.20 (dd, 1H, J 11.6 and 15.1 Hz, PhCCHCCN olefinic), 7.46 (d, 1H, J 15.1 Hz, PhCH olefinic), 8.22 (dd, 1H, J 0.73 and 11.6 Hz, CHCN olefinic).

MS, m/e (rel. intensity, %): 289 (100), 291 (60) $[M+H]^+$, 312 (8) $[M+Na]^+$.

Example 25

(E,E)-2-Aminocarbonyl-3-(3,5-dimethoxy-4-hydroxystyryl)acrylonitrile (CR13)

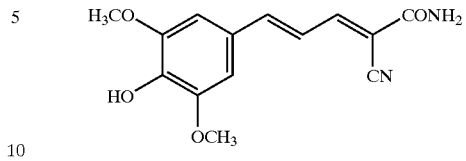

The compound was prepared as described in Example 3 by adding 3,5-dimethoxy-4-hydroxycinnamaldehyde (0.1 g, 0.48 mmol) to 2-cyanoacetamide (0.04 g, 0.48 mmol). After refluxing for 3 h and recrystallization from ethanol an orange solid was obtained (0.083 g, 63%). The product gave the following analytical data:

NMR ($CD_3COCD_3$, δ, ppm): 2.82–2.88 (br.s., $OH+NH_2$), 3.90 (s, 6H, $(OMe)_2$), 7.08 (s, 2H, $H^{2+6}$), 7.16 (dd, 1H, J 11.6 and 15.1 Hz, PhCCHCCN olefinic), 7.38 (d, 1H, J 15.1 Hz, PhCH olefinic), 7.96 (dd, 1H, J 0.73 and 11.6 Hz, CHCN olefinic).

MS, m/e (rel. intensity, %): 275 (100) $[M+H]^+$, 292 (28) $[M+NH_4]^+$.

Example 26

(E,E)-2-Carboxy-3-(3,5-dimethoxy-4-hydroxystyryl)acrylonitrile (CR14)

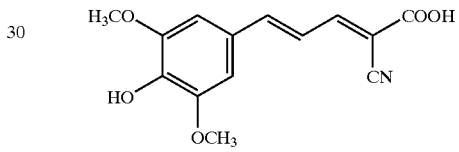

The compound was prepared as described in Example 3 by adding 3,5-dimethoxy-4-hydroxycinnamaldehyde (0.15 g, 0.72 mmol) to cyanoacetic acid (0.061 g, 0.72 mmol). After refluxing for 1 h and recrystallization from ethanol a yellow solid was obtained (0.15 g, 75%). The product gave the following analytical data:

NMR ($CD_3COCD_3$, δ, ppm); 3.00 (br.s, OH), 3.91 (s, 6H, $(OMe)_2$), 7.12 (s, 2H, $H^{2+6}$), 7.21 (dd, 1H, J 11.6 and 15.1 Hz, PhCCHCCN olefinic), 7.50 (d, 1H, J 15.1 Hz, PhCH olefinic), 8.04 (dd, 1H, J 0.73 and 11.6 Hz, CHCN olefinic).

MS, m/e (rel. intensity, %): 276 (66) $[M+H]^+$, 293 (100) $[M+NH_4]^+$.

Example 27

(E,E)-2-Carbomethoxy-3-(3,5-dimethoxy-4-hydroxystyryl)acrylonitrile (CR15)

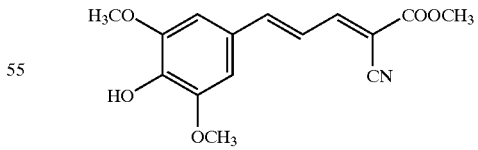

The compound was prepared as described in Example 3 by adding 3,5-dimethoxy-4-hydroxycinnamaldehyde (0.15 g, 0.72 mmol) to methyl cyanoacetate (0.064 ml, 0.72 mmol). After refluxing for 1 h and recrystallization from ethanol an orange solid was obtained (0.2 g, 90%). The product gave the following analytical data:

NMR ($CD_3COCD_3$, δ, ppm): 2.84 (br.s., OH), 3.84 (s, 3H, COOMe), 3.91 (s, 6H, $(OMe)_2$), 7.12 (s, 2H, $H^{2+6}$), 7.21 (dd, 1H, J 11.6 and 15.1 Hz, PhCCHCCN olefinic), 7.53 (d, 1H, J 15.1 Hz, PhCH olefinic), 8.05 (dd, 1H, J 0.73 and 11.6 Hz, CHCN olefinic).

MS, m/e (rel. intensity, %): 290 (100) [M+H]$^+$, 307 (99) [M+NH$_4$]$^+$.

Example 28
(E,E)-2-Aminocarbonyl-3-[3,4bis(t-Butyldimethylsilyloxy)styryl]acrylonitrile (CR16)

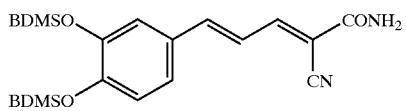

The compound was prepared as described in Example 3 by adding 3,4-bis(t-butyldimethylsilyloxy)cinnamaldehyde (Example 11, 0.15 g, 0.38 mmol) to 2-cyanoacetamide (0.032 g, 0.38 mmol). After refluxing for 0.5 h, purification by silica gel chromatography (hexane-EtOAc, 5:1) provided a crystallizing oil (0.10 g, 57%).

NMR (CD$_3$COCD$_3$, δ, ppm): 0.22 and 0.24 (2×s, 2×6H, Me$_2$Si+Me$_2$Si), 1.01 and 1.03 (2×s, 2×9H, t-BuSi+t-BuSi), 7,01, 7.23–7.29 (m, 3H, aromatic), 7.11 (dd, 1H, J 11.9 and 15.3 Hz, PhC═CH olefinic), 7.40 (d, 1H, J 15.3 Hz, PhCH olefinic), 7.98 (d, 1H, J 11.9 Hz, CH═CCN olefinic).

MS, m/e (rel. intensity, %): 459 (100) [M+H]$^+$, 476 (89) [M+NH$_4$]$^+$.

Example 29
(E,E)-2-Aminocarbonyl-3-(3,4-dihydroxystyryl)acrylonitrile (CR17)

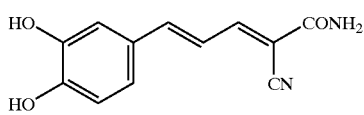

(E,E)-2-Acetamido-3-(3,4-bis(t-butyldimethylsilyloxystyryl))acrylonitrile (Example 28, 0.1 g, 0.22 mmol) was treated with an excess of a 1M THF solution of tetra-n-butylammonium fluoride in benzene for 0.5 h at 20° C. as described in Example 13. After purification, a yellow solid was obtained (0.04 g, 85%). The product gave the following analytical data:

MS, m/e (rel. intensity, %): 231 (83) [M+H]$^+$, 248 (100) [M+NH$_4$]$^+$.

Example 30
N-(Cyancacetyl)β-ethanalamide (A$_{11}$)

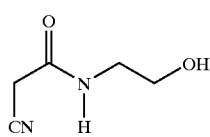

To β-ethanolamine (1.37 ml, 22.6 mmol), methyl cyanoacetate was added (2.0 ml, 22.6 mmol). The reaction was heated for 30 h at 100° C. Cooling gave a brown solid which was recrystallized from ethanol to give 2.10 g of the product (71%). The product gave the following analytical data:

MS, m/e (rel. intensity, %):129 (30) [M+H]$^+$, 146 (100) [M+NH$_4$]$^+$.

Example 31
(E,E)-2-(β-Ethanolaminocarbonyl)-3-(3,5-dimethoxy-4-hydroxystyryl)acrylonitrile (CR24)

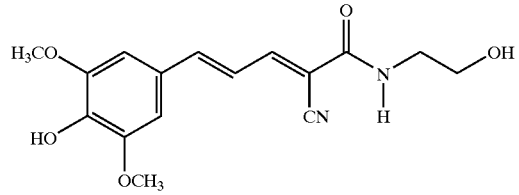

To 3,5-dimethoxy-4-hydroxycinnamaldehyde (0.018 g, 0.086 mmol), N-(cyanoacetyl)β-ethanolamide (Example 30, 0.010 g, 0.086 mmol) was added. After refluxing for 2 h and purification on silica gel, CHCl$_3$-MeOH, 5:1, a yellow solid was obtained. (0.024 g, 87%). The product gave the following analytical data:

NMR (CD$_3$COCD$_3$, δ, ppm): 3.47, 3.67 (2×m, 4H, NHCH$_2$+CH$_2$OH), 3.90 (s, 6H, OCH$_3$+OCH$_3$), 7.07 (br.s, 2H, H$^{2+6}$), 7.16 (dd, 1H, J 11.7 and 15.2 Hz, PhC═CH olefinic), 7.31 (br.s, 1H, NH), 7.38 (d, 1H, J 15.2 Hz, PhCH olefinic), 7.97 (d, 1H, J 11.7 Hz, CH═CCN olefinic).

MS, m/e (rel. intensity, %): 319 (70) [M+H]$^+$, 341 (100) [M+Na]$^+$.

Example 32
(E,E)-2-(Benzylaminocarbonyl)-3-(4-nitrostyryl)acrylonitrile (CR27)

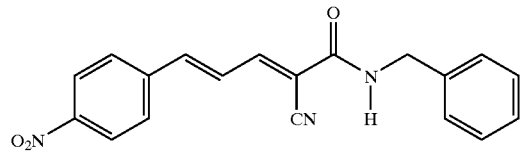

The compound was prepared as described in Example 3 by adding 4-nitrocinnamaldehyde (0.022 g, 0.12 mmol) to N-(cyanoacetyl)benzylamide (Example 4, 0.022 g, 0.12 mmol). After refluxing for 1 h, the product was purified by silica gel chromatography (CHCl$_3$-MeOH, 5:1) to give a yellow solid (0.033 g, 81%) The product gave the following analytical data:

NMR (CD$_3$COCD$_3$, δ, ppm): 4.56 (br.s, 2H, NHCH$_2$), 7.24–7.38 (m, 6H, Ph'+NH), 7.47 (dd, 1H, J 11.1 and 15.2 Hz, PhC═CH olefinic), 7.62 (d, 1H, J 15.2 Hz, PhCH olefinic), 8.02, 8.32 (2×br.d, 4H, J 8.8 and 8.3 Hz, Ph), 8.08 (d, 1H, J 11.1 Hz, CH═CCN olefinic).

MS, m/e (rel. intensity, %): 334 (100) [M+H]$^+$, 351 (16) [M+NH$_4$]$^+$, 356 (28) [M+Na]$^+$.

Example 33
(E,E)-2-(3,4-Dihydroxybenzylaminocarbonyl)-3-(4-nitrostyryl)acrylonitrile (CR28)

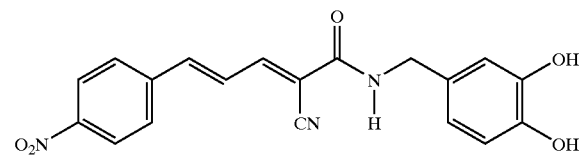

The compound was prepared as described in Example 3 by adding 4-nitrocinnamaldehyde (0.009 g, 0.05 mmol) to N-(cyanoacetyl)3,4-dihydroxybenzylamide (Example 2, 0.010 g, 0.05 mmol). After refluxing for 2 h and recrystallization from ethanol a yellow solid was obtained (0.007 g, 39%). The product gave the following analytical data:

NMR (CD$_3$COCD$_3$, δ, ppm): 2.81, 2.83 (2xbr.s, 2H, OH+OH), 4.39 (br.s, 2H, NHCH$_2$), 6.69 (br.d, 1H, J<0.5 and 7.6 Hz, H$^{6'}$), 6.76 (d, 1H, J 7.6 Hz, H$^{5'}$), 6.86 (br.d, 1H, J<0.5 Hz, H$^{2'}$), 7.47 (dd, 1H, J 11.7 and 15.2 Hz, PhC=CH olefinic), 7.61 (d, 1H, J 15.2 Hz, PhC olefinic), 7.91 (br.s, 1H, NH), 8.02, 8.31 (2xbr.d, 4H, J 8.2 and 8.8 Hz, Ph), 8.06 (d, 1H, J 11.7 Hz, CH=CCN olefinic).

MS, m/e (rel. intensity, %): 331 (21) [M-OH-OH]$^+$, 348 (47) [M-OH]$^+$, 366 (100) [M+H]$^+$, 383 (97) [M+NH$_4$]$^+$.

Example 34
(E,E)-2-(1-Amino-2,2-dicyanoethenyl)-3-(4-nitrostyryl) acrylonitrile (CR29)

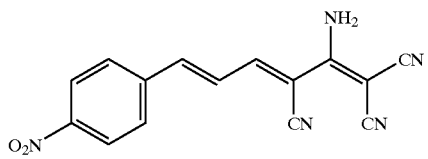

The compound was prepared as described in Example 3 by adding 4-nitrocinnamaldehyde (0.051 g, 0.29 mmol) to 2-amino-1-propene-1,1,3-tricarbonitrile (0.038 g, 0.29 mmol). After refluxing for 4 h and recrystallization from ethanol a yellow solid was obtained (0.08 g, 51%). The product gave the following analytical data:

NMR (CD$_3$COCD$_3$, δ, ppm): 7.54 (dd, 1H, J 11.1 and 15.8 Hz, PhC=CH olefinic), 7.67 (d, 1H, J 15.8 Hz, PhCH olefinic), 7.99 (d, 1H, J 11.1 Hz, CH=CCN olefinic), 8.08, 8.32 (2xbr.d, 4H, J 8.8 and 8.8 Hz, Ph).

MS, m/e (rel. intensity, %): 309 (100) [M+NH$_4$]$^+$, 314 (67) [M+Na]$^+$.

Example 35
Effect of CR4 Upon Normal Bone Marrow Differentiation in Culture

The CFU-GEMM assay was performed according to Fauser and Messner (1978, Blood, 52(6) 143–8) and Messner and Fausser (1980, Blut, 41(5) 327–33) with some variations. In brief, heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs. The fractionated BM cells at 2×10$^5$ cells/ml were cultured in IMDM (OCl, Toronto) containing 0.9% (vol/vol) methylcellulose supplemented with 30% FCS (Cansera Rexdale, ON.) or normal human plasma, a cocktail of cytokines containing G-CSF (10 ng/ml, Amgen), IL-3 (40 U/ml, Immunex), MGF (50 ng/ml, Immunex), Erythropoietin (2 u/ml, Epprex) or TPO (10 ng/ml, Amgen), 5×10$^{-5}$M β-2-mercaptoethanol and the specified concentration of CR4. The culture mixture was plated in 1 ml volumes into 35 mm petri dishes and incubated at 37° C., 5% CO$_2$ in a humidified atmosphere. All cultures were evaluated at 14 days for the number of BFU-E colonies (defined as aggregates of more than 500 hemoglobinized cells or, 3 or more erythroid subcolonies), OFU-GM colonies (defined as granulocyte or monocyte-macrophage cells or both), CFU-Meg colonies (comprising 4 or more megakaryocytes) and CFU-GEMM colonies (a mixed population comprising of all elements).

The results shown in FIG. 1 demonstrate that CR4 displayed negligible toxicity upon normal bone marrow at doses up to 5 μM. At 10 μM CR4 began to cause some inhibition of BFU-E colony formation, but at the same time significantly stimulated CFU-GM colony numbers.

Example 36
Killing of Philadelphia Positive Acute Lymphablastic Leukemia by Low-dose CR4 in Culture Ph+ ALL cells were plated in 1 ml volumes, in the absence of exogenous growth factors, into 35 mm petri dishes (Nunc, Gibco) containing alpha MEM (Gibco) plus 10% FCS (Cansera Rexdale, ON.) in 0.9% (vol/vol) methylcellulose (Fluka, Switzerland) with the indicated concentrations of CR4. Cultures were set at 37° C., 5% CO$_2$ in a humidified atmosphere. Colonies consisting of more than 20 cells were counted at 12 days or earlier using an inverted microscope.

Figure 2:
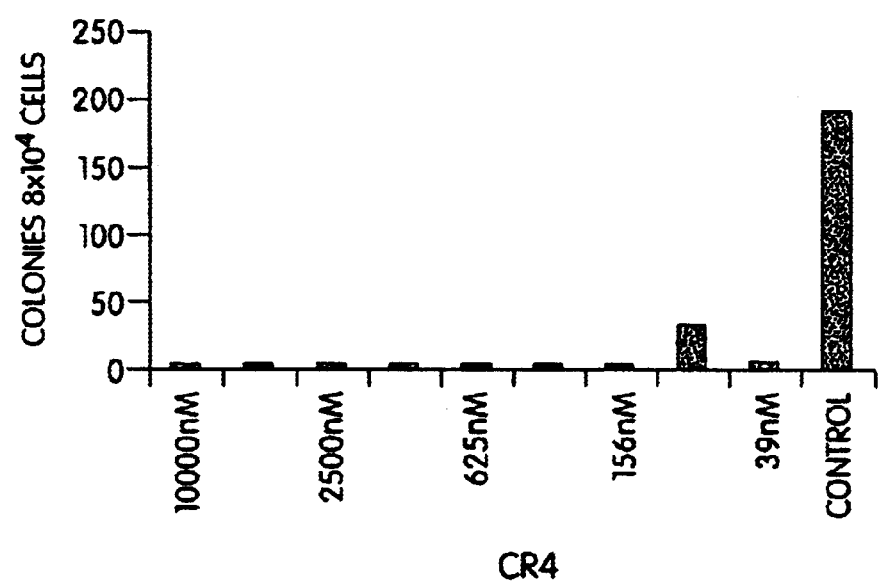
FIG. 2 is a bar graph showing the killing of Philadelphia positive acute lymphoblastic leukemia by low-dose CR4 in culture.

The results shown in FIG. 2 demonstrate that CR4 effected a significant inhibition of Ph+ ALL cell proliferation and survival at low nanomolar doses (35–100). CR4 has no effect upon normal cells at equivalent concentrations.

Example 37
Killing of Philadelphia Positive Z119 Acute Lymphoblastic Leukemia Cells by Low-dose CR4 in Culture Z119 cells were plated in 1 ml volumes at a density of 1×10$^4$ cells/ml, in the absence of exogenous growth factors, into 35 mm petri dishes (Nunc, Gibco) containing IMDM (OCl, Toronto) plus 20% FCS (Cansera Rexdale, ON.) in 0.9% (vol/vol) methylcellulose (Fluka, Switzerland) with the indicated concentration of CR4. Cultures were set at 37° C., 5% CO$_2$ in a humidified atmosphere. Colonies consisting of more than 20 cells were counted at 7 days or earlier using an inverted microscope.

Figure 3:
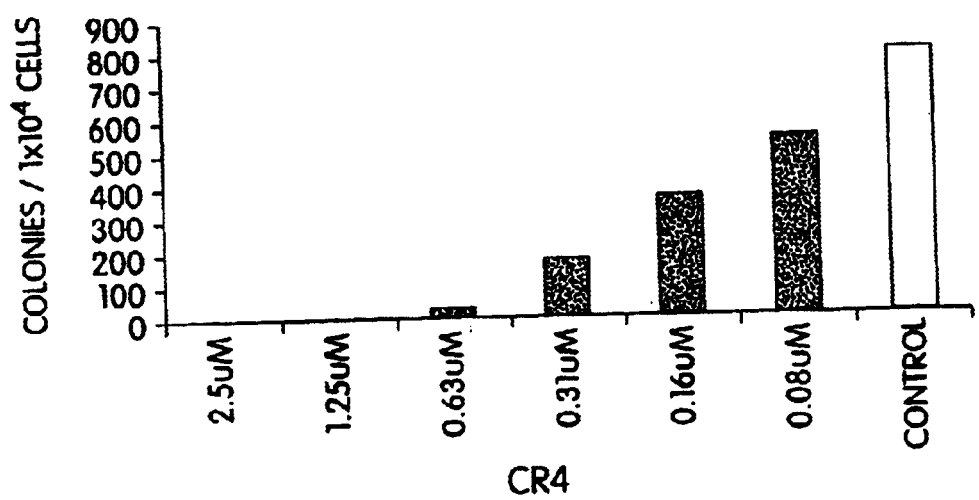
FIG. 3 is a bar graph showing the killing of Philadelphia positive Z119 Acute lymphoblastic leukemia cells by low-dose CR4 in culture.

The results shown in FIG. 3 demonstrate that CR4 effected a significant inhibition of Z119 ALL cell proliferation and survival at low nanomolar doses. CR4 has no effect upon normal cells at equivalent concentrations.

Example 38
Killing of AML-3 Acute Myeloid Leukemia Cells by Low-dose CR4 in Culture OCl-AML-3 cells were plated in 35 mm petri dishes (Nunc, Gibco) in 1 ml volumes at a density of 3.3×10$^3$ cells/ml, in the absence of exogenous growth factors, containing alpha MEM plus 20% FCS (Cansera, Rexdale Ont.), and 0.9% (vol/vol) methylcellulose (Fluka, Switzerland) and the indicated concentrations of CR4. Cell cultures were incubated in a humidified atmosphere at 37° C. with 5% CO$_2$. Colonies containing more than 20 cells were scored, using an inverted microscope, at 5–6 days.

Figure 4:
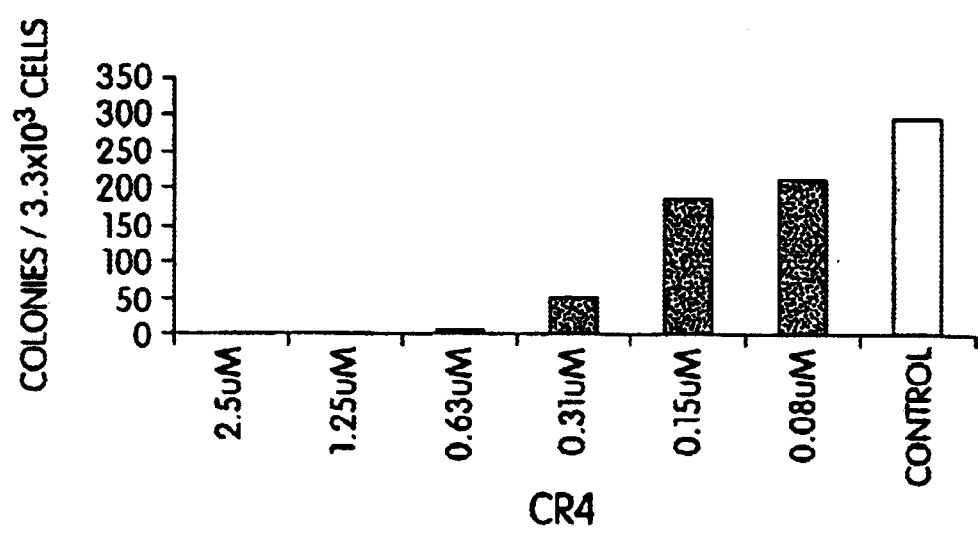
FIG. 4 is a bar graph showing the killing of AML-3 acute myeloid leukemia cells by low-dose CR4 in culture.

The results shown in FIG. 4 demonstrate that CR4 effected a complete inhibition of AML-3 cell proliferation and survival at nanomolar concentrations (300–600 nM). CR4 has no effect upon normal cell survival at equivalent concentrations.

Example 39
Killing of Ly-MN Lymphoma Cells by Low-dose CR4 in Culture

Ly-MN cells were plated in 1 ml volumes, in the absence of exogenous growth factors, into 35 mm petri dishes (Nunc, Gibco) containing IMDM (OCl, Toronto) plus 20% human cord blood plasma in 0.9% (vol/vol) methylcellulose (Fluka, Switzerland) and the indicated concentrations of CR4. Cultures were set at 37° C., 5% CO$_2$ in a humidified atmosphere. Colonies consisting of more than 20 cells were counted at 5 days or earlier using an inverted microscope.

Figure 5:
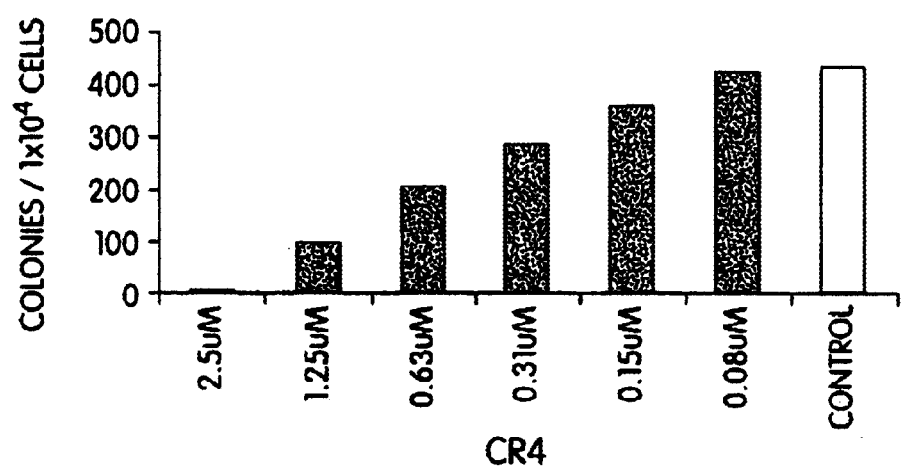
FIG. 5 is a bar graph showing the killing of Ly-MN lymphoma cells by low-dose CR4 in culture.

The results shown in FIG. 5 demonstrate that CR4 significantly inhibited cell proliferation and survival at nanomolar doses, and effected a inhibition by 2.5 $\mu$M. CR4 has no effect upon normal cells at equivalent concentrations.

Example 40
Killing of Primary Juvenile Myelo-Monocytic Leukemia Cells by CR4 in Culture Heparinized bone marrow cells from a JMML patient were layered over Percoll (1.077 gm/ml) (Pharmacia Fine Chemical, Piscataway N.J.) and centrifuged at 400 g at 4° C. for 10 minutes to remove neutrophils and RBCs. Cells were further fractionated and purified on Miltenyl MS columns (Miltenyl Biotec GmbH, Germany) to acquire an early progenitor population of $CD34^+$ cells. The fractionated BM $CD34^+$ cells at a density of $1 \times 10^4$ cells/ml were cultured in IMDM (OCl, Toronto) containing 0.9% (vol/vol) methylcellulose supplemented with 30% FCS (Cansera Rexdale, ON.) with the indicated concentration of CR4. The culture mixture was plated in 1 ml volumes into 35 mm petri dishes and incubated at 37° C., 5% $CO_2$ in a humidified atmosphere. Colonies consisting of more than 20 cells were counted at 12 days or earlier using an inverted microscope.

Figure 6:
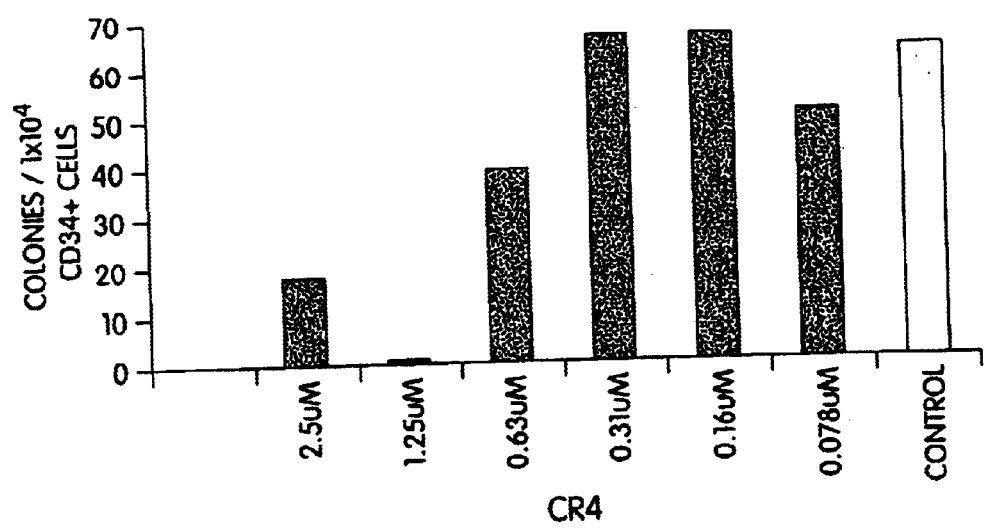
FIG. 6 is a bar graph showing the killing of primary juvenile myelo-monocytic leukemia cells by CR4 in culture.

The results shown in FIG. 6 demonstrate that CR4 displayed moderate killing ability with primary JMML cells, with 80–90 percent inhibition achieved by 5 $\mu$M concentrations.

Example 41
Killing of OCl-LY2 Lymphoma Cells by Low-dose CR4 in Culture

OCl-LY2 cells were plated in 1 ml volumes, in the absence of exogenous growth factors, into 35 mm petri dishes (Nunc, Gibco) containing IMDM (OCl, Toronto) plus 20% human cord blood plasma in 0.9% (vol/vol) methylcellulose (Fluka, Switzerland) and the indicated doses of CR4. Cultures were set at 37° C., 5% $CO_2$ in a humidified atmosphere. Colonies consisting of more than 20 cells were counted at 5 days or earlier using an inverted microscope.

Figure 7:
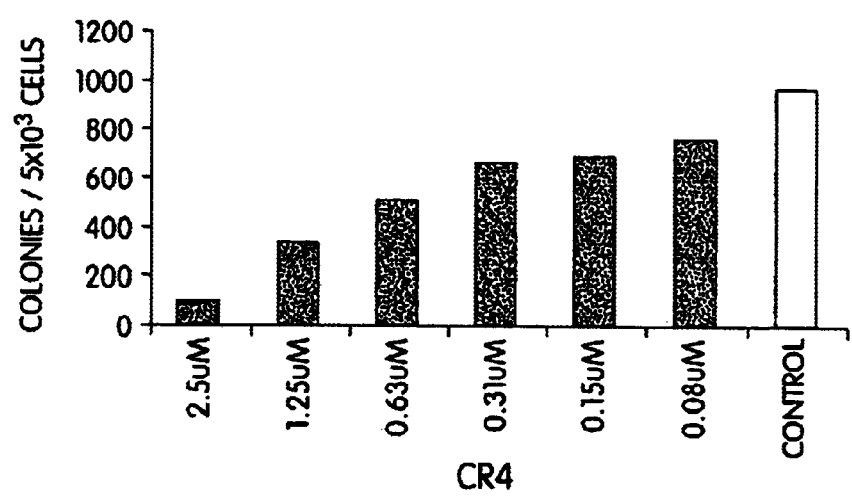
FIG. 7 is a bar graph showing the killing of OCl-LY2 lymphoma cells by low-dose CR4 in culture.

The results shown in FIG. 7 demonstrate that CR4 significantly inhibited cell proliferation and survival at high nanomolar to low micromolar doses (90% at 2.5 $\mu$M). CR4 has no effect upon normal cells at equivalent concentrations.

Example 42
Killing of Philadelphia Positive ALL Cells by CR17 and CR21 in Culture ALL cells were plated in 1 ml volumes, in the absence of exogenous growth factors, into 35 mm petri dishes (Nunc, Gibco) containing alpha MEM (Gibco) plus 20% FCS (Cansera Rexdale, ON.) in 0.9% (vol/vol) methylcellulose (Fluka, Switzerland) and the indicated concentrations of compound Cultures were set at 37° C., 5% $CO_2$ in a humidified atmosphere Colonies consisting of more than 20 cells were counted at 12 days or earlier using an inverted microscope.

Figure 8:
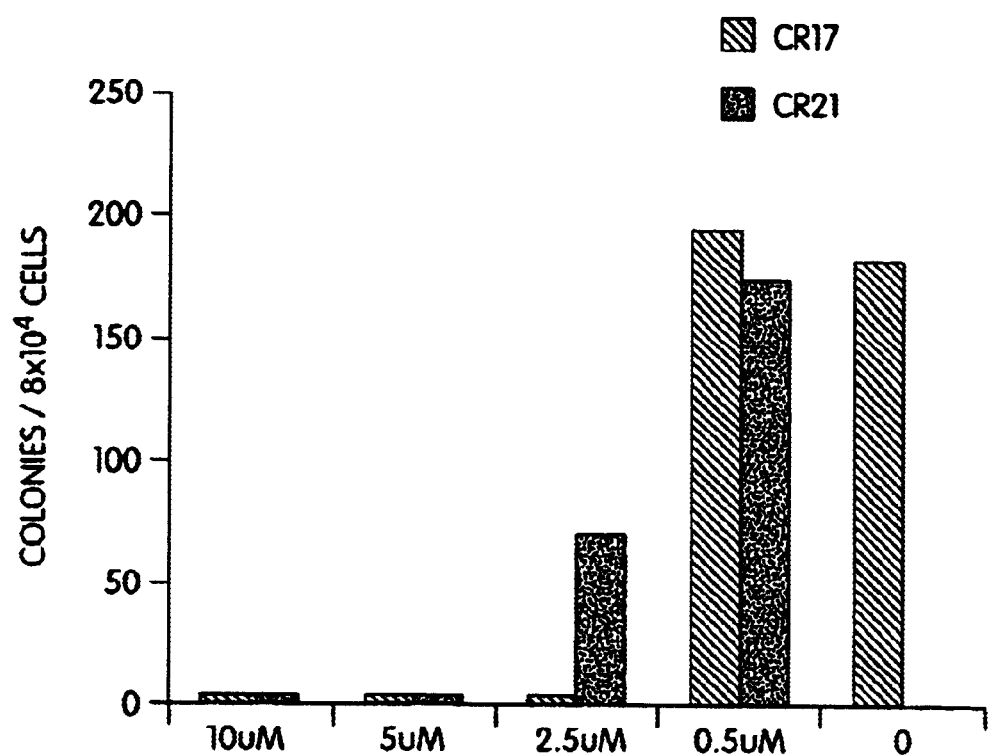
FIG. 8 is a bar graph showing the killing of Philadelphia positive ALL cells by CR17 and CR21 in culture.

The results shown in FIG. 8 demonstrate that CR17 displayed significant inhibition of cell growth at 1–2.5 $\mu$M concentrations. CR21 inhibited cell growth at 5 $\mu$M.

Example 43
Killing of Philadelphia Positive ALL Cells by CR17 and CR21 in Culture ALL cells were plated in 1 ml volumes, in the absence of exogenous growth factors, into 35 mm petri dishes (Nunc, Gibco) containing alpha MEM (Gibco) plus 20% FCS (Cansera Rexdale, ON) in 0.90% (vol/vol) methylcellulose (Fluka, Switzerland) and the indicated concentrations of compound. Cultures were set at 37° C., 5% $CO_2$ in a humidified atmosphere. Colonies consisting of more than 20 cells were counted at 12 days or earlier using an inverted microscope.

Figure 9:
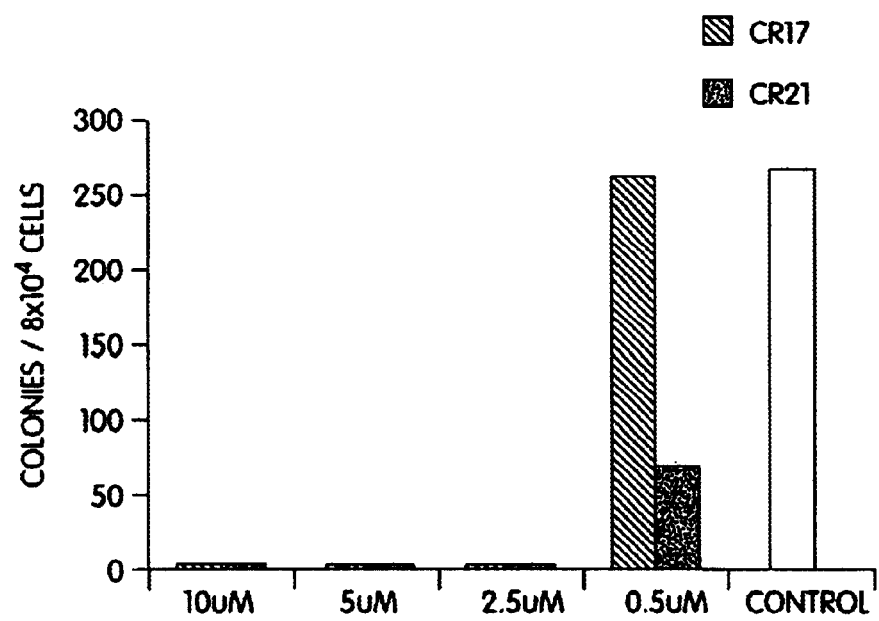
FIG. 9 is a bar graph showing the killing of Philadelphia positive ALL cells by CR17 and CR21 in culture.

The results shown in FIG. 9 demonstrate that CR17 and CR21 both displayed significant inhibition of cell growth at 1–2.5 $\mu$M concentrations.

Example 44
Killing of Philadelphia Positive ALL Cells by CR24 in Culture

ALL cells were plated in 1 ml volumes, in the absence of exogenous growth factors, into 35 mm petri dishes (Nunc, Gibco) containing alpha MEM (Gibco) plus 20% FCS (Cansera Rexdale, ON.) in 0.9% (vol/vol) methylcellulose (Fluka, Switzerland) and the indicated concentrations of CR24. Cultures were set at 37° C., 5% $CO_2$ in a humidified atmosphere. Colonies consisting of more than 20 cells were counted at 9 days or earlier using an inverted microscope.

Figure 10:
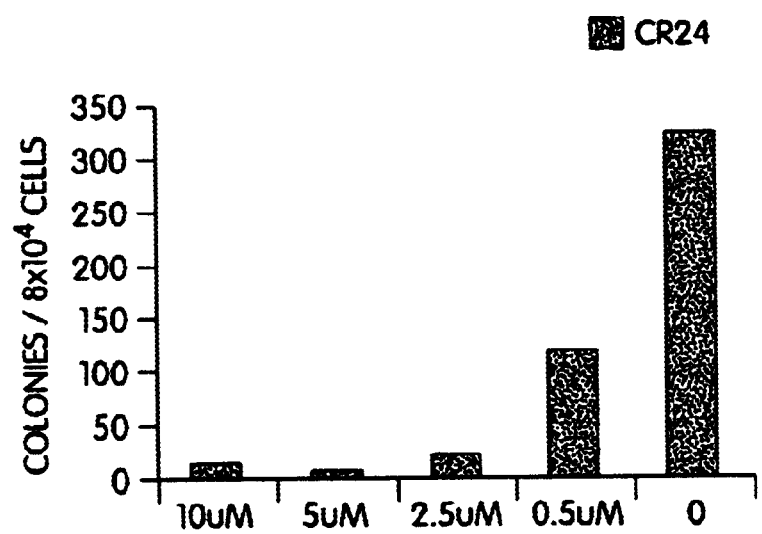
FIG. 10 is a bar graph showing the killing of Philadelphia positive ALL cells by CR24 in culture.

The results shown in FIG. 10 demonstrate that CR24 was effective against Ph+ ALL cells at concentrations as low as 0.5 $\mu$M, demonstrating a virtually complete inhibition of cell growth between 2.5 and 5 $\mu$M.

Example 45
Killing of Philadelphia Positive ALL Cells by CR19 in Culture

ALL cells were plated in 1 ml volumes, in the absence of exogenous growth factors, into 35 mm petri dishes (Nunc, Gibco) containing alpha MEM (Gibco) plus 20% FCS (Cansera Rexdale, ON.) in 0.9% (vol/vol) methylcellulose (Fluka, Switzerland) and the indicated concentrations of CR19. Cultures were set at 37° C., 5% $CO_2$ in a humidified atmosphere. Colonies consisting of more than 20 cells were counted at 9 days or earlier using an inverted microscope.

Figure 11:
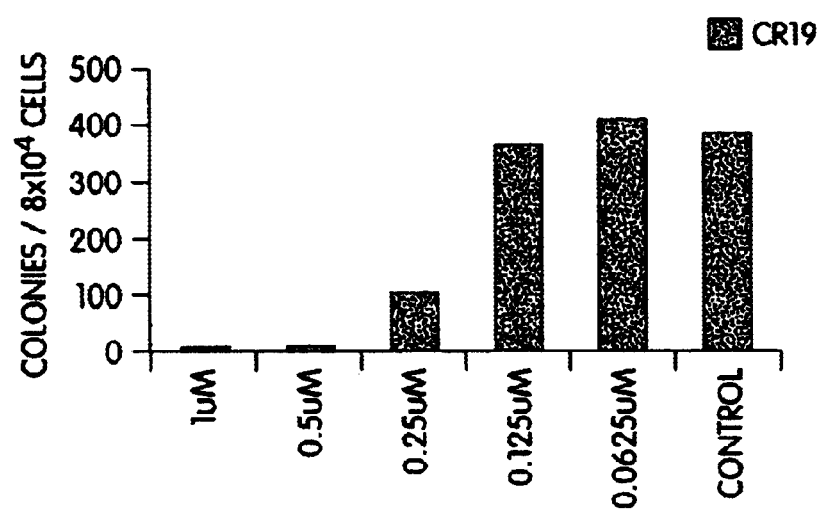
FIG. 11 is a bar graph showing the killing of Philadelphia positive ALL cells by CR19 in culture.

The results shown in FIG. 11 demonstrate that CR19 was highly effective against Ph+ ALL cells at nanomolar concentrations between 250 and 500 mM.

Example 46
Effect of CR19 On Normal Bone Marrow Differentiation in Culture

The CFU-GEMM assay was performed according to Fauser and Messner (1978, Blood, 52(6) 1243–8) and Messner and Fausser (1980, Blut, 41(5) 327–33) with some variations. In brief, heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs. The fractionated BM cells at $2 \times 10^5$ cells/ml were cultured in IMDM (OCl, Toronto) containing 0.9% (vol/vol) methylcellulose supplemented with 30% FCS (Cansera Rexdale, ON.) or normal human plasma, a cocktail of cytokines containing G-CSF (10 ng/ml, Amgen), IL-3 (40 U/ml, Immunex), MGF (50 ng/ml, Immunex), Erythropoietin (2 u/ml, Epprex) or TPO (10 ng/ml, Amgen), $5 \times 10^{-5}$M $\beta$-2-mercaptoethanol and the specified concentrations of CR19. The culture mixture was plated in 1 ml volumes into 35 mm petri dishes and incubated at 37° C., 5% $CO_2$ in a humidified atmosphere. All cultures were evaluated at 14 days for the number of BFU-E colonies (defined as aggregates of more than 500 hemaglobinized cells or, 3 or more erythroid subcolonies) and CFU-C colonies (defined as granulocyte or monocyte-macrophage cells or both).

Figure 12:
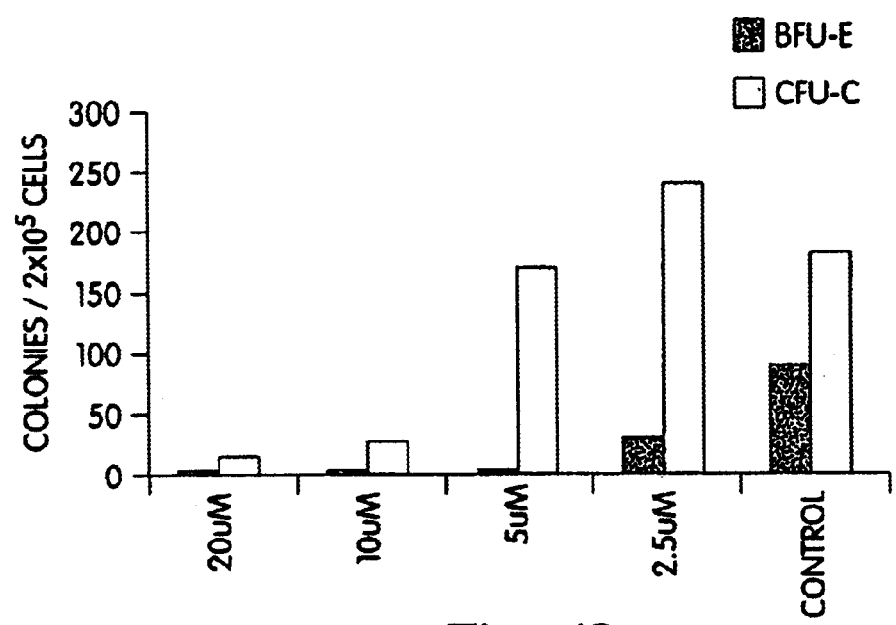
FIG. 12 is bar graph showing the effect of CR19 on normal bone marrow differentiation in culture.

The results shown in FIG. 12 demonstrate that CR19 displayed significant inhibition of the development of BFU-E colonies at 2.5 $\mu$M, although at this concentration it also boosted CFU-C colony formation. At 5 $\mu$M the stimulatory effect disappeared and BFU-E colonies were virtually absent.

Example 47
Effect of CR24, CR17 and CR21 on Normal Bone Marrow Differentiation The CFU-GEMM assay was performed according to Fauser and Messner (1978, Blood, 52(6) 1243–8) and Messner and Fausser (1980, Blut, 41(5) 327–33) with some variations (British Journal of Haematology, 1992, 80, p40–48). In brief, heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs. The fractionated BM cells at $2 \times 10^5$ cells/ml were cultured in IMDM (OCl, Toronto) containing 0.9% (vol/vol) methylcellulose supplemented with 30% FCS (Cansera Rexdale, ON.) or normal human plasma, a cocktail of cytokines containing G-CSF (10 ng/ml, Amgen), IL-3 (40 U/ml, Immunex), MGF (50 ng/ml, Immunex), Erythropoietin (2 u/ml, Epprex) or TPO (10 ng/ml, Amgen), $5 \times 10^{-5}$M β-2-mercaptoethanol and the specified concentration of test compound. The culture mixture was plated in 1 ml volumes into 35 mm petri dishes and incubated at 37° C., 5% $CO_2$, in a humidified atmosphere. All cultures were evaluated at 14 days for the number of BFU-E colonies (defined as aggregates of more than 500 hemoglobinized cells or, 3 or more erythroid subcolonies) and CFU-C colonies (defined as granulocyte or monocyte-macrophage cells or both).

Figure 13:
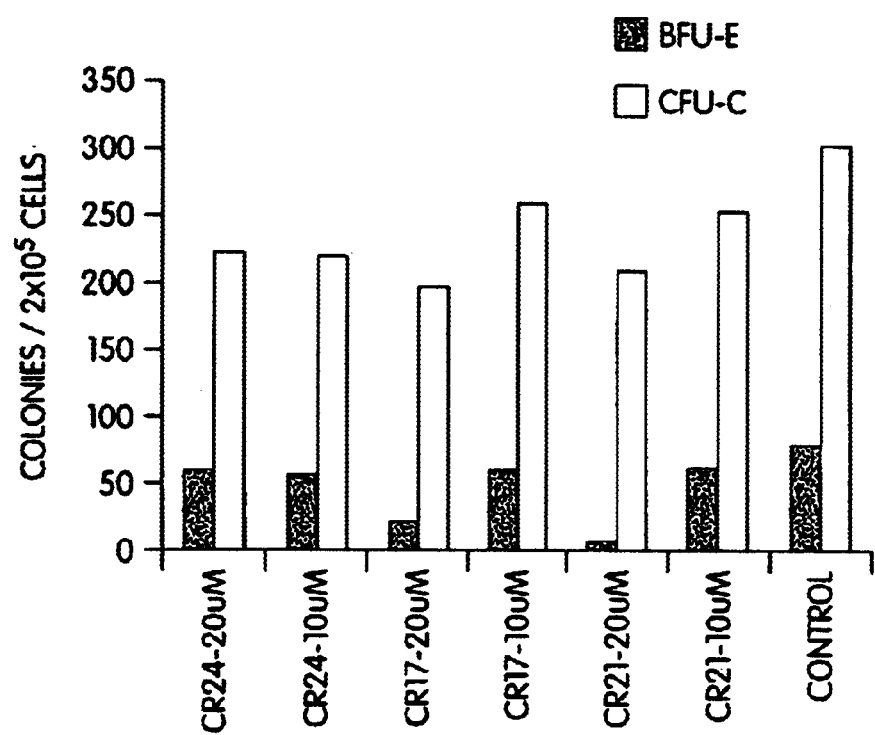
FIG. 13 is a bar graph showing the effect of CR24, CR17 and CR21 on normal bone marrow differentiation.

The results shown in FIG. 13 demonstrate that CR24 displayed minimal inhibition of bone marrow colony formation at either 10 or 20 μM concentrations, whereas both CR17 and CR21 caused inhibition of BFU-E colony formation at the higher 20 μM dose.

Example 48
In vitro Purging of Normal Bone Marrow with CR4

Heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs.

For the purging process, the cells were resuspended at $1 \times 10^6$/ml in complete medium with or without 50 μM CR4. The cells were incubated with the CR4 for two and a half hours at 37° C., 5% $CO_2$. At the end of this period the cells were thoroughly washed in medium to remove CR4 and then cultured at $2 \times 10^5$ cells/ml in IMDM (OCl, Toronto) containing 0.9% (vol/vol) methylcellulose supplemented with 30% FCS (Cansera Rexdale, ON.) or normal human plasma, a cocktail of cytokines containing G-CSF (10 ng/ml, Amgen), IL-3 (40 U/ml, Immunex), MGF (50 ng/ml, Immunex), Etryhropoietin (2 u/ml, Epprex) or TPO (10 ng/ml, Amgen) and $5 \times 10^{-5}$M b-2-mercaptoethanol. The culture mixture was plated in 1 ml volumes into 35 mm petri dishes and incubated at 37° C., 5% $CO_2$ in a humidified atmosphere. All cultures were evaluated at 14 days for the number of BFU-E colonies (defined as aggregates of more than 500 hemoglobinized cells or, 3 or more erythroid subcolonies), CFU-C colonies (defined as granulocyte or monocyte-macrophage cells or both) and CFU-GEMM colonies (a mixed population comprising of all elements).

Figure 14:
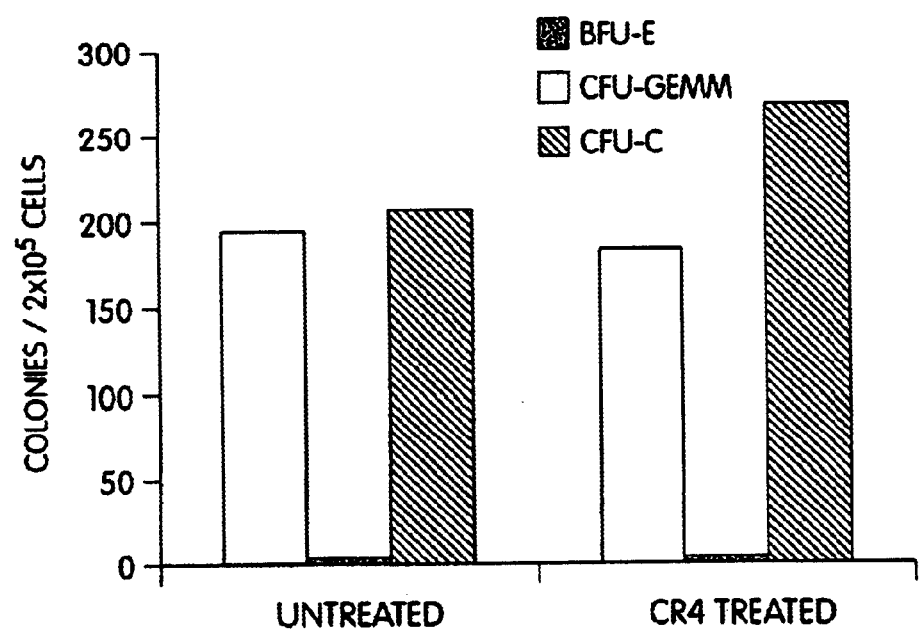
FIG. 14 is a bar graph showing the effect of in vitro purging of normal bone marrow with CR4.

The results shown in FIG. 14 demonstrate that two and a half hours exposure to 50 μM CR4 did not result in significant inhibition of colony formation. While a slight drop in BFU-E colonies occurred, CFU-C colony numbers actually increased significantly.

Example 49
In Vitro Purging of Z119 Acute Lymphoblastic Leukemia with CR4

For the purging assay, the cells were resuspended in complete medium with or without CR4 as indicated and incubated at 37° C., 5% $CO_2$ for 0–5 hours. Cells were then washed thoroughly with medium to remove the CR4, resuspended and plated in 1 ml volumes, in the absence of exogenous growth factors, into 35 mm petri dishes (Nunc, Gibco) containing alpha MEM (Gibco) plus 20% FCS (Cansera Rexdale, ON.) in 0.9% (vol/vol) methylcellulose (Fluka, Switzerland). Cultures were set at 37° C., 5% $CO_2$ in a humidified atmosphere. Colonies consisting of more than 20 cells were counted at 9 days or earlier using an inverted microscope.

Figure 15:
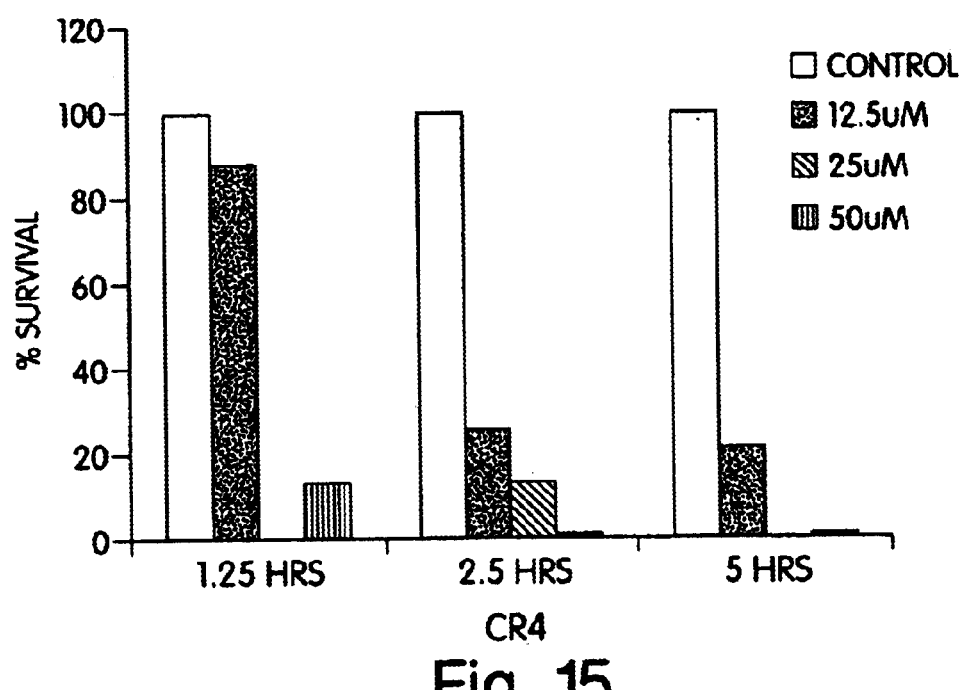
FIG. 15 is a bar graph showing the effect of in vitro purging of Z119 acute lymphoblastic leukemia with CR4.

The results shown in FIG. 15 demonstrate that CR4 demonstrated rapid killing of Z119 cells at the concentrations examined. 50 μM CR4 displayed a complete inhibition after only 2.5 hours exposure, while 85% killing could be achieved with 25 μM CR4 over the same time period. A longer five hour exposure of the cells to 25 μM CR4 resulted in a complete ablation of subsequent cell growth.

Example 50
In vitro Purging of OCl-Ly2 Lymphoma Cells with CR4

For the purging assay, the cells were resuspended in complete medium with or without CR4 as indicated and incubated at 37° C., 5% $CO_2$ for 0–5 hours. Cells were then washed thoroughly with medium to remove CR4, resuspended and plated in 1 ml volumes at $5 \times 10^3$ cells/ml, in the absence of exogenous growth factors, into 35 mm petri dishes (Nunc, Gibco) containing IMDM (OCl, Toronto) plus 20% human cord blood plasma in 0.9% (vol/vol) methylcellulose (Fluka, Switzerland). Cultures were set at 37° C., 5% $CO_2$ in a humidified atmosphere. Colonies consisting of more than 20 cells were counted at 5 days or earlier using an inverted microscope.

Figure 16:
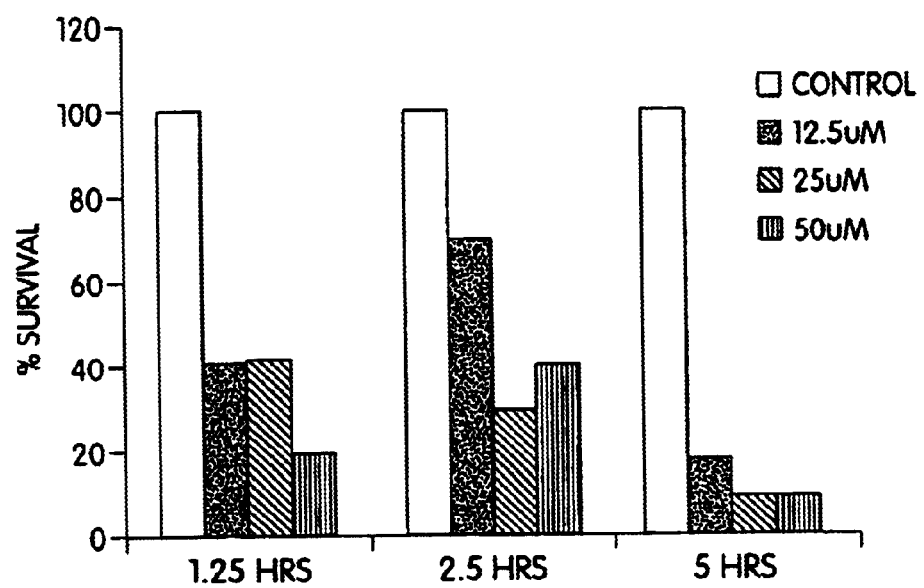
FIG. 16 is a bar graph showing the effect of In vitro purging of OCl-Ly2 lymphoma cells with CR4.

The results shown in FIG. 16 demonstrate that CR4 demonstrated significant killing (90%) of OCl-Ly2 cells at 25–50 μM after only 5 hours exposure. The lower 12.5 μM dose tested also achieved significant killing in the same time period.

Example 51
In vitro Purging of OCl-AML-3 Acute Meyloid Leukemia Cells with CR4

For the purging assay, the cells were resuspended in complete medium with or without CR4 as indicated and incubated at 37° C., 5% $CO_2$ for 0–5 hours. Cells were then washed thoroughly with medium to remove CR4, resuspended and plated in 1 ml volumes at $5 \times 10^3$ cells/ml, in the absence of exogenous growth factors, into 35 mm petri dishes (Nunc, Gibco) containing alpha MEM (Gibco) plus 10% FCS (Cansera Rexdale, ON.) in 0.9% (vol/vol) methylcellulose (Fluka, Switzerland). Cultures were set at 37° C., 5% $CO_2$ in a humidified atmosphere. Colonies consisting of more than 20 cells were counted at 5 days or earlier using an inverted microscope.

Figure 17:
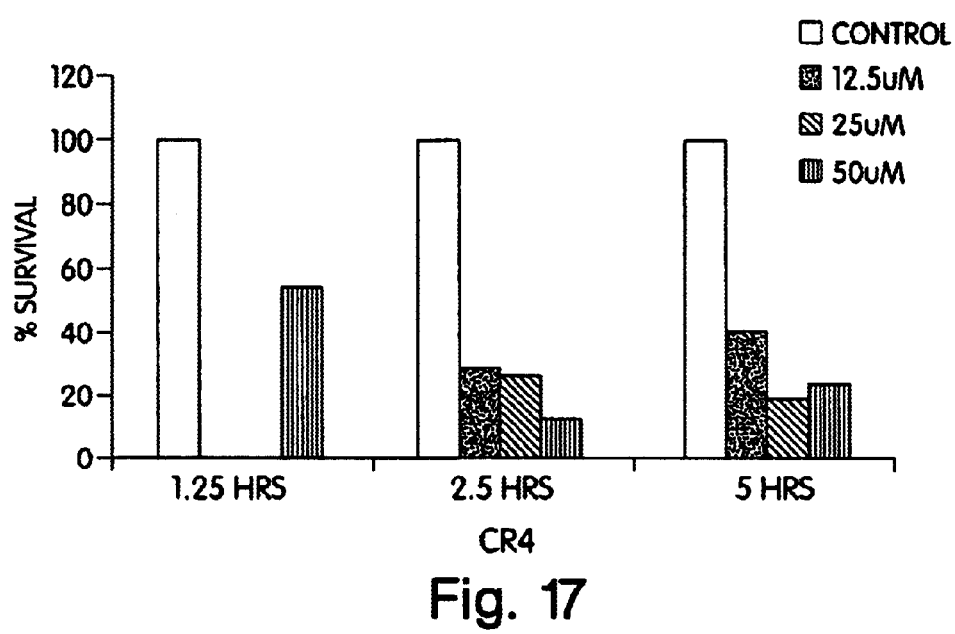
FIG. 17 is a bar graph showing the effect of in vitro purging of OCl-AML-3 acute meyloid leukemia cells with CR4.

The results shown in FIG. 17 demonstrate that CR4 demonstrated significant killing of OCl-AML-3 cells at 50 μM after only 2.5–5 hours exposure. The lower 25 μM dose tested also achieved significant killing in the same time period.

Example 52
In vitro Purging of Ramos B Cell Burkitt's Lymphoma Cells with CR4

For the purging assay, the cells were resuspended in complete medium with or without CR4 as indicated and incubated at 37° C., 5% $CO_2$ for 0–5 hours. Cells were then washed thoroughly with medium to remove the CR4, resuspended and plated in 1 ml volumes, in the absence of exogenous growth factors, into 35 mm petri dishes (Nunc, Gibco) containing RPMI 1640 (Gibco) plus 10% FCS (Cansera Rexdale, ON.) in 0.9% (vol/vol) methylcellulose (Fluka, Switzerland). Cultures were set at 37° C., 5% $CO_2$ in a humidified atmosphere. Colonies consisting of more than 20 cells were counted at 12 days or earlier using an inverted microscope.

Figure 18:
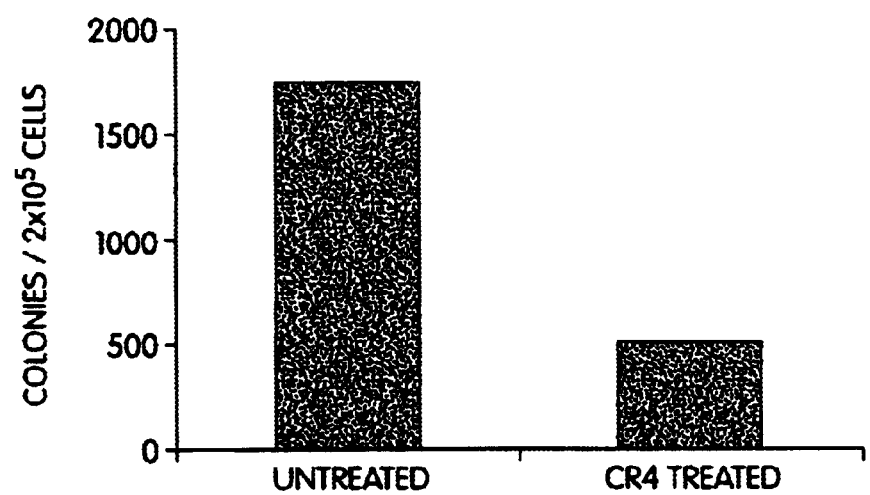
FIG. 18 is a bar graph showing the effect of in vitro purging of Ramos B cell Burkitt's lymphoma cells with CR4.

The results shown in FIG. 18 demonstrate that CR4 demonstrated significant killing (70%) of Ramos cells at 50 µM after 5 hours exposure.

Example 53
Killing of HuNS1 Multiple Myeloma by CR4

HuNS1 cells were plated in 35 mm petri dishes (Nunc, Gibco) in 1 ml volumes at a density of $1\times10^4$ cells/ml, in the absence of exogenous growth factors, containing alpha MEM plus 20% FCS (Cansera, Rexdale Ont.), and 0.9% (vol/vol) methylcellulose (Fluka, Switzerland) and the indicated concentrations of CR4. Cell cultures were incubated in a humidified atmosphere at 37° C. with 5% $CO_2$. Colonies containing more than 20 cells were scored, using an inverted microscope, at 56 days.

Figure 19:
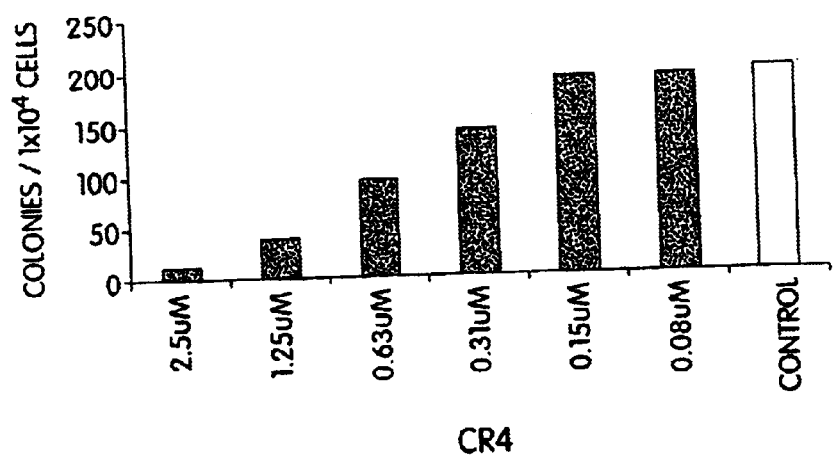
FIG. 19 is a bar graph showing the killing of HuNS1 multiple myeloma cells by low-dose CR4 in culture.

The results shown in FIG. 19 demonstrate that CR4 significantly inhibited cell proliferation and survival at high nanomolar to low micromolar doses (>90% at 2.5 µM). CR4 has no effect upon normal cells at equivalent concentrations.

Example 54
In vivo Treatment of Philadelphia Positive Acute Lymphoblastic Leukemia in NOD-SCID Mice NOD-SCID mice were irradiated (350 rads) and injected with $5\times10^6$ Philadelphia positive Z119 Acute lymphoblastic leukemia cells. After 24 hours Alzet micro-osmotic pumps (Alza Corp. Paolo Alto, Calif.) were implanted subcuntaneously, containing either 20 mM solution of CR4 in 50% DMSO/medium or 50% DMSO/medium alone. Alzet 2001 pumps were utilized, holding a total volume of 200 µl and releasing 1 µl per hour over 7–10 days. Pumps were replaced after 7 days. Each mouse received a daily dose of 0.154 mg of CR4.

After 14 (FIG. 20A) and 21 (FIG. 20B) days mice were sacrificed and bone marrow extracted from the fore and hind limbs. Single cell suspensions were prepared, red blood cells lysed and the samples stained with PE-labelled isotype, anti-human $CD_{19}$ and anti-human HLA-DR antibodies to detect the presence of Z119 cells. These antibodies do not cross react with murine cells.

At d14, bone marrow cell cultures were also performed to assess the presence of Z119 cells $5\times10^4$ BM cells were cultured in IMDM (OCl, Toronto) containing 0.9% (vol/vol) methylcellulose supplemented with 30% serum consisting of a 1:1 mixture of FCS (Cansera Rexdale, ON.) and normal human plasma. No cytokines are added. Under these conditions there is no growth of murine cells. The culture mixture was plated in 1 ml volumes into 35 mm petri dishes and incubated at 37° C., 5% $CO_2$ in a humidified atmosphere. All cultures were evaluated at 9 days for the number of ALL colonies.

Figure 20A:
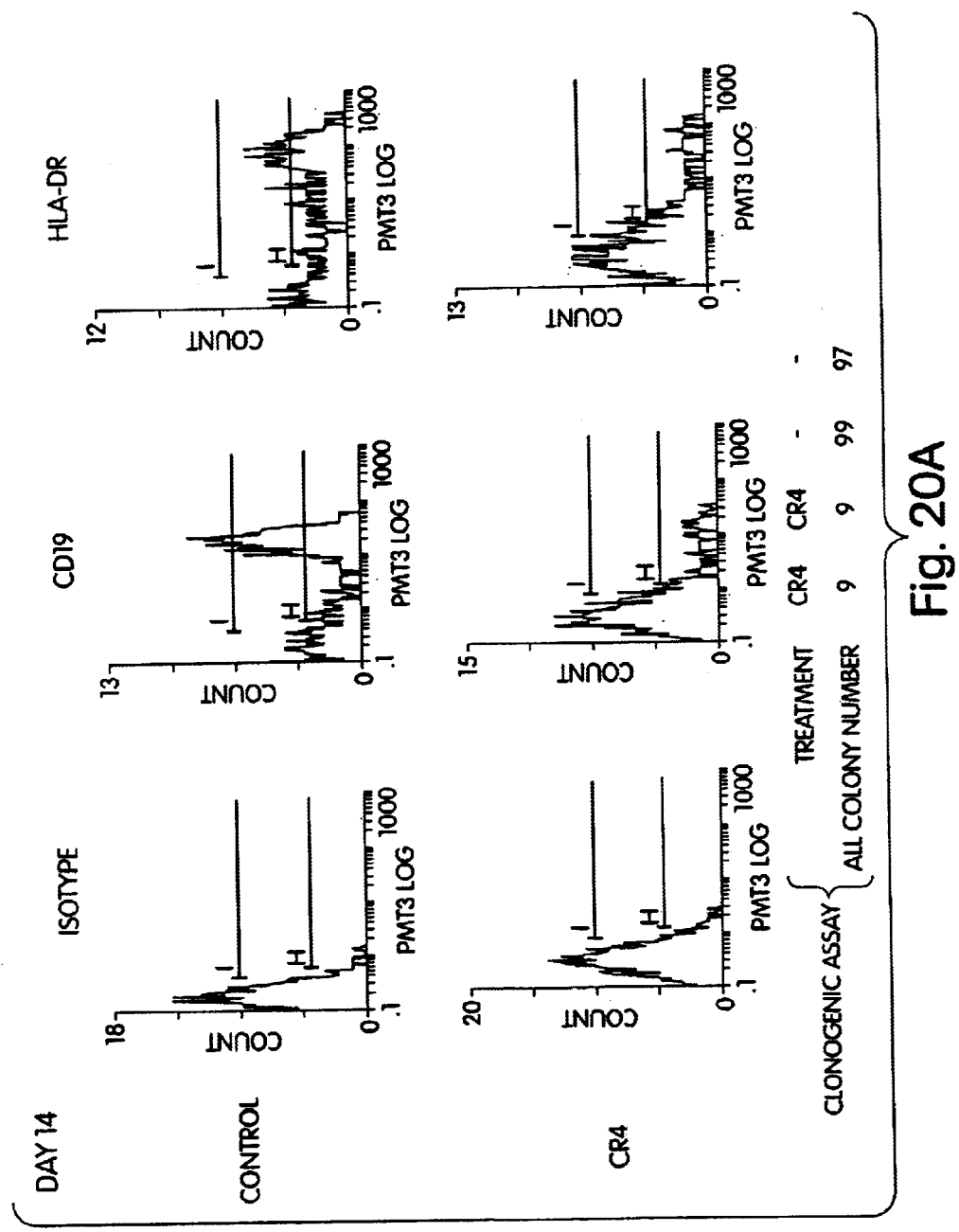
FIGS. 20A and B are graphs showing cell staining after in vivo treatment of Philadelphia positive acute lymphoblastic leukemia in NOD-SCID mice.
Figure 20B:
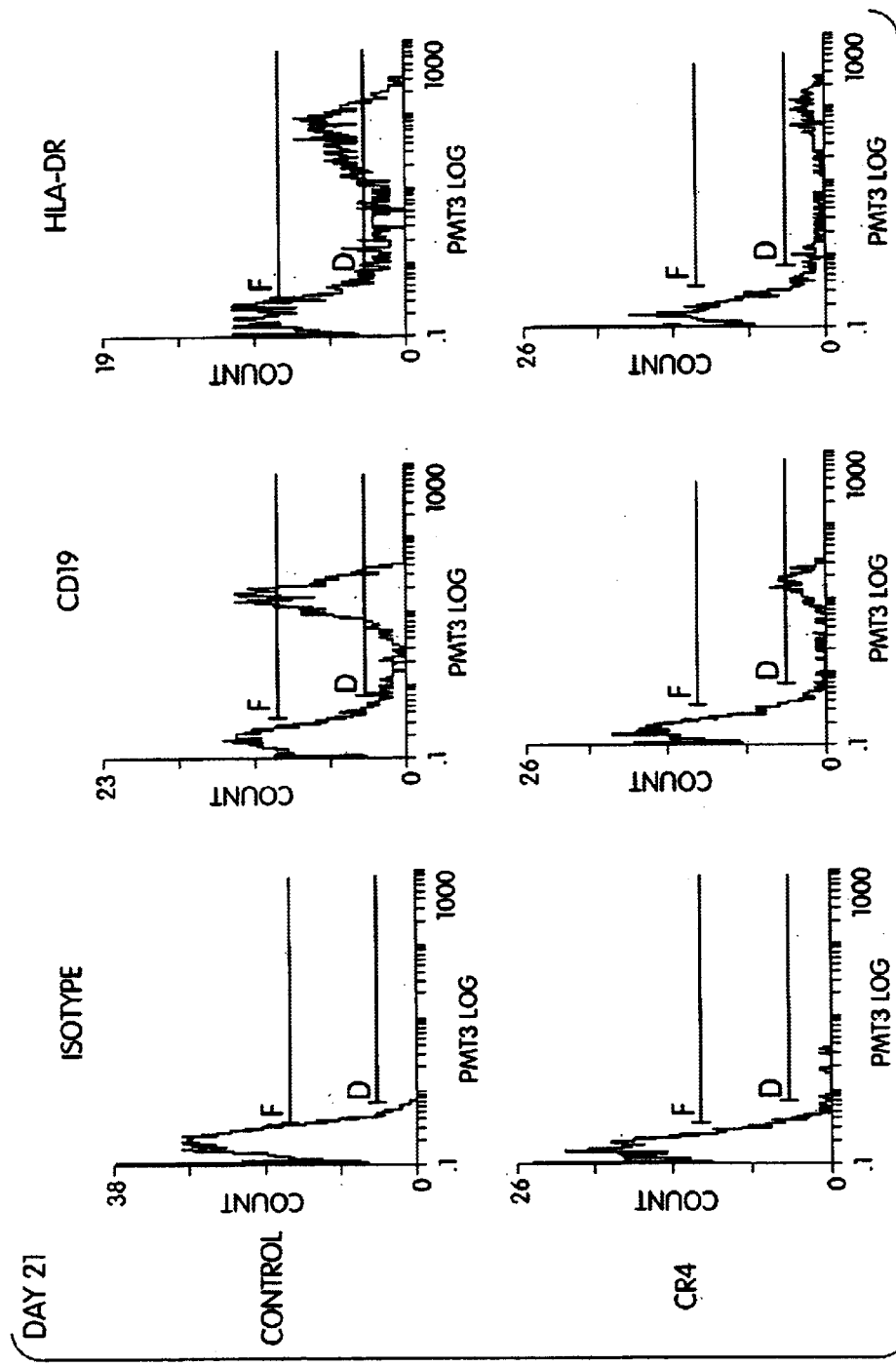

The results shown in FIGS. 20A and 20B demonstrate that at both day 14 and 21 sacrifices, a significant reduction in ALL infiltration of the bone marrow was observed in all the mice treated with CR4 relative to the OMSO treated control mice.

In control animals, massive infiltration of the spleen, liver and kidney was observed, as well as the presence of ALL cells in the peripheral blood. In addition to a 90% reduction in the infiltration of ALL cells into the bone marrow, treatment with CR4 reduced ALL infiltration of the organs and blood to below detectable levels.

Thus, CR4 was highly effective against a variety of cancer cells, including acute lymphoblastic leukemia, Philadelphia positive ALL, acute myeloid leukemia, myeloma and B-lineage lymphoma, at concentrations ranging from 50 nM to 5 µM. At the same time, minimal toxicity was seen when normal cells were incubated in the presence of CR4 until concentrations of 10–20 µM or greater were achieved. CR4 was particularly active against bcr-abl transformed Philadelphia positive cells, achieving >90% wipeout at concentrations as low as 40 nM. CR4 was also highly effective in high dose (25–50 µM) in vitro purging assays against Philadelphia positive ALL, AML and lymphoma, causing >90% inhibition of growth with a 2.5 to 5 hour exposure time. Over identical doses and times normal bone marrow growth and differentiation were unaffected. CR4 showed a combination of high level toxicity to cancer cells with minimal non-specific cytotoxic damage.

CR4 was also highly effective in a whole animal model (Example 54). The compound demonstrated good retention characteristics, still being detectable in the blood 30 minutes after I.V. injection. In a murine model of human Ph+ ALL, CR4 caused a greater than 90 percent reduction in ALL infiltration of bone marrow within a two week period, reducing the presence of infiltrating ALL cells in liver, kidney, spleen and peripheral blood below detection level. In contrast, control mice treated with vehicle alone demonstrated massive infiltration of all these organs. No evidence of non-specific toxicity was observed.

Example 55
In vitro Purging of Normal Bone Marrow with CR11

Heparinized bone marrow cells were layered over Percoll (1.077 gm/ml) (Pharmacia Fine Chemical, Piscataway N.J.) and centrifuged at 400 g at 4° C. for 10 minutes to remove neutrophils and RBCs.

For the purging process, the cells were resuspended at $1\times10^6$/ml in complete medium with or without 50 µM CR11. The cells were incubated with the tryrphostin for seven hours at 37° C., 5% $CO_2$. At the end of this period the cells were thoroughly washed in medium to remove CR11 and then cultured at $2\times10^5$ cells/ml in IMDM (OCl, Toronto) containing 0.9% (vol/vol) methylcellulose supplemented with 30% FCS (Cansera Rexdate, ON.) or normal human plasma, a cocktail of cytokines containing G-CSF (10 ng/ml, Amgen), IL-3 (40 U/ml, Immunex), MGF (50 ng/ml, Immunex), Erythropoietin (2 u/ml, Epprex) or TPO (10 ng/ml, Amgen) and $5\times10^{-5}$M β-2-mercaptoethanol. The culture mixture was plated in 1 ml volumes into 35 mm petri dishes and incubated at 37° C., 5% $CO_2$ in a humidified atmosphere. All cultures were evaluated at 14 days for the number of BFU-E colonies (defined as aggregates of more than 500 hemoglobinized cells or, 3 or more erythroid subcolonies), CFU-C colonies (defined as granulocyte or monocyte-macrophage cells or both) and CFU-GEMM colonies (a mixed population comprising of all elements).

Figure 21:
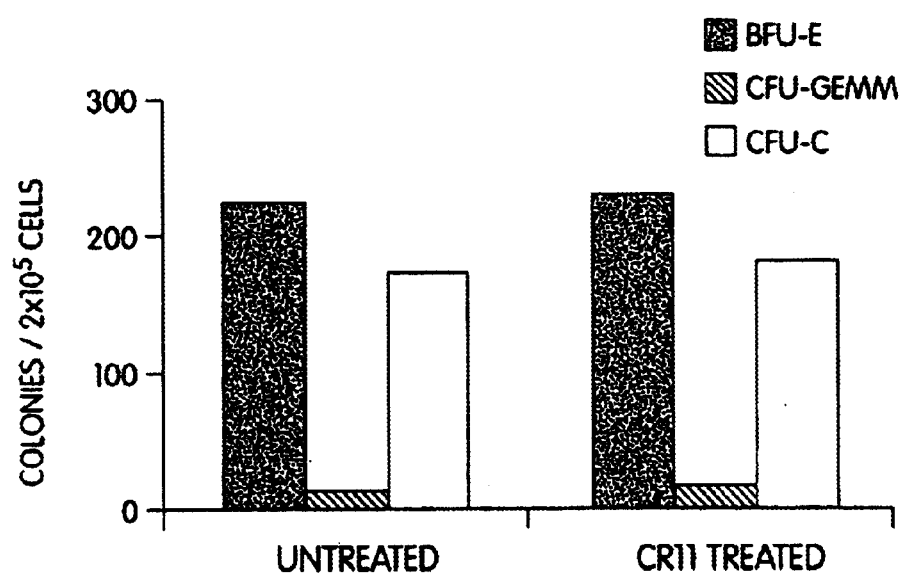
FIG. 21 is a bar graph showing that the effect of in vitro purging of normal bone marrow with CR11.

The results shown in FIG. 21 demonstrate that seven hours exposure to 50 µM CR11 did not result in any significant inhibition of colony formation. BFU-E, CFU-GEMM and CFU-C colonies were all normal.

Example 56
In vitro Purging of Philadelphia Positive Acute Lymphoblastic Leukemia with CR11

For the purging assay, the cells were resuspended in complete medium with or without CR11 as indicated and incubated at 37° C., 5% $CO_2$ for 0–7 hours. Cells were then washed thoroughly with medium to remove the CR11, resuspended and plated in 1 ml volumes, in the absence of exogenous growth factors, into 35 mm petri dishes (Nunc, Gibco) containing alpha MEM (Gibco) plus 20% FCS (Cansera Rexdale, ON.) in 0.9% (vol/vol) methylcellulose (Fluka, Switzerland). Cultures were set at 37° C., 5% $CO_2$ in a humidified atmosphere. Colonies consisting of more than 20 cells were counted at 9 days or earlier using an inverted microscope.

Figure 22:
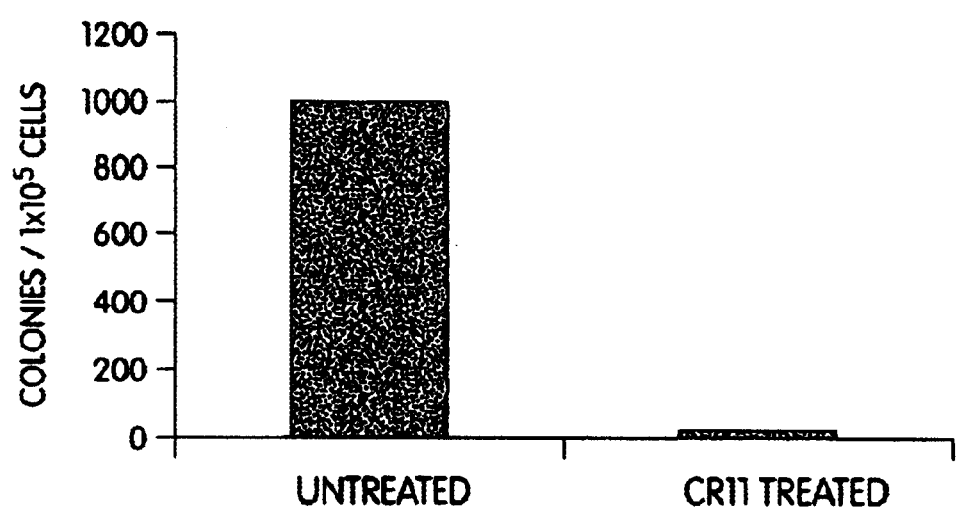
FIG. 22 is a bar graph showing that the effect of in vitro purging of Philadelphia positive acute lymphoblastic leukemia with CR11.

The results shown in FIG. 22 demonstrate that CR11 demonstrated complete killing of Ph+ ALL cells at 50 $\mu$M after 7 hours exposure.

Example 57
Philadelphia (Ph+) ALL Lines Z119 and Z181 (5×10⁶ Cells/point) Were Lysed and Immunoprecipitated with Bcr-Abl Antibody The precipitates were washed twice with lysis buffer and once with kinase assay buffer, and resuspended in same buffer containing varying concentrations of CR4. The precipitates were incubated with the drug for 10 min at room temperature, followed by addition of 10 $\mu$Ci $^{33}$P$\gamma$ATP. The reaction was stopped after 20 min by the addition of SDS-PAGE reducing sample buffer and separated on an 8–16% SDS-PAGE gel. The products were transferred onto nitrocellulose membrane and visualized by autoradiography.

Figure 23:
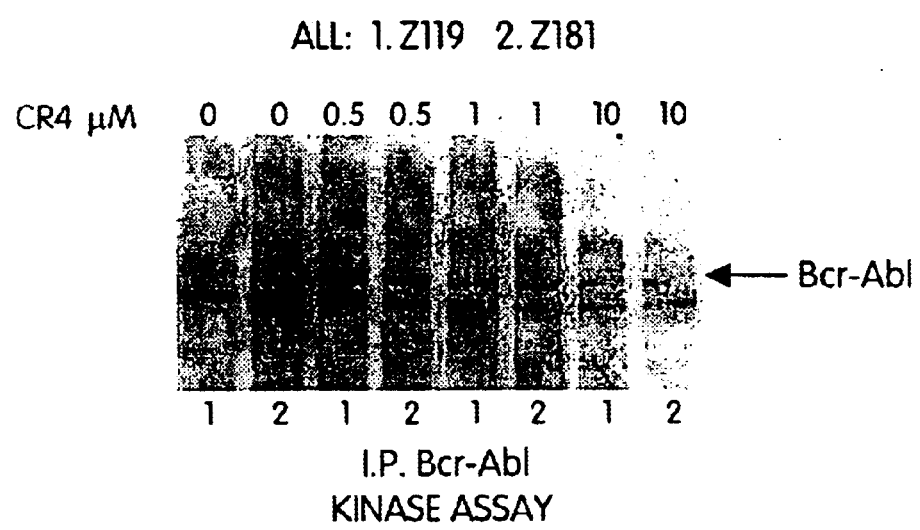
FIG. 23 is an autoradiograph which shows Philadelphia (Ph+) ALL lines Z119 and Z181 ($5 \times 10^6$ cells/point) immunoprecipitated with Bcr-Abl antibody.

The results shown in FIG. 23 demonstrate that Bcr-Abl kinase activity is effectively blocked at concentrations of 1 to 10 $\mu$M of the CR4 compound in both Z199 and Z181 ALL cell lines.

Example 58
Philadelphia (Ph+) ALL Line Z119 (5×10⁶ Cells/point) was Preincubated for 5 Hours with Different Concentrations of CR4 and Immunoprecipitated with Jak2 Antibody The cells were lysed in lysis buffer and immunoprecipitated with Jak2 antibody. The precipitates were washed twice with lysis buffer and once with kinase assay buffer, followed by addition of 10 $\mu$Ci $^{33}$P$\gamma$ATP. The reaction was stopped after 20 min by the addition of SDS-PAGE reducing sample buffer and separated on an 8–16% SDS-PAGE gel. The products were transferred onto nitrocellulose membrane and visualized by autoradiography.

Figure 24:
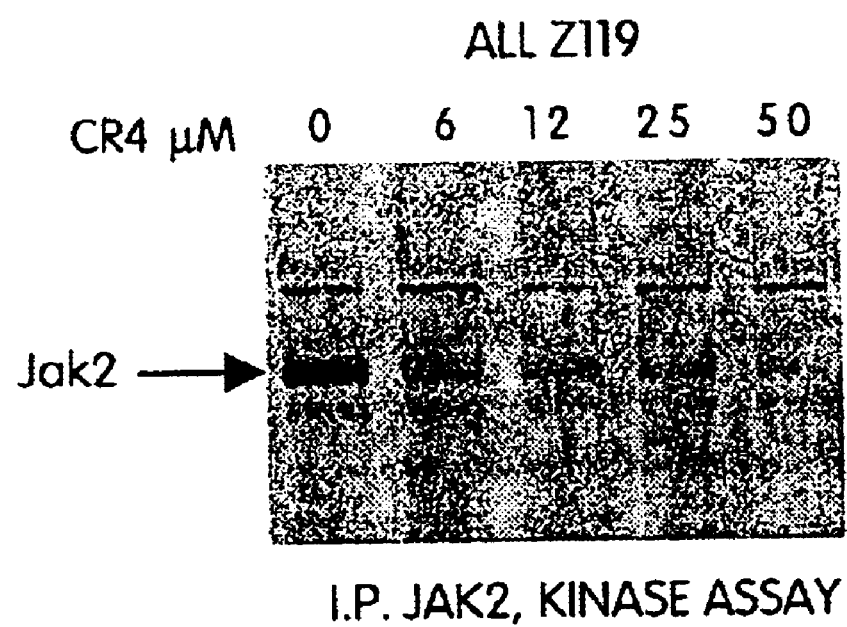
FIG. 24 is an autoradiograph which shows Philadelphia (Ph+) ALL line Z119 ($5 \times 10^6$ cells/point) immunoprecipitated with Jak2 antibody.

The results shown in FIG. 24 demonstrate that Jak2 kinase activity was dramatically inhibited at a concentration of 6 $\mu$M and further blocked at higher concentrations.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A pharmaceutical composition comprising a compound selected from:
    (E,E)-2-(benzylaminocarbonyl)-3-(3,4-dihydroxystyryl) acrylontrile (CR4);
    (E,E)-2-(3,4-dihydroxybenzylaminocarbonyl)-3-(3,5-dimethoxy-4-hydroxystyryl)acrylonitrile (CR11);
    (E,E)-2-aminocarbonyl-3-(3,4-dihydroxystyryl) acrylonitrile (CR17);
    (E,E)-2-(3,4-dihydroxybenzylaminocarbonyl)-3-styrylacrylonitrile (CR19);
    (E,E)-2-(3,4-dihydroxybenzylaminocarbonyl)-3-(3,4-dihydroxystyryl)acrylonitrile (CR21); and
    (E,E)-2-(β-ethanolaminocarbonyl)-3-(3,5-dimethoxy-4-hydroxystyryl)acrylonitrile (CR24).

2. A pharmaceutical composition comprising a pharmaceutically acceptable diluent or carrier and (E,E)-2-(benzylaminocarbonyl)-3-(3,4-dihydroxystyryl) acrylonitrile (CR4).

3. A pharmaceutical composition comprising a pharmaceutically acceptable diluent or carrier and (E,E)-2-(3,4-dihydroxybenzylaminocarbonyl)-3-(3,5-dimethoxy-4-hydroxystyryl)acrylonitrile (CR11).

4. A pharmaceutical composition comprising a pharmaceutically acceptable diluent or carrier and (E,E)-2-(3,4-dihydroxybenzylaminocarbonyl)-3-styrylacrylonitrile (CR19).

5. A method of modulating cell proliferation comprising administering to a cell or animal in need thereof an effective amount of a compound of Formula I, or a salt, solvate or hydrate thereof;

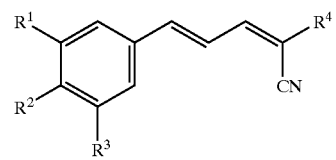

wherein $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$ and halo;

$R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl($C_{1-6}$alkyl), $NO_2$, halo and $CH_2$—S—$(CH_2)_n$Ar;

$R^4$ is selected from the group consisting of $C(X)R^5$, $SO_3Ar$, $NH_2$, NH—$C_{1-6}$alkyl, N($C_{1-6}$alkyl)($C_{1-6}$alkyl), $P(O)(OH)_2$, $P(O)(OC_{1-6}alkyl)_2$, and $C(NH_2)$—$C(CN)_2$;

X is selected from O, S, NH and N—$C_{1-6}$alkyl;

$R^5$ is selected from the group consisting of $NH_2$, OH, $NH(CH_2)_nAr$, $NH(CH_2)_nOH$, $(CH_2)_nOC_{1-6}$alkyl, $C_{1-6}$alkyl, $C_{1-6}$alkoxy, $NHNH_2$, $NHC(O)NH_2$, NHC(O)$C_{1-6}$alkoxy, N-morpholino and N-pyrrolidino; and Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl, SH, S—$C_{1-6}$alkyl, $NO_2$, $CF_3$, $OCF_3$ and halo;

n is 0 to 4; and p is 1–4.

6. A method of inhibiting cell proliferation comprising administering to a cell or animal in need thereof an effective amount of a compound of a Formula I, or a salt, solvate or hydrate thereof:

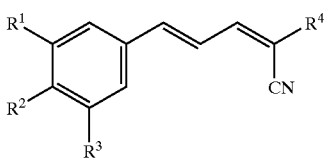

wherein
- $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;
- $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;
- $R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}$alkyl$)_2$, and $C(NH_2)$=$C(CN)_2$;
- X is selected from O, S, NH and N—$C_{1-6}$alkyl;
- $R^5$ is selected from the group consisting of $NH_2$, OH, $NH(CH_2)_n$Ar, $NH(CH_2)_n$OH, $(CH_2)_n OC_{1-6}$alkyl, $C_{1-6}$alkyl, $C_{1-6}$alkoxy, $NHNH_2$, $NHC(O)NH_2$, $NHC(O)C_{1-6}$alkoxy, N-morpholino and N-pyrrolidino; and
- Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;
- n is 0 to 4; and
- p is 1–4.

7. The method of claim 6, wherein the cell proliferation that is inhibited is cancer cell proliferation.

8. The method of claim 7, wherein said cancer is a hematopoietic cell cancer.

9. The method of claim 7, wherein said cancer is a leukemia, a lymphoma, a myeloma or a carcinoma.

10. The method of claim 9, wherein said cancer is a leukemia selected from acute lymphoblastic leukemia, Philadelphia+ leukemia, Philadelphia+ leukemia, acute myelocytic leukemia, chronic myeloid leukemia, chronic lymphocytic leukemia or juvenile myelomonocyte leukemia.

11. The method of claim 10, wherein said leukemia is acute lymphoblastic leukemia.

12. A method of inhibiting hematopoietic cancer cell proliferation, comprising administering to a cell or animal in need thereof an effective amount of a compound of Formula I, or a salt, solvate or hydrate thereof:

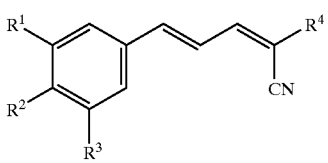

wherein
- $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;
- $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;
- $R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}$alkyl$)_2$, and $C(NH_2)$=$C(CN)_2$;
- X is selected from O, S, NH and N—$C_{1-6}$alkyl;
- $R^5$ is selected from the group consisting of $NH_2$, OH, $NH(CH_2)_n$Ar, $NH(CH_2)_n$OH, $(CH_2)_n OC_{1-6}$alkyl, $C_{1-6}$alkyl, $C_{1-6}$alkoxy, $NHNH_2$, $NHC(O)NH_2$, $NHC(O)C_{1-6}$alkoxy, N-morpholino and N-pyrrolidino; and
- Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;
- n is 0 to 4; and
- p is 1–4.

13. A method of inhibiting cancer cell proliferation, wherein said cancer is a leukemia, a lymphoma, a myeloma or a carcinoma, comprising administering to a cell or animal in need thereof an effective amount of a compound of Formula I, or a salt, solvate or hydrate thereof:

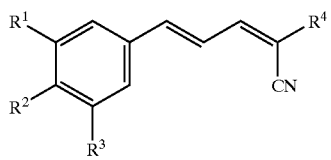

wherein
- $R^1$ and $R^2$ are each independently selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, $CF_3$, $OCF_3$ and halo;
- $R^3$ is selected from the group consisting of H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, O—Si($C_{1-6}$alkyl)($C_{1-6}$alkyl)($C_{1-6}$alkyl), $NO_2$, halo and $CH_2$—S—$(CH_2)_n$Ar;
- $R^4$ is selected from the group consisting of $C(X)R^5$, $SO_3$Ar, $NH_2$, NH—$C_{1-6}$alkyl, N($C_{1-6}$alkyl)($C_{1-6}$alkyl), $P(O)(OH)_2$, $P(O)(OC_{1-6}$alkyl$)_2$, and $C(NH_2)$=$C(CN)_2$;
- X is selected from O, S, NH and N—$C_{1-6}$alkyl;
- $R^5$ is selected from the group consisting of $NH_2$, OH, $NH(CH_2)_n$Ar, $NH(CH_2)_n$OH, $(CH_2)_n OC_{1-6}$alkyl, $C_{1-6}$alkyl, $C_{1-6}$alkoxy, $NHNH_2$, $NHC(O)NH_2$, $NHC(O)C_{1-6}$alkoxy, N-morpholino and N-pyrrolidino; and
- Ar is an aromatic or heteroaromatic group, unsubstituted or substituted with 1–4 substituents, independently selected from the group consisting of OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo;
- n is 0 to 4; and
- p is 1–4.

14. A method according to claim 13, wherein said cancer is a leukemia selected from acute lymphoblastic leukemia, aggressive Philadelphia+ leukemia, acute myelocytic leukemia, chronic myeloid leukemia, chronic lymphocytic leukemia or juvenile myelomonocyte leukemia.

15. A method according to claim 14, wherein said leukemia is acute lymphoblastic leukemia.

16. A pharmaceutical composition comprising a pharmaceutically acceptable diluent or carrier and (E,E)-2-carboxy-3-(3,4-dihydroxystyryl)acrylonitrile.

17. A compound selected from:
(E,E)-2-(benzylaminocarbonyl)-3-(3,4-dihydroxystyryl) acrylonitrile (CR4);
(E,E)-2-(3,4-dihydroxybenzylaminocarbonyl)-3-(3,5-dimethoxy-4-hydroxystyryl)acrylonitrile (CR11);
(E,E)-2-aminocarbonyl-3-(3,4-dihydroxystyryl) acrylonitrile (CR17);
(E,E)-2-(3,4-dihydroxybenzylaminocarbonyl)-3-styrylacrylonitrile (CR19);
(E,E)-2-(3,4-dihydroxybenzylaminocarbonyl)-3-(3,4-dihydroxystyryl)acrylonitrile (CR21); and
(E,E)-2-(β-ethanolaminocarbonyl)-3-(3,5-dimethoxy-4-hydroxystyryl)acrylonitrile (CR24).

18. A compound (E,E)-2-benzylaminocarbonyl)-3-(3,4-dihydroxystyryl)acrylonitrile (CR4).

19. A compound (E,E)-2-(3,4-dihydroxybenzylaminocarbonyl)-3-(3,5-dimethoxy-4hydroxystyryl)acrylonitrile (CR11).

20. A compound (E,E)-2-(3,4-dihydroxybenzylaminocarbonyl)-3-styrylacrylonitrile (CR19).

21. A compound (E,E)-2-carboxy-3-(3,4-dihydroxystyryl)acrylonitrile.

22. The compound (E,E)-2-carboxy-3-(3,5-dimethoxy-4-hydroxystyryl)acrylonitrile (CR-14).

* * * * *

UNITED STATES PATENT AND TRADEMARK OFFICE
CERTIFICATE OF CORRECTION

PATENT NO. : 6,800,659 B2
DATED : October 5, 2004
INVENTOR(S) : Roifman et al.

It is certified that error appears in the above-identified patent and that said Letters Patent is hereby corrected as shown below:

Column 44,
Line 37, please replace "$N(C_{1-6}alkyl)(C_{1-6}alkyl,$" with -- $N(C_{1-6}alkyl)(C_{1-6}alkyl)$, --;
Line 39, please insert -- , $OCF_3$ -- after "$CF_3$";
Line 43, please replace "$(C_{1-6}alkyl(C_{1-6}alkyl),$" with -- $(C_{1-6}alkyl)(C_{1-6}alkyl)$, --;
Line 47, please replace "$C(NH_2)$—$C(CN)_2$;" with -- $C(NH_2)=C(CN)_2$; --;
Line 52, please replace "$NH(CH_2)_nAr, NH(CH_2)_nOH, (CH_2)_nOC_{1-6}alkyl,$" with
-- $NH(CH_2)_pAr, NH(CH_2)_pOH, (CH_2)_pOC_{1-6}alkyl$, --;
Line 66, please delete "a" after "amount of a compound of";

Column 45,
Line 23, please replace "$C(NH_2)$—$C(CN)_2$;" with -- $C(NH_2)=C(CN)_2$; --;
Line 26, please replace "$NH(CH_2)_nAr, NH(CH_2)_nOH, (CH_2)_nOC_{1-6}alkyl,$" with
-- $NH(CH_2)_pAr, NH(CH_2)_pOH, (CH_2)_pOC_{1-6}alkyl$, --;
Line 45, please replace "Philadelphia+ leukemia, Philadelphia+ leukemia," with
-- Philadelphia+ leukemia, Philadelphia- leukemia, --;

Column 46,
Line 10, please replace "$C(NH_2)$—$C(CN)_2$;" with -- $C(NH_2)=C(CN)_2$; --;
Line 13, please replace "$NH(CH_2)_nAr, NH(CH_2)_nOH, (CH_2)_nOC_{1-6}alkyl,$" with
-- $NH(CH_2)_pAr, NH(CH_2)_pOH, (CH_2)_pOC_{1-6}alkyl$, --;
Line 52, please replace "$C(NH_2)$—$C(CN)_2$;" with -- $C(NH_2)=C(CN)_2$; --;
Line 55, please replace "$NH(CH_2)_nAr, NH(CH_2)_nOH, (CH_2)_nOC_{1-6}alkyl,$" with
-- $NH(CH_2)_pAr, NH(CH_2)_pOH, (CH_2)_pOC_{1-6}alkyl$, --.

Signed and Sealed this

Twenty-fifth Day of October, 2005

JON W. DUDAS
*Director of the United States Patent and Trademark Office*